United States Patent
Demirci et al.

(10) Patent No.: US 10,228,372 B2
(45) Date of Patent: Mar. 12, 2019

(54) DETECTION, CAPTURE AND QUANTIFICATION OF BIOLOGICAL MOIETIES FROM UNPROCESSED BODILY FLUIDS USING NANOPLASMONIC PLATFORM

(71) Applicants: Utkan Demirci, Cambridge, MA (US); Fatih Inci, Cambridge, MA (US)

(72) Inventors: Utkan Demirci, Cambridge, MA (US); Fatih Inci, Cambridge, MA (US)

(73) Assignee: THE BRIGHAM AND WOMEN'S HOSPITAL, Boston, MA (US)

( * ) Notice: Subject to any disclaimer, the term of this patent is extended or adjusted under 35 U.S.C. 154(b) by 0 days.

(21) Appl. No.: 14/412,767

(22) PCT Filed: Jul. 3, 2013

(86) PCT No.: PCT/US2013/049263
§ 371 (c)(1),
(2) Date: Jan. 5, 2015

(87) PCT Pub. No.: WO2014/008363
PCT Pub. Date: Jan. 9, 2014

(65) Prior Publication Data
US 2015/0160218 A1    Jun. 11, 2015

Related U.S. Application Data

(60) Provisional application No. 61/668,274, filed on Jul. 5, 2012, provisional application No. 61/781,399, filed on Mar. 14, 2013.

(51) Int. Cl.
| | |
|---|---|
| *G01N 21/65* | (2006.01) |
| *G01N 21/00* | (2006.01) |
| *G01N 21/552* | (2014.01) |
| *G01N 33/543* | (2006.01) |
| *B01L 3/00* | (2006.01) |
| *G01N 33/569* | (2006.01) |
| *B82Y 15/00* | (2011.01) |
| *C07K 17/14* | (2006.01) |
| *G01N 33/53* | (2006.01) |
| *G01N 33/68* | (2006.01) |

(52) U.S. Cl.
CPC ........ *G01N 33/56988* (2013.01); *B82Y 15/00* (2013.01); *C07K 17/14* (2013.01); *G01N 21/554* (2013.01); *G01N 33/5308* (2013.01); *G01N 33/54346* (2013.01); *G01N 33/54373* (2013.01); *G01N 33/56916* (2013.01); *G01N 33/6866* (2013.01); *G01N 2333/16* (2013.01); *G01N 2469/10* (2013.01)

(58) Field of Classification Search
CPC ........ C12Q 2521/319; C12Q 2563/155; C12Q 2565/628; C12Q 1/6827; G01N 21/554
See application file for complete search history.

(56) References Cited

U.S. PATENT DOCUMENTS

| | | | |
|---|---|---|---|
| 2009/0148863 A1* | 6/2009 | Xu | G01N 33/54346 435/7.1 |
| 2011/0257494 A1 | 10/2011 | Glazier et al. | |
| 2013/0045474 A1* | 2/2013 | Rozmyslowicz | G01N 33/56988 435/5 |

FOREIGN PATENT DOCUMENTS

| | | |
|---|---|---|
| WO | 2005008243 A1 | 1/2005 |
| WO | 2007011331 A2 | 1/2007 |
| WO | 2011106057 A2 | 9/2011 |

OTHER PUBLICATIONS

Wang et al., "New trends in impedimetric biosensors for the detection of foodborne pathogenic bacteria", Sensors, 2012, 12:3449-3471.*
Wang et al. "Wang" (Sensors, 2012, 12:3449-3471).*
Higashi et al. "Higashi" (Polymer Journal, 2010, 42:95-99).*
Baptista et al., Progress in Molecular Biology and Translational Science, 104:pp. 427, 431-435 and 467-468.*
The International Search Report and Written Opinion as dated Oct. 24, 2013 for International Application No. PCT/US2013/049263.
Yixian Wang et al., New Trends in Impedimetric Biosensors for the Detection of Foodborne Pathogenic Bacteria, Sensors, Mar. 2012, vol. 12, p. 3449-3471, doi: 10.3390/s120303449.
Pedro V. Baptista et al., Nanoparticles in Molecular Diagnostics, Progress in Molecular Biology and Translational Science, vol. 104, pp. 427-488. doi: 10.1016/B978-0-12-416020-0.00011.5.
Gregory J. Hardy et al., Screening the interactions between HIV-1 Neutralizing Antibodies and Model Lipid Surfaces, Journal of Immunological Methods, 2012. Available online Oct. 18, 2011, vol. 376, No. 1, pp. 13-19.
Endo, et al., Label-Free Detection of Peptide Nucleic Acid—DNA Hybridization Using Localized Surface Plasmon Resonance Based Optical Biosensor, Anal. Chem., 2005, 77:6976-6984.
Zhang, et al., Towards a High-Throughput Label-Free Detection System Combining Localized-Surface Plasmon Resonance and Microfluidics, Lab on a Chip, 2012, 12:3012-3015.
European Patent Office, Supplementary European Search Report, Application No. EP 13812623, dated Feb. 11, 2016, 12 pages.

* cited by examiner

*Primary Examiner* — Barry A Chestnut
(74) *Attorney, Agent, or Firm* — Quarles and Brady, LLP

(57) ABSTRACT

A nanoplasmonic platform can be used for the detection and quantification of multiple HIV subtypes in whole blood with localized surface plasmon resonance. Among other things, this nanoplasmonic platform provides a viable way to detection and quantification of viral load at a point of care with significantly less cost, time, and laboratory resources than existing methods of detection. Although an example of HIV detection in whole blood is provided, the nanoplasmonic platform is adaptable to detect other pathogens and infectious agents or macromolecules.

21 Claims, 38 Drawing Sheets

DETECTION, CAPTURE AND QUANTIFICATION OF BIOLOGICAL MOIETIES FROM UNPROCESSED BODILY FLUIDS USING NANOPLASMONIC PLATFORM

CROSS-REFERENCE TO RELATED APPLICATIONS

This application represents the U.S. National Stage of International Application No. PCT/US2013/049263, filed Jul. 3, 2013 which claims the benefit of U.S. Provisional Patent Application Ser. No. 61/668,274 entitled "Nanodetection of Viral Load from Whole Blood" filed Jul. 5, 2012 and claims the benefit of U.S. Provisional Patent Application No. 61/781,399 entitled "Nanodetection of Pathogen Load from Whole Blood" filed on Mar. 14, 2013. The contents of these applications are incorporated by reference herein in their entirety for all purposes.

STATEMENT OF FEDERALLY SPONSORED RESEARCH OR DEVELOPMENT

The invention was made with government support under R01 A1081534, R01 EB015776, R21 A10871, R01 AI093282, U54 EB15408, and R21 AI087107 awarded by the National Institutes of Health and 106325 awarded by the Department of Defense. The United States government has certain rights in the invention.

BACKGROUND OF THE INVENTION

This invention relates to the detection of biological moieties such as infectious agents, pathogens, or biomarkers. In particular, this invention relates to a nanoplasmonic platform for the detection and quantification of one or more pathogens such as HIV, HBV, or *E. coli* at a point-of-care (POC) using localized surface plasmon resonance (LSPR) principle.

Detection of infectious agents or pathogens (e.g., virus, bacteria, and fungi) is critical for homeland security, public and military health. In recent years, infectious diseases, especially viral outbreaks such as SARS, H1N1 and HIV, have a tremendous global healthcare impact, since such viruses could rapidly evolve, spread, and turn into pandemics such as HIV/AIDS and Spanish flu that had a devastating global impact causing totally over 80 million deaths. To identify and control forthcoming epidemics, it will be a critical to develop rapid, reliable, accurate, and sensitive diagnostic technologies that have the ability to be tailored to multiple settings.

Effective, rapid, accurate, and simple detection of complex pathogens and infectious agents still poses significant biological and engineering challenges. Among other things, biological challenges can arise due to the presence of multiple subtypes and strains of the pathogen that makes it difficult to achieve repeatable and reliable capture efficiencies from bodily samples without demanding lengthy sample preparation steps.

To provide one exemplary case of the cost of this unaddressed detection need, it is estimated that annually over 450,000 infants are infected with HIV through mother-to-child transmission (MTCT), which is the primary cause of AIDS in children. Rapid progression of AIDS in infants causes early death. Combined data from nine clinical trials in Africa showed that 35% of HIV-1 positive infants die by the age of 1 and 52% of HIV-1 infected children die by the age of 2.

Studies have shown that long-term suppression of HIV-1 replication in infants can be achieved by initiating antiretroviral therapy (ART) to reduce AIDS-related morbidity and mortality, and improve the quality of life. In order to provide early AIDS care and ART to HIV-infected infants, early diagnosis is key as ART is not provided until infection has been established.

However, simple and rapid serological assays cannot detect HIV-infected infants until 18 months after birth. The late identification of AIDS children is due to the interference of maternal HIV-1 specific antibodies, which are passively transferred through the placenta and persist in infants for approximately 18 months. Unfortunately, the viral load assays used in developed countries are expensive and require significant instrumentation. Thus, the lack of cost-effective POC viral load assays that can effectively reach patients living in rural, isolated settings prevents identifying HIV-infected infants that would greatly benefit from starting ART. Thus, the monitoring the viral load of HIV at a POC for many patients, and infants in particular, is still an unaddressed challenge. Traditional detection techniques such as culturing, enzyme-linked immunosorbent assay (ELISA) and polymerase chain reaction (PCR) cannot be implemented at POC settings without equipped laboratories and extensive infrastructure.

In developed countries, HIV-1 viral load is monitored using commercial RNA assays, such as Roche COBAS®, Abbott RealTime, Siemens Versant™ and bioMerieux NucliSens®. However, implementation of these assays requires expensive equipment (e.g., thermal cyclers, $20,000), highly skilled personnel, and expensive reagents ($50-200 per test in the US), which in resource-constrained settings is unaffordable and unsustainable. Alternative viral load assays have been developed, such as the Ultrasensitive p24 assay, the ExaVir™ RT viral load assay, and real-time reverse transcriptase quantitative polymerase chain reaction (RT-qPCR). However, these assays are still costly requiring refrigeration and skilled operators. Additionally, throughput of the ExaVir™ RT viral load assay is low, with turnaround time of two days and is limited to 180 samples per week per operator. Miniaturized conventional ELISA for detection of p24 antigen or RT-qPCR for detection of HIV-1 RNA has been developed. However, these methods require complex on-chip designs due to multi-step manipulations such as labor-intensive sample preparation (plasma separation and RNA extraction), amplification (expensive reagents) and detection. Additionally, these methods require parallel testing of external standards for a standard curve, which further increase the device complexity. Thus, current viral load assays, due to technical requirements and costs, are not available to benefit AIDS patients at the POC in resource-constrained settings.

For early identification of HIV-positive infants, isolation of HIV-1 in cell cultures was initially used, although it was time-consuming, costly and technically demanding. Most commonly, MTCT is diagnosed via PCR to amplify HIV-1 DNA integrated into the genome of white blood cells (WBCs). However, performing PCR still requires highly-trained operators, is time-consuming, and more expensive than current rapid serological assays. There have been efforts to develop miniaturized PCR chips including chips employing RT-qPCR for HIV-1 RNA detection.

Thus, there remains a generalized need for the detection and quantification of one or more infectious agents or pathogens at the POC. More specifically, there is a need for new, simple, highly sensitive, specific, accurate, reliable, rapid, and feasible viral load assays that are necessary to avoid further infectious agent and pathogen propagation and to screen for initiating early treatment at the inception of an epidemic.

SUMMARY OF THE INVENTION

Infectious diseases such as SARS and HIV pose an omnipresent danger to global health. Reliable, fast, accurate and sensitive platforms that can be deployed at the point-of-care (POC) in multiple settings, such as airports and offices for detection of infectious pathogens are essential to interfere in epidemics and possible biological attacks.

Disclosed herein is a broadly applicable technology for quantitative, nanoplasmonic-based intact multiple pathogen and infectious agent detection at clinically relevant concentrations without any sample preparation directly from whole blood. The disclosed sensing platform is based on the unique nanoplasmonic properties of nanoparticles and the immobilization of antibodies for rapidly evolving subtypes of viruses.

Although this technology will be described with reference to viral load detection of various subtypes of HIV below, this technology may be equally applicable and adaptable to the detection of other biological moieties including, but not limited to, infectious agents, pathogens, organisms, or reaction products (including peptides, nucleic acids, peptide nucleic acids, carbohydrates, and the other biological and chemical relevant products) by changing the surface chemistry for pathogens, organisms, or reaction products having reasonably well-described markers available. For example, instead of viral detection the technology might be used to detect other pathogens, infectious agents, organisms, or reaction products such as bacteria, virus, fungi, nucleic acids, peptides, secreted cellular products, cell fragments, exosomes, and so forth. For example, $E.\ coli$ may be detected. This technology is also broadly applicable to other types of infectious diseases having reasonably well described biomarkers available including, but not limited to, influenza, hepatitis, malaria, dengue, epilepsy, and tuberculosis (tuberculosis might be found in sputum). Other (bio) markers such as KIM-1 (kidney injury molecule-1), which is a biomarker for human renal proximal tubule injury, might also be detected using this platform as just one example. This technology may also be utilized in the detection of bacteria, related biological macromolecules of bacteria, and neutrophils in peritoneal dialysis bags. Moreover, this technology may be applicable to detection of the products of reactions including, but not limited to, polymer reactions such as cross-linking and synthesis reactions, enzymatic reactions, and hydrolysis reactions. In some instances, a phase change may be detectable and/or a change in size or molecular weight. Additionally, while the samples provided in the examples below are blood samples, other types of samples or bodily fluids may be used including, but not limited to, serum, urine, saliva, vaginal secretions, and sputum. These samples may be obtained from humans or from animals and may contain mammalian cells; moreover, these samples may include plant cells, yeast and fungi.

In this disclosure, the capture of multiple HIV subtypes (A, B, C, D, E, G, and subtype panel) on a biosensing surface of a nanoplasmonic platform is presented as well as the detection and quantification of the virus using localized surface plasmon resonance principle. These results were compared to RT-qPCR as a gold standard and the disclosed system presented high repeatability (56-90%). Preliminary results have shown that the nanoplasmonic platform results correlated significantly for viral load concentrations ranging from 50 to $10^6$ copies/mL in spiked whole blood samples and HIV-infected patient blood samples, indicating that the microchip performs accurately with a clinically reasonable error. This method offers an assay time of 1 hour and 10 minutes (1 hour for capture, 10 minutes for detection and data analysis). This assay time can be shortened by changing the volume of samples and optimizing the biosensing platform dimensions. These samples corresponded to concentrations that cover the treatment failure range including the current definitions of the World Health Organization (WHO), Department of Health and Human Services (DHHS) and AIDS Clinical Trials Group (ACTG).

The disclosed system is shown to be accurate, repeatable, and reliable to capture intact viruses without any damage on the virus structure and characteristics including their capsid structure and genetic content. This capture can occur with high capture specificity and efficiencies using immuno-surface chemistry approaches directly from whole blood samples without any sample preprocessing step.

This nanoplasmonic platform may be implemented in a lab on a low-cost microfluidic chip that is subjected to LSPR on location to attain a timely and accurate pathogen and/or infectious agent count in whole blood sample. In the examples below, the viral load microchips can capture HIV-1 with high efficiency and specificity (which is confirmed by the examples below) and are readable with a portable lensless charge coupled device (CCD)-based LSPR technology for label-free detection and quantification of HIV-1. The use of CCD system eliminates the need for fluorescence imaging. The combination of the microchip with the lensless system provides a novel portable and battery-powered viral load system for resource-constrained settings. This overcomes many of the deficiencies with existing technologies for viral load detection which are limited by required equipment, time, cost, and other processing factors.

Thus, this broadly applicable platform holds great promise to become a detection platform at the POC settings in rural and remote areas as well as in the hospital and primary care settings. Further, these approaches have wide implications and potential to be applicable in the U.S. as personalized bed-side diagnostic technologies. As an example, such microchips can also potentially be used to capture, detect and rapidly quantify other viruses such as dengue and H1N1 as well as oncoviruses and circulating tumor cells (CTCs are one per billion blood cells, peritoneal cavity fluid, and lymph circulation fluid) for prevention and treatment.

These and still other advantages of the invention will be apparent from the detailed description and drawings. What follows is merely a description of a preferred embodiment of the present invention. To assess the full scope of the invention, the claims should be looked to as the preferred embodiment is not intended to be the only embodiment within the scope of the claims.

BRIEF DESCRIPTION OF THE DRAWINGS

In FIG. 10A, eight discarded HIV-infected patient samples in whole blood were evaluated using nanoplasmonic platform, and the platform presented a viral load ranging from $(1.3\pm0.7)$ $\log_{10}$ copies/mL to $(4.3\pm1.2)$ $\log_{10}$ copies/mL. RT-qPCR count presented a viral load ranging from $(2.7\pm0.1)$ $\log_{10}$ copies/mL to $(3.6\pm0.1)$ $\log_{10}$ copies/mL in patient samples. (n=5-6, error bars represent standard error of the mean (SEM)). FIG. 10B illustrates that Bland-Altman Analysis between the nanoplasmonic platform and RT-qPCR counts did not demonstrate an evidence for a systematic bias for HIV viral load for HIV-infected patient blood samples.

FIG. 12A shows a schematic of a viral load microchip fabrication process. FIG. 12B shows a prototype viral load microchip. FIG. 12C shows a top view schematic of a disposable microchip and fluid reservoirs in which the chip has fluidic interface between microchannels.

In FIG. 15A(i), the surface is functionalized with gold nanoparticles and anti-Carbamazepine (CBZ) antibody for specific detection of CBZ molecules. In FIG. 15A(ii), a droplet of blood from fingerprick is injected into microfluidic channels. Then, the extinction wavelength shift is measured using a portable spectrophotometer, the results of which are generally shown in FIG. 15B in which wavelength shift due to the specific binding of CBZ molecules to the anti-CBZ antibody is illustrated.

FIG. 16A provides the aggregated data for the validation of the nanoplasmonic platform with multiple HIV subtype (A, B, C, D, E, G) spiked in whole blood and HIV-infected patient samples from FIG. 6A-6H in a single chart. The limit-of-detection was calculated for each subtype, and compared to the control sample. (i.e., whole blood without HIV) as is illustrated in FIG. 16B. The presented wavelength shifts of multiple HIV subtype samples are significantly different than the control sample (Statistical assessment on the results was performed using non-parametric Kruskal-Wallis one-way analysis of variance followed by Mann-Whitney U test with Bonferroni correction for multiple comparisons. Statistical significance threshold was set at 0.05, $p<0.05$).

DETAILED DESCRIPTION

Figure 1:
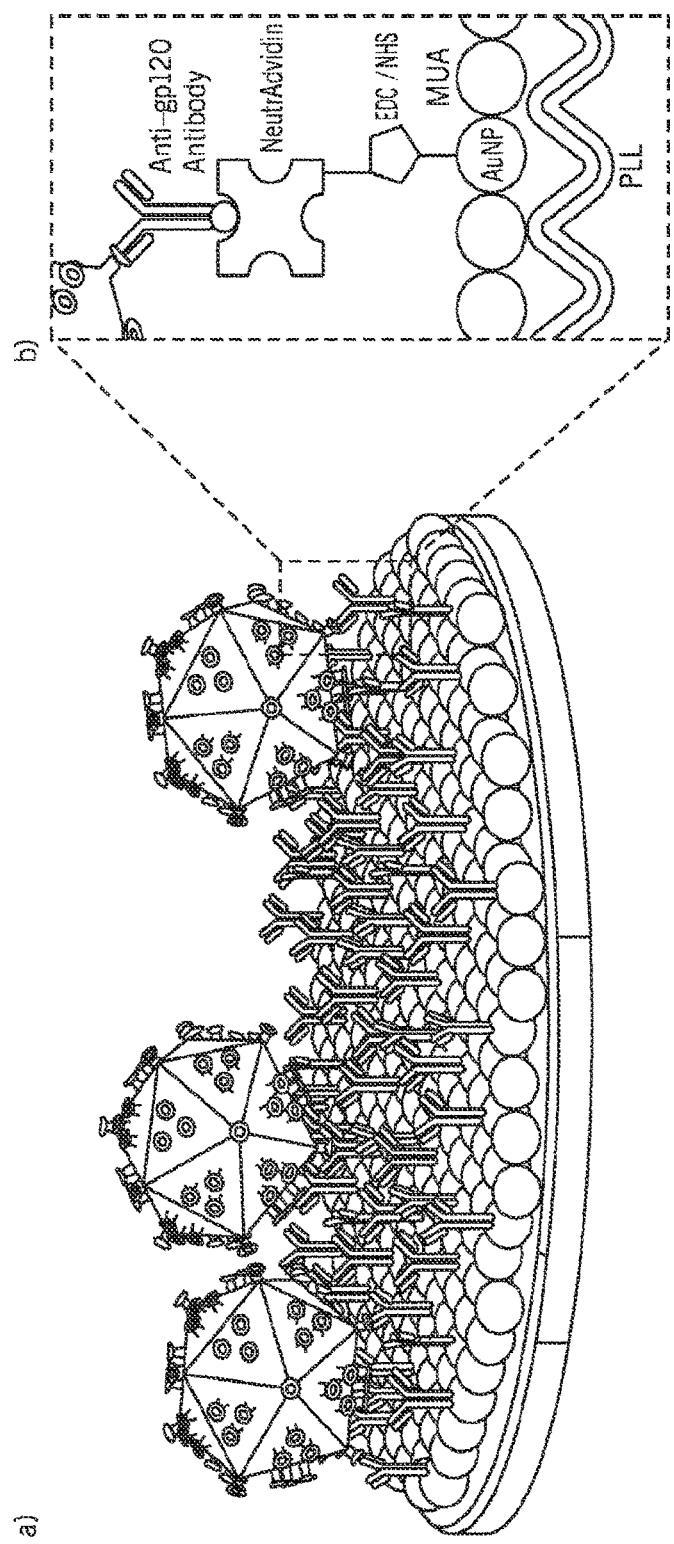
FIGS. 1A and 1B illustrate an exemplary nanoplasmonic platform for viral load detection.

Biosensing platforms are disclosed herein for direct intact multiple pathogen and/or infectious agent detection using the nanoplasmonic properties of nanoparticles. These disclosed technology platforms and systems take a significant step toward providing POC tests at resource-constrained settings as well as hospital and primary care settings.

It should be noted that label-free biodetection platforms such as electrical, mechanical and optical mechanisms have been recently used for the detection and diagnostics of infectious agents. These biosensing technologies offer multiple pathogen and disease detection applications ranging from laboratory research to medical diagnostics and drug development/treatment to engaging biologic threats.

A nanoplasmonic platform for the detection and quantification of one or more pathogens in a bodily fluid sample, such as a whole blood sample, is disclosed. The nanoplasmonic platform includes a substrate having an immobilization layer, a plurality of gold nanoparticles immobilized on the immobilization layer, and one or more antibodies linked to the gold nanoparticles in which the antibodies are configured to selectively bind to the pathogen(s) and infectious agent(s). The nanoplasmonic platform is adapted for the detection and quantification of the pathogen(s) and infectious agent(s) using localized surface plasmon resonance (LSPR). This technology may be broadly applicable to the detection of any type of biological moiety that has a corresponding recognition element (e.g., antibody), and it is contemplated that nanoparticles other that gold nanoparticles might be employed. As some non-limiting examples, the recognition elements include one or more of an anti-gp120 antibody, an anti-gp41 antibody, an anti-gp24 antibody, and lectin and the recognition elements could be adapted to detect *E. coli* or HBV.

When describing the nanoplasmonic platform and binding of the antibody thereto, terms such as linked, bound, connect, attach, interact, and so forth should be understood as referring to linkages that result in the joining of the elements being referred to, whether such joining is permanent or potentially reversible. These terms should not be read as requiring the formation of covalent bonds, although covalent-type bond might be formed.

The substrate of the nanoplasmonic platform can be optically transparent to facilitate LSPR. Polystyrene, glass parylene, quartz crystal, graphene and mica layers, and poly(methyl methacrylate) are good candidates for the substrate. They are good candidates because they are optically transparent and are capable of supporting the functionalized gold nanoparticles which selectively bind to the pathogen(s) and infectious agent(s) via the surface recognition elements such as antibodies and which possess the nanoplasmonic properties that facilitate LSPR detection of the binding detection and capture events.

The immobilization layer of the nanoplasmonic platform can be, for example poly-l-lysine (although other layers may be able to immobilize the nanoparticles on the substrate and not interfere with LSPR detection), and can have amine-terminated groups that are used to immobilize the plurality of gold nanoparticles. The immobilization layer may be functionalized with at least one of the metal binding groups such as amine groups or thiol groups, although other attachments between the layer and the substrate or the gold nanoparticles may also be employed as long as it does not impair the ability of the nanoplasmonic platform to be read using LSPR.

To link the one or more surface recognition elements such as antibodies to the gold nanoparticles, a modified support surface may be formed by preparing a surface of the plurality of gold nanoparticles using a mercaptoundecanoic acid to form carboxyl groups, reacting N-Ethyl-N'-(3-dimethylaminopropyl) carbodiimide hydrochloride with the carboxyl groups to form an amine reactive intermediate, and stabilizing the amine reactive intermediate by the of N-hydroxysulfosuccinimide to form the modified support surface. The modified support surface may be linked to a NeutrAvidin protein which is used to immobilize an anti-gp120 antibody. The anti-HIV gp120 antibody accommodates the detection of various subtypes of HIV because this antibody is adapted to bind to multiple subtypes of HIV. Additionally, other or additional antibodies may be present based on the pathogens and infectious agents to be detected. It is contemplated that multiple pathogens may be detected on a single nanoplasmonic platform. In some embodiments, the antibody may be a polyclonal antibody. In the context of HIV detection, the antibody may be, for example, a gp120 antibody, a gp41 antibody, a gp24 antibody, or lectin, all of which are able to detect multiple subtypes of HIV. Additionally, in some forms, the modified support surface is linked to at least one of a protein A, a protein G, a protein A/G, a Streptavidin protein, and a NeutrAvidin protein which is used to form chemical bonds to immobilize recognition elements such as the antibody on the modified support surface.

After the binding of an antigen to the antibody, the nanoplasmonic platform exhibits an observable change in wavelength, in at least one of wavelength shift and extinction intensity, when subjected to LSPR in comparison to when no binding has occurred due to the exceptional nanoplasmonic properties of the gold nanoparticles.

The nanoplasmonic platform may be based on a microfluidic device having an inlet for reception of the sample in which the inlet is in fluid communication with a capture detection channel that includes one or more antibodies linked to the plurality of gold nanoparticles therein. The microfluidic device can further comprises a filter disposed between the inlet and the capture detection channel in which the filter has a porosity that filters the sample to produce a filtered sample for selectively binding to the at least one antibody. In this way, the capture efficiency of the system can be improved.

A method of making a nanoplasmonic platform of the type described above is also disclosed. This method includes depositing an immobilization layer on a substrate (which in some forms may be poly-l-lysine), immobilizing a plurality of gold nanoparticles on the immobilization layer, and linking one or more antibodies to the gold nanoparticles in which the one or more antibodies are configured to selectively bind to pathogen(s) and infectious agent(s).

As mentioned above, the substrate may be optically transparent to facilitate LSPR measurements and may include polystyrene, glass, parylene, quartz crystal, graphene and mica layers, and/or poly(methyl methacrylate).

Again, the antibody attached to the gold nanoparticles may be an anti-HIV gp120 antibody and pathogen and infectious agent may include HIV. Alternatively, polyclonal antibodies may be used as well as any of the antibodies describe above may be used to detect HIV. Again, some of the antibodies that may be used to detect HIV include gp120, gp41, gp24, and lectin.

According to one specific form of the method, a modified support surface for linking the at least one antibody to the gold nanoparticles may be formed by the steps of preparing a surface of the plurality of gold nanoparticles using a mercaptoundecanoic acid to form carboxyl groups, reacting N-Ethyl-N'-(3-dimethylaminopropyl) carbodiimide hydrochloride with the carboxyl groups to form an amine reactive intermediate, and stabilizing the amine reactive intermediate using the of N-hydroxysulfosuccinimide to form the modified support surface. The modified support surface may be linked to a NeutrAvidin protein which is used to immobilize an anti-HIV gp120 antibody.

Also disclosed herein is a method of detecting a pathogen and/or infectious agent in a sample using the nanoplasmonic platform. The method of detection includes receiving the sample on the nanoplasmonic platform to capture a pathogen and/or infectious agent and performing localized surface plasmon resonance on the nanoplasmonic platform to obtain a wavelength signal and extinction intensity corresponding to the sample received on the nanoplasmonic platform.

The wavelength signal corresponding to the sample received on the nanoplasmonic platform may be used in a comparison to determine whether the pathogen has bound to the at least one recognition element such as an antibody on the nanoplasmonic platform. This permits for the detection of a pathogen and/or infectious agent or pathogen subtype by the nanoplasmonic platform as well as a quantity of the pathogen and/or infectious agent in the sample (i.e., a viral load count in an unprocessed whole blood sample, a serum sample). The wavelength signal that is read and used as a basis for comparison may be, for example, a wavelength shift and/or an extinction intensity. The examples provided below relay experimental data when the pathogens being detected is multiple subtypes of HIV.

The nanoplasmonic platform may be based on a microfluidic device. The microfluidic device may have an inlet for the reception of the sample in which the inlet is in fluid communication with a capture detection channel that includes at least one antibody linked to the plurality of gold nanoparticles. The step of receiving the sample on the nanoplasmonic platform may include flowing the sample through the capture detection channel to selectively bind the pathogen and/or infectious agent to the at least one recognition element such as an antibody before the sample is subjected to localized surface plasmon resonance. In some forms, the microfluidic device can further include a filter disposed between the inlet and the capture detection channel and the method further includes the step of filtering the sample to produce a filtered sample prior to the step of selectively binding the pathogen and/or infectious agent to the at least one antibody in the capture detection channel.

Below, we demonstrated for the first time HIV viral load quantification using a nanoplasmonic optical detection system using multiple subtypes in HIV-infected patient samples as a model system. Here, we present for the first time a reliable, feasible, label-free, fluorescence-free and repeatable technology that captures multiple viral subtypes from unprocessed whole blood, and subsequently quantifies and reports viral load.

One exciting application of this technology is in infant testing where HIV status cannot be monitored by white blood cell counting, and viral load assays are required. The presented nanoplasmonic platform technology detected virus particles in whole blood of HIV-infected patients, which contain HIV antibodies. Since antibodies in men and women would not be any different, antibodies transferred from women to their infants would not be expected to have any greater effect in interfering with detection (i.e., if antibodies do not interfere with detection in infected adults, passively transferred antibodies will not interfere with detection in infants). In the clinical samples tested so far, no interference effects have been observed.

Specific examples of the process or nanoplasmonic platform, method of making this nanoplasmonic, and method of detecting pathogens and/or infectious agents are provided below. These examples are offered for illustrative purposes only, and are not intended to limit the scope of the present invention in any way. Indeed, various modifications of the invention in addition to those shown and described herein will become apparent to those skilled in the art from the foregoing description and the following example and fall within the scope of the appended claims.

Example I

Referring first to FIGS. 1A and 1B, a nanoplasmonic viral load detection platform is illustrated. FIG. 1A shows the capture of HIV on the antibody immobilized biosensing surface and FIG. 1B illustrates the structure of the nanoplasmonic platform and various layers. The construction of the exemplary nanoplasmonic platform is now described along with data characterizing of the platform, including some intermediate forms of the platform.

The nanoplasmonic platform is constructed using a polystyrene surface as a base substrate. For the prepared trials, polystyrene well plates were purchased from Corning Inc. of Corning, N.Y. The polystyrene surfaces were first washed with absolute ethanol and distilled water, then dried under nitrogen gas. The ethanol (200 proof) was purchased from Fisher Scientific of Fair Lawn, N.J. Following cleaning steps, the polystyrene surface was modified by poly-l-lysine (PLL) to form amine-terminated groups. A series of densities of PLL (from 0.01 to 0.1 mg/mL) in 1× phosphate buffer saline (PBS) were evaluated, and then, surfaces were incubated at 4° C. overnight. The PLL was purchased from Sigma Co. of St. Louis, Mo. and the phosphate buffered saline (PBS, pH=7.4, 1×) was purchased from Invitrogen Co. of Carlsbad, Calif.

After PLL modification, 40 μL of gold nanoparticle solution was loaded onto each surface and incubated at 4° C. overnight for binding and seeding of nanoparticles onto the support material. The gold nanoparticles, having a 10 nm diameter, were purchased from TedPella of Redding, Calif.

To enable the capture of HIV on the biosensing surface, after the starting polystyrene surface was modified by poly-l-lysine (PLL) to generate amine-terminated groups and gold nanoparticles (AuNP) were immobilized on the amine-terminated surface, then additional layers were prepared to support and immobilize the antibody of interest. The gold nanoparticle immobilized surface was first activated by application of 100 μL of 1 mM 11-Mercaptoundecanoic acid (MUA) dissolved in ethanol. MUA forms carboxyl groups for crosslinking agents. N-Ethyl-N'-(3-dimethylaminopropyl) carbodiimide hydrochloride (EDC) (100 mM EDC dissolved in 50 mM MES buffer at pH 5.0) reacts with the carboxyl groups to form amine reactive intermediate. EDC-mediated coupling was stabilized by the addition of N-hydroxysulfosuccinimide (NHS) (50 mM NHS dissolved in 50 mM MES buffer at pH 5.0). After EDC/NHS coupling reaction, 100 μL of NeutrAvidin™ (NA) (0.1 mg/mL) was placed on the modified support surface to immobilize antibodies on the surface and enhance the capture efficiency. To minimize nonspecific binding on both inactive and reactive areas of the surface, 100 μL of 10% BSA was used as a blocking agent on each surface and incubated at 4° C. for an hour. After the BSA blocking step, 5 μg/mL of biotinylated anti-gp120 polyclonal antibodies were placed onto biotin binding sites on NeutrAvidin by loading 100 μL of antibody solution onto each modified surface and incubated at 4° C. for an hour. The MUA, EDC, NHS and BSA (10%) were obtained from Aldrich Chemical Co. of Milwaukee, Wis. MES was purchased from Sigma Co. of St. Louis, Mo.

NeutrAvidin™ protein was obtained from Pierce Biotechnology of Rockford, Ill. Biotinylated, goat anti-HIV gp120 antibody was obtained from Abcam Inc. of Cambridge, Mass.

It is noted that metal nanoparticles have been used in drug delivery and clinical diagnostics, and their nanoplasmonic properties present the advantage of light coupling upon the changes on the surface. Association and/or dissociation onto metal nanoparticles lead to changes in the absorbed wavelength in LSPR. Each modification on the metal nanoparticle surface causes an extinction intensity change and, it enables a broad window for spectral measurements with a high signal-to-noise ratio and minimal background signal.

Thus, biosensing platforms incorporating nanoparticles have been used in various biochemical sensing platforms and spectroscopies allowing picomolar sensitivity to detect protein and nucleic acid interactions. Although localized surface plasmon resonance principles have been utilized by others for protein and nucleic acid detection applications, intact viral detection and viral load quantification has not been performed from unprocessed whole blood.

However, there are a number of engineering and sampling challenges in both production and clinical testing of metal nanoparticle-based detection methods. First, typical chemical and physical modifications of nanoparticles (e.g., plasma treatment and exposure to highly acidic conditions) can lead to irreversible aggregation, resulting in degradation of optical characteristics. Also, existing nanoparticle-based pathogen detection methods have suffered from the challenges associated with direct exposure to unprocessed whole blood, including non-specific binding and the requirement for extensive sample preparation, thus reducing clinical relevance for POC applications. Currently, diagnostic tests require sample preprocessing including plasma separation to prevent inaccuracy in signal amplification and quantification steps. On the other hand, it is a significant challenge to deploy these biosensing platforms into a multiplexed format that can detect multiple subtypes of pathogens from unidentified patient samples.

Example II

Figure 2:
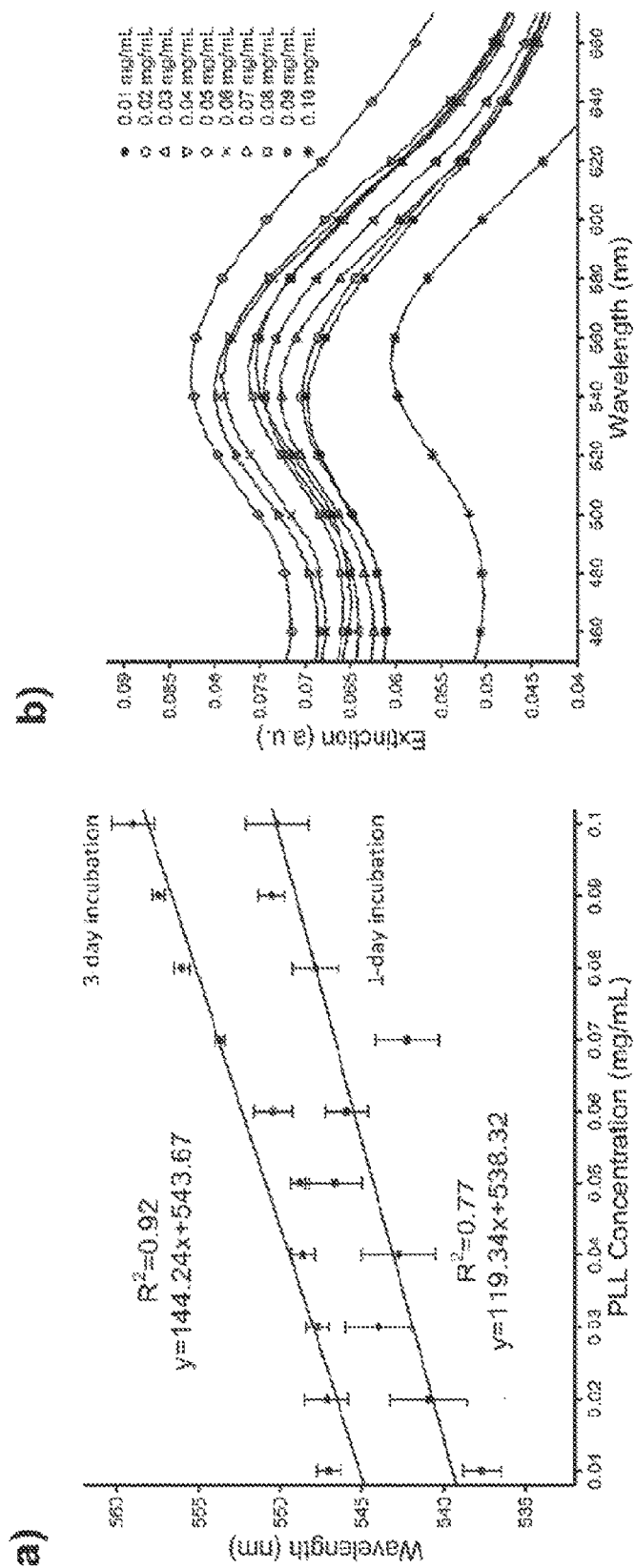
FIGS. 2A and 2B illustrate the surface modification of polystyrene (PS) surfaces using poly-l-lysine (PLL) and the spectral peak shifts and extinction intensities corresponding to the application of varying PLL concentrations on the PS surface.

To evaluate gold nanoparticle binding and seeding on polystyrene surface, a series of poly-l-lysine (PLL) concentrations (0.01 to 0.1 mg/mL) were evaluated and a linear concentration-dependent wavelength shift was observed as illustrated in FIG. 2A. The preparation of the surfaces to evaluate gold nanoparticle incubation time on amine-terminated polystyrene surface was performed with 1-day and 3-day incubation steps. FIG. 2A shows a statistically comparable correlation between wavelength shift and PLL concentration for 1-day and 3-day incubation steps. Based on these results, it was established that the experiments could be prepared using the 1-day incubation of PLL to decrease the incubation time for the preparation of the devices.

As shown in FIG. 2A, the individual wavelength of bare gold nanoparticles shifted from 518 nm to 546.4±1.6 nm, when PLL concentration (1-day incubation) was increased from 0.01 to 0.1 mg/mL. The number of amine groups played a notable role in nanoparticle binding onto the surface as it is believed that, at least up point, the concentration of PLL increases the number of amine-terminated groups to immobilize the gold nanoparticles. On the other hand, PLL concentrations above 0.1 mg/mL were observed to cause a collapsed polymer formation on the substrate, and a further increase in the concentration of gold nanoparticle binding sites on the surface was not observed as is generally evidenced by FIG. 2B.

Wavelength peak shifts by gold nanoparticle immobilization at PLL concentrations ranging from 0.01 to 0.1 mg/mL were then evaluated using a 1-day PLL incubation step and are illustrated in FIG. 2B. In the experiments, 0.05 mg/mL PLL concentration was chosen to avoid excessive dilution steps reducing possible variations in surface chemistry. Further, 0.05 mg/mL of PLL provided a high extinction coefficient at this PLL concentration to maximize gold nanoparticle binding onto the PLL treated surface (n=6, error bars represent standard error of the mean). Following each modification step, surfaces were rinsed with 1×PBS three times to minimize possible variations in the wavelength and intensity measurements.

It should be noted that metal nanoparticles that vary in size, shape, and material present different maximum wavelength points. This property allows for tuning of the nanoplasmonic wavelength point throughout the visible, near-infrared, and into the infrared region of the electromagnetic spectrum, offering flexibility. To avoid batch-to-batch variations and to create a reproducible platform, the various samples presented herein used the same batch of gold nanoparticle solution for reproducible nanoplasmonic measurements.

Example III

At each surface modification and after an HIV capture step, spectral analysis was monitored by either curve fitting analysis or experimental data maximum method, which reports the peak shifts at the maximum extinction wavelength. Each binding study was characterized with a detected shift of the maximum extinction point of gold nanoparticles by Varioskan® Flash Spectral Scanning Multimode Readers, Thermo Scientific. The measuring mode was set to scan the extinction changes per wavelength from 400 nm to 700 nm over 301 steps. The detection light beam area of the spectrometer was indicated as 3.14 mm² (maximum). The spectral resolution and intensity accuracy of the instrument with fixed slit setting was 1 nm and 0.003 a.u. extinction intensity. We performed 6 replicates for nanoplasmonic measurements for all samples.

To analyze the wavelength data, we employed two approaches (i.e., curve fitting and experimental data maximum). In the first method, a software code (e.g. MATLAB) was written to find the nanoplasmonic wavelength peak of each recorded spectra from curve fitting. A Fourier type expansion with 8 harmonics (i.e., $$f(x)=a_0+\Sigma_{n=1}^{8}(a_n \cos(n\omega x)+b_n \sin(n\omega x))$$

where $\omega$ is the fundamental frequency of the signal, $a_n$ and $b_n$ are expansion coefficients) was used to fit to each recorded spectra. The $R^2$ values were found to be greater than 0.99 with the MATLAB fit command. The wavelengths at the maximum extinction value for each recorded spectra were extracted from the curve fits and were rounded to the first decimal digit considering the finite resolution of the experiment. Individual reference curve subtraction was performed for each HIV subtype curve at a given virus concentration from the corresponding reference curve. All data for wavelength measurements were presented as the mean of wavelength measurements±standard error of the mean (SEM). The experimental spectra evaluated by the experimental data maximum method were compared with the Fourier type curve fitting analysis.

In the second data analysis method, nanoplasmonic wavelength peak was determined as the wavelength at the maximum extinction value, and all data for wavelength and extinction intensity measurements were presented as the mean of wavelength or extinction intensity measurements±SEM. For each HIV subtype curve at a given virus concentration, individual reference curve subtraction was carried out from the corresponding reference curve. Considering the resolution of the instrument, the data was presented with one decimal digit in the results, and the errors from the finite resolution of the spectrometer were considered in the analysis.

Figure 3:
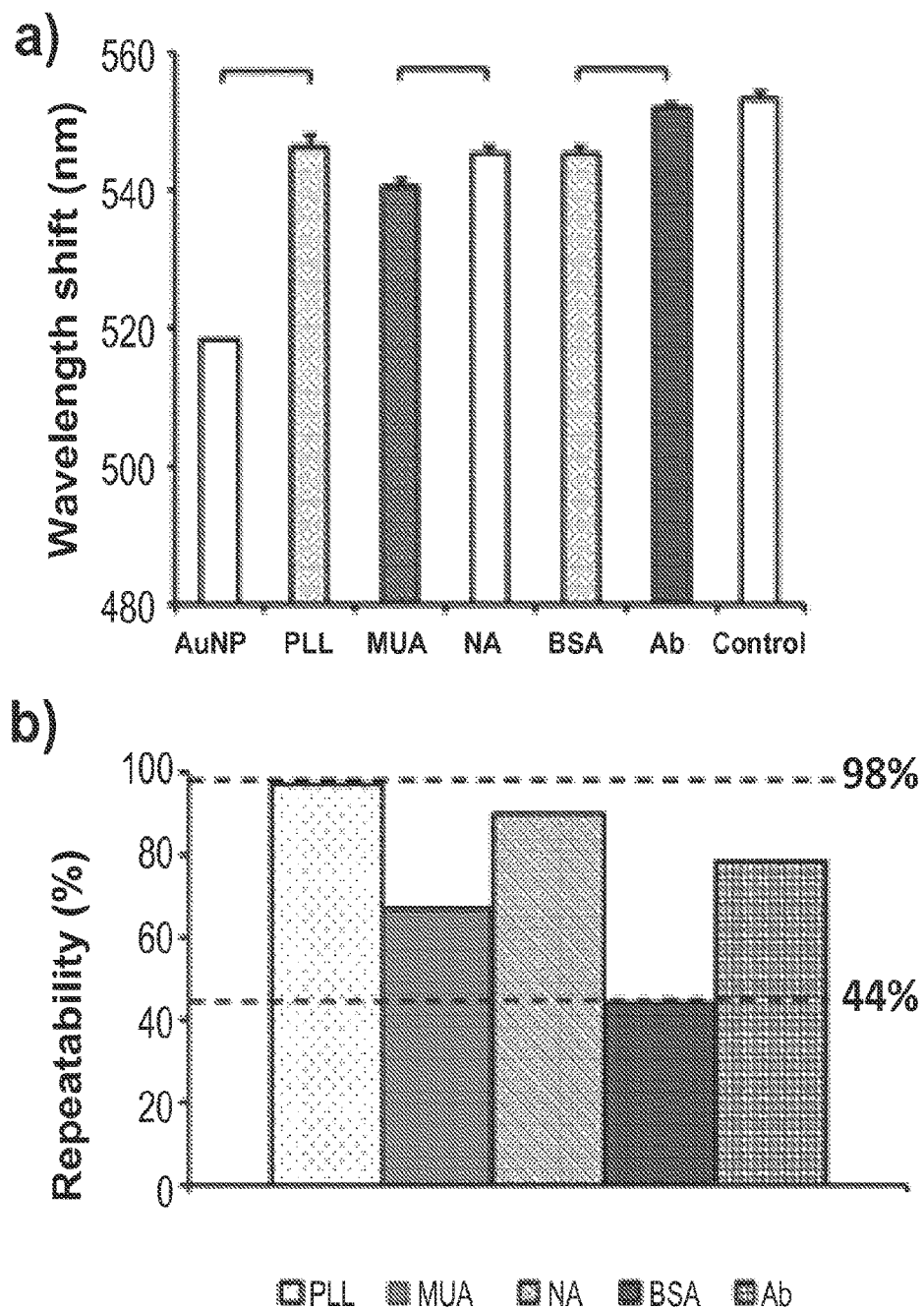
FIGS. 3A and 3D illustrate the observed wavelengths over a layer-by-layer surface preparation of the nanoplasmonic platform and the observed wavelength peak shift between a control whole blood sample and various whole blood samples spiked with a subtype or subtype panel of HIV.
FIGS. 3B and 3C illustrate the repeatability parameter for surface chemistry in terms of wavelength and extinction intensity, respectively.
Figure 3:
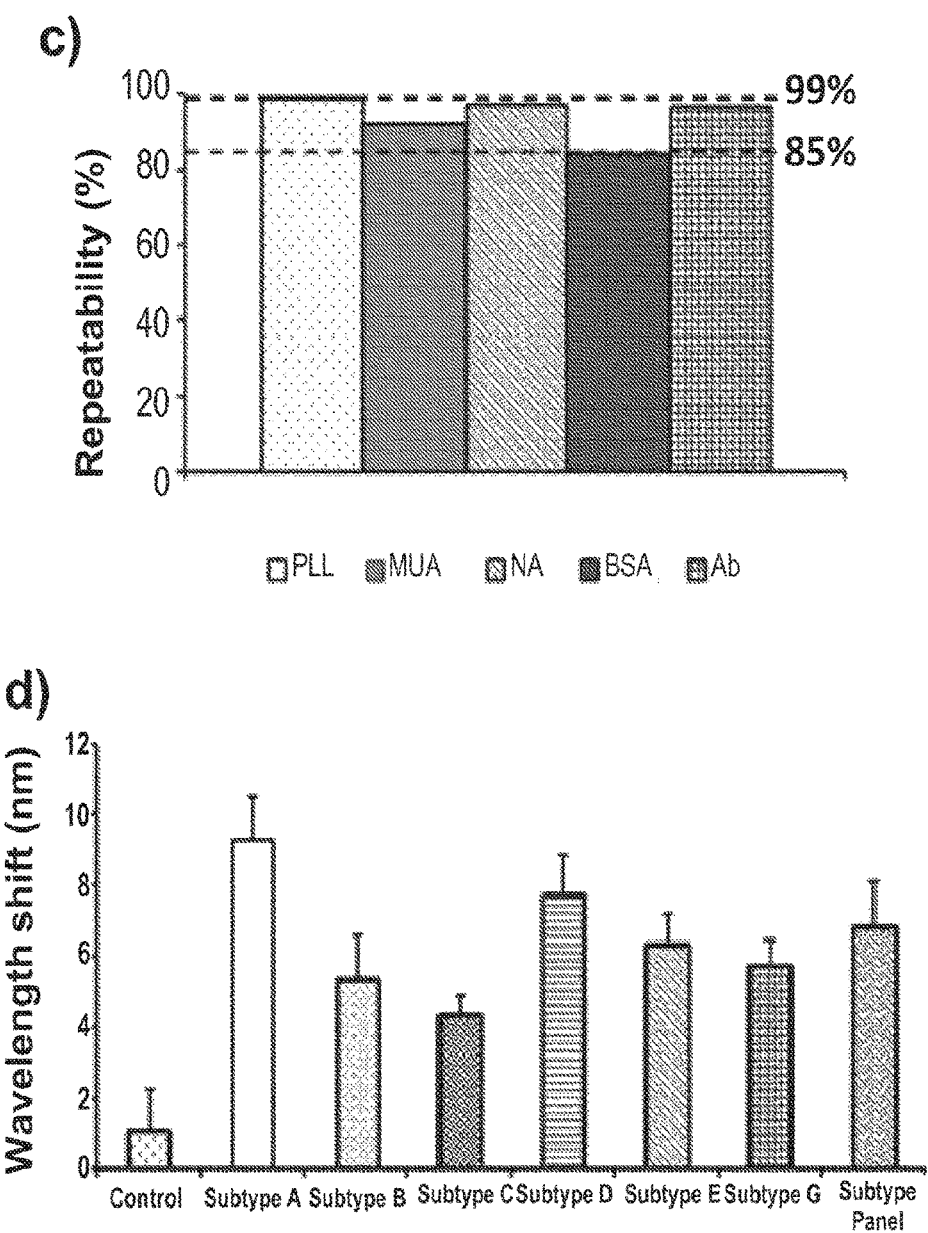
Figure 4:
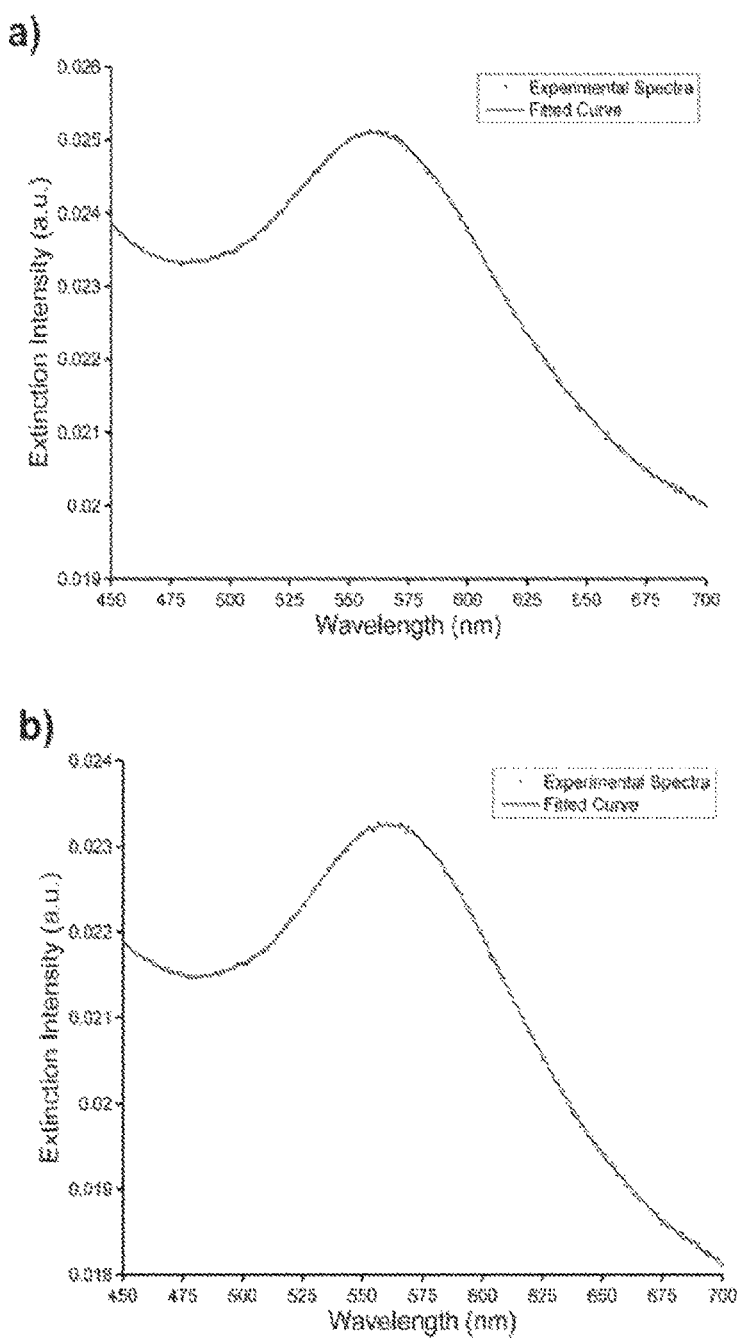
FIGS. 4A through 4H illustrate the original wavelength spectra and curve fitting analysis for multiple HIV subtypes.
Figure 4:
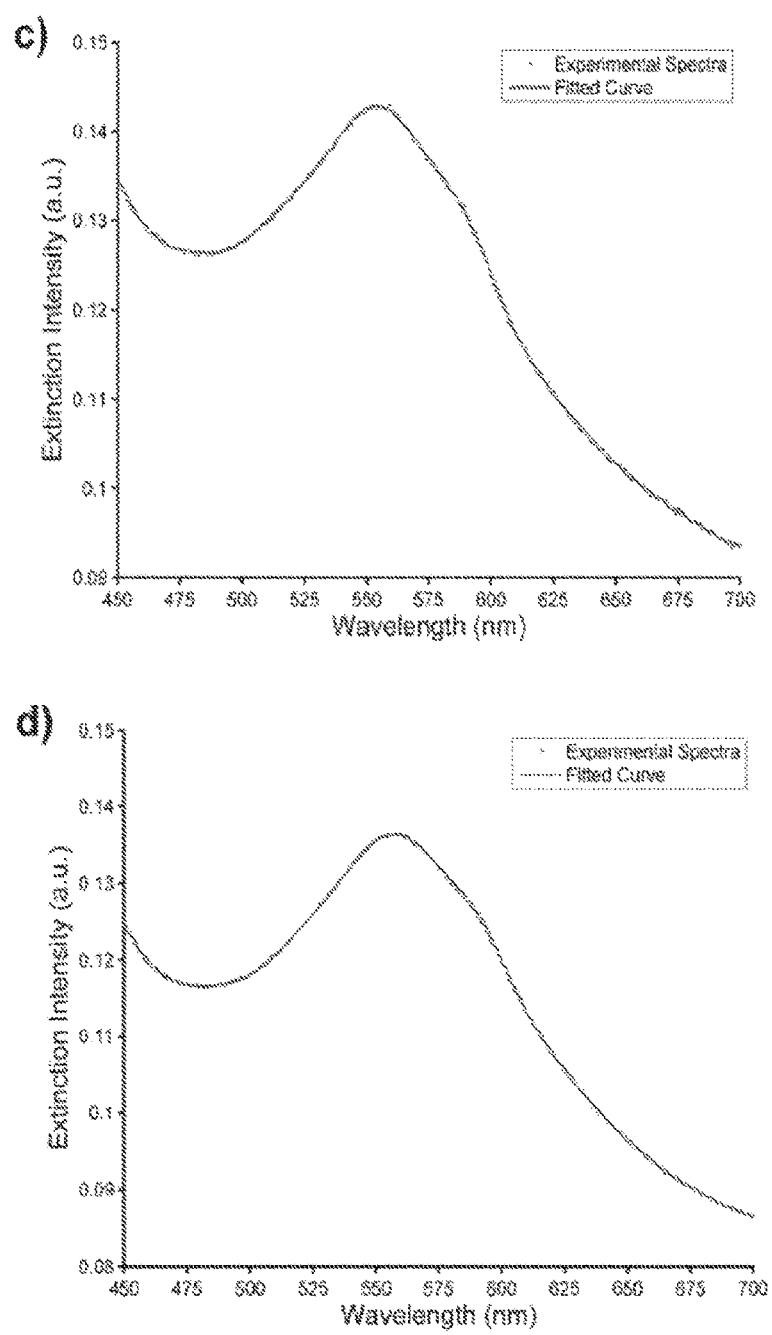
Figure 4:
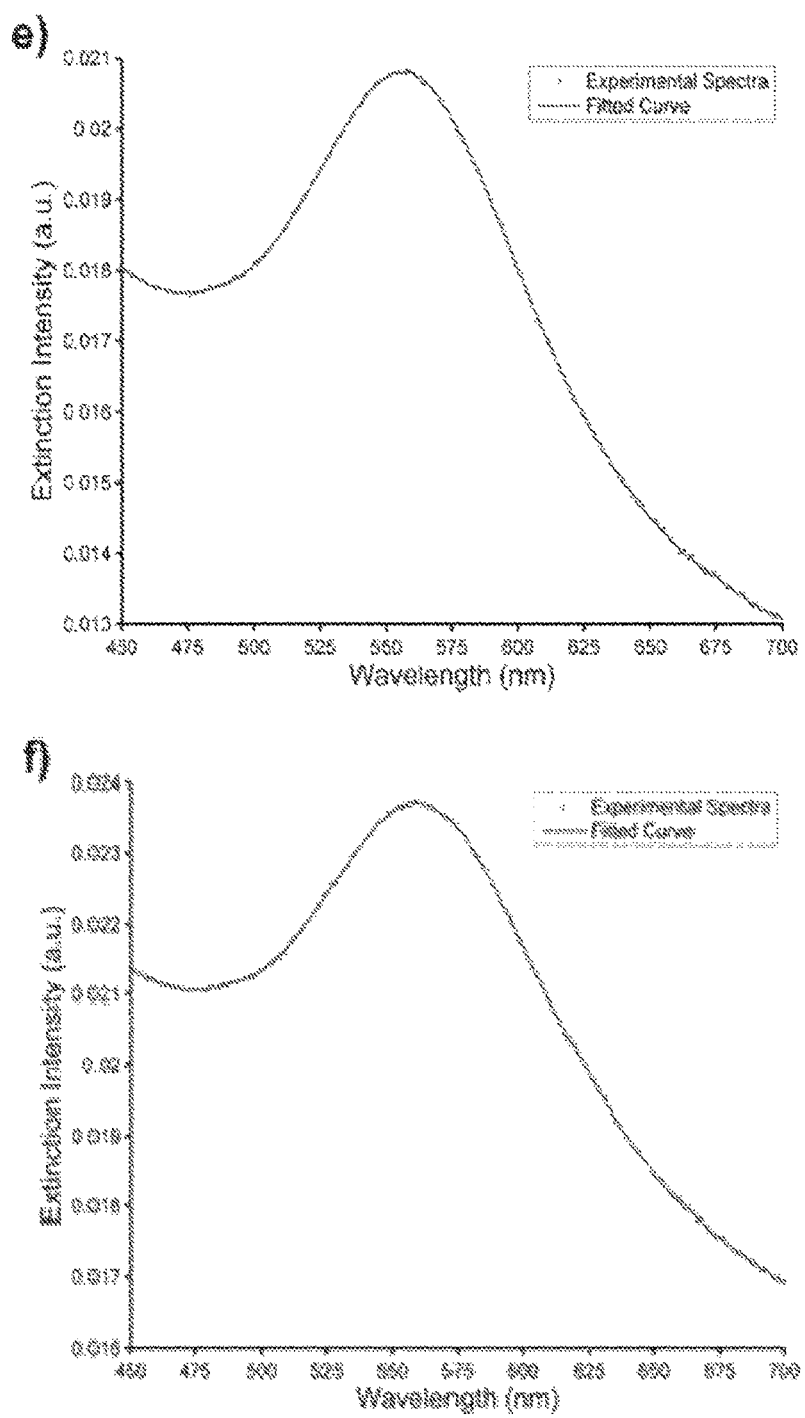
Figure 4:
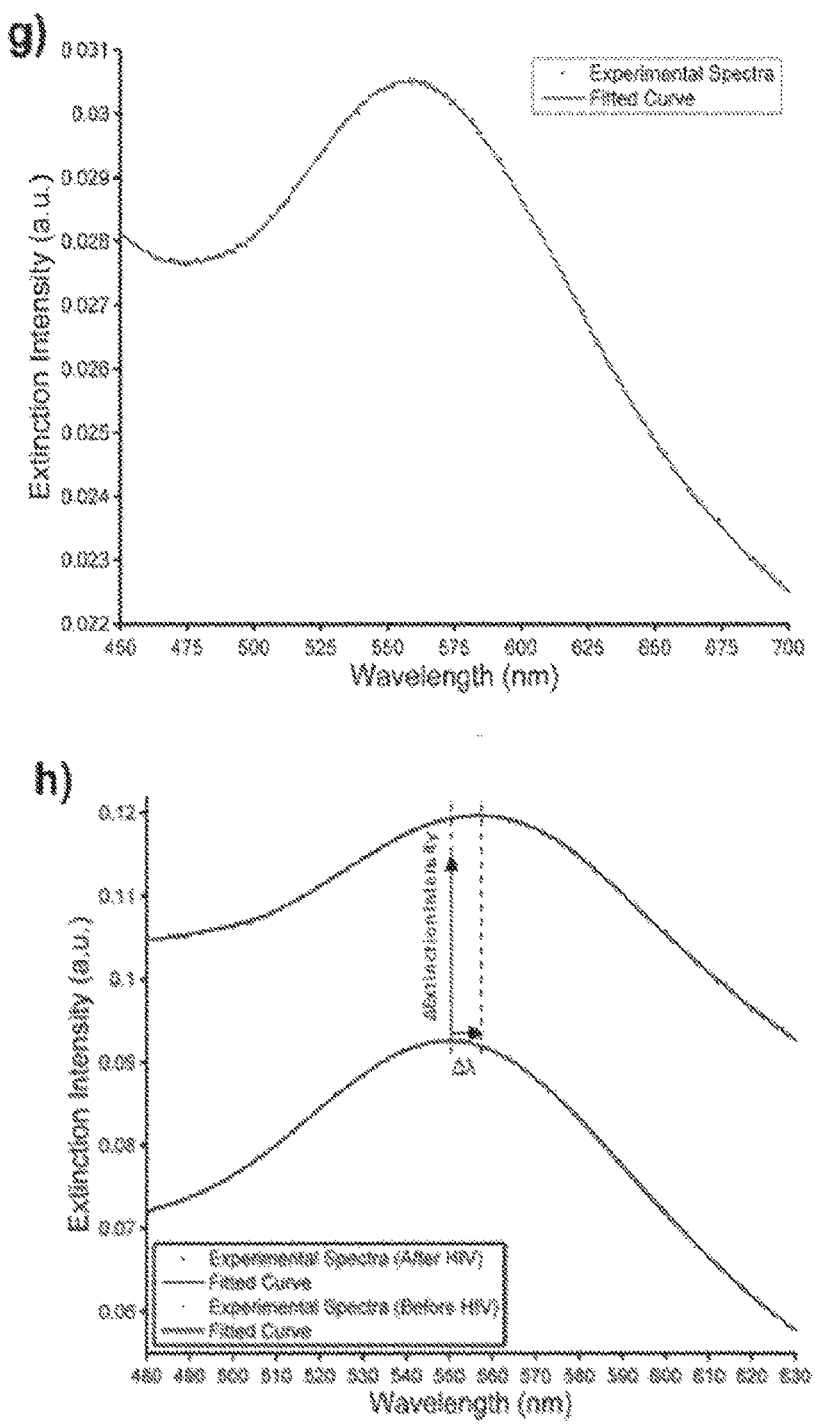

Looking at FIG. 3A, each modification was analyzed using curve fitting method. To evaluate the surface chemistry, a control group of unmodified 10 nm diameter gold nanoparticles were utilized. An individual wavelength peak of gold nanoparticles (AuNP) was repeatably observed at 518 nm (n=6, p<0.05) as in FIG. 3A. Gold nanoparticle binding on 0.05 mg/mL of the PLL-modified surface led to a statistically significant peak shift from the gold coated surface from 518 nm to 546.7±1.8 nm (n=6, p<0.05).

As outlined above, following gold nanoparticle coating of the PLL modified surface, MUA was self-assembled as a monolayer onto the gold nanoparticle layer and generated carboxyl groups on the surface of the gold nanoparticle layer.

Antibodies immobilized with a favorable orientation using NeutrAvidin have a higher capture efficiency towards bioagents than those immobilized by physical absorption and chemical binding of antibodies onto a surface. To immobilize biotinylated antibodies for HIV capture, surfaces were modified with NeutrAvidin. At the end of NeutrAvidin modification, a statistically significant wavelength peak shift was observed (4.4±1.1 nm) (n=6, p<0.05).

To prevent non-specific binding, 10% BSA solution was used as a blocking agent. This blocking agent did not result in a statistically significant peak shift (n=6, p>0.05).

Then, biotinylated anti-gp120 polyclonal antibody (Ab) was incubated on the NeutrAvidin-coated surface. The biotinylated anti-gp120 antibody resulted in a statistically significant wavelength peak shift (6.8±0.5 nm) (n=216, p<0.05).

With the assembly of these further layers, it was found that MUA, NeutrAvidin, BSA and Ab collectively shifted the maximum wavelength to 551.9±0.5 nm (n=6-216, p<0.05).

Looking at FIGS. 3B and 3C, to evaluate the repeatability of the surface chemistry, we defined an equation as follows:

$$\text{Repeatability} = \frac{\text{Mean of } WS}{\text{Mean of } WS + SEM} \times 100$$

where WS is wavelength shift, and SEM is the standard error of the mean. In the literature, repeatability is defined as closeness of the agreement between the results of the measurements in the same experiment carried out under the same conditions. Here, repeatability parameter was described as the percent variation in wavelength shift measurements for the surface modifications. The parameter was evaluated for both wavelength and extinction intensity measurements of each surface modification. Overall, the repeatability parameter was observed to be 55-98% and 85-99% for wavelength and extinction intensity measurements, respectively. These results indicated that the surface chemistry presented a reproducible, reliable, accurate, repeatable and feasible nanoplasmonic platform.

To evaluate potential drift and background signal noise due to any potential unexpected chemical/physical changes or nonspecific binding on the surface, we assessed the system using whole blood, HIV-spiked whole blood, and HIV-infected patient samples. The experiments were performed using HIV subtypes A, B, C, D, E, G, panel, and discarded anonymous HIV-infected patient samples.

The difference between control (i.e., whole blood without HIV), HIV-spiked whole blood samples and HIV-infected patient samples was evaluated and is presented in FIGS. 3A and 3D. For control measurements, biosensing surfaces functionalized with NeutrAvidin and polyclonal anti-gp120 antibody were used. The addition of unprocessed whole blood without viruses did not result in a statistically significant peak shift (1.2±1.1 nm, n=6, p>0.05).

As evidenced by the shifts in FIG. 3D, the anti-gp120 polyclonal antibody was observed to reliably and repeatably capture multiple virus subtypes (A, B, C, D, E, G, and panel) using the same platform. Whole blood was spiked with HIV at $(6.5\pm0.6)\times10^5$ copies/mL, $(8.3\pm1.3)\times10^5$ copies/mL, $(1.3\pm0.2)\times10^6$ copies/mL, $(3.8\pm1.2)\times10^6$ copies/mL, $(1.3\pm0.2)\times10^6$ copies/mL, $(1.1\pm0.3)\times10^6$ copies/mL and $(2.9\pm0.5)\times10^6$ copies/mL for subtypes A, B, C, D, E, G, and panel (a mixture of different HIV subtypes), respectively. Statistically significant wavelength shifts were observed of 9.3±1.2 nm, 5.4±1.1 nm, 4.4±0.5 nm, 7.8±1.1 nm, 6.3±0.8 nm, 5.8±0.7 nm and 6.9±1.2 nm for subtypes A, B, C, D, E, G, and panel, respectively (n=6, p<0.05).

To further analyze the experimental data, we constitute curve fitting analyzing method and compared the original experimental data with the cure fitting results (FIG. 4A-G). After the application of HIV to the nanoplasmonic platform, the representative wavelength shift was presented in FIG. 4H.

Statistical assessment on the results was performed using non-parametric Kruskal-Wallis one-way analysis of variance followed by Mann-Whitney U test with Bonferroni correction for multiple comparisons. Statistical significance threshold was set at 0.05, p<0.05. Individual p-values for statistical analyses are presented in Tables 1 and 2 below.

TABLE 1

| Set compared | p-value |
| --- | --- |
| AuNP-PLL | 0.01 |
| PLL-MUA | 0.08 |
| MUA-NA | 0.01 |
| NA-BSA | 0.19 |
| BSA-Ab | 0.01 |
| Ab-Control | 0.33 |

TABLE 2

| Set compared | p-value |
| --- | --- |
| Control - Subtype A | 0.001 |
| Control - Subtype B | 0.001 |
| Control - Subtype C | 0.001 |
| Control - Subtype D | 0.001 |
| Control - Subtype E | 0.001 |
| Control - Subtype G | 0.001 |
| Control - Subtype Panel | 0.001 |

In FIG. 3A, brackets connecting individual groups indicate statistically significant peak shifts. In FIGS. 3A and 3D, error bars represent standard error of the mean.

Example IV

Figure 5:
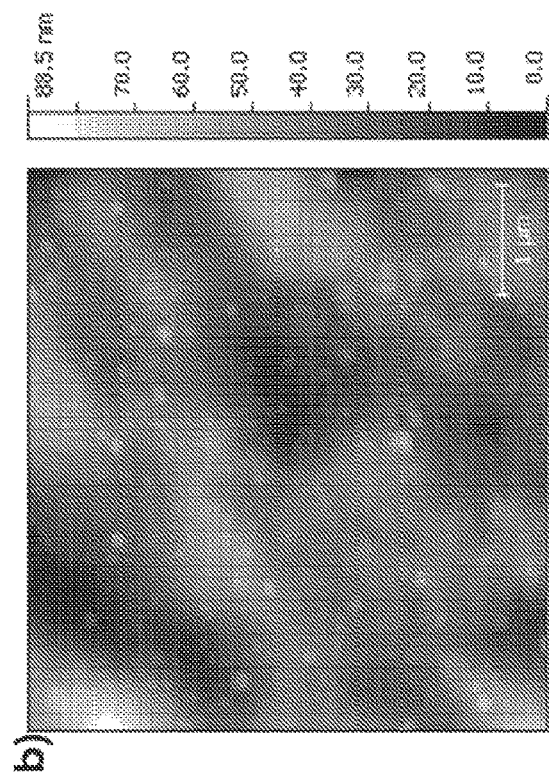
FIGS. 5A through 5D provide surface characterization of PS surfaces before and after surface modification steps using Atomic Force Microscopy (AFM)
FIG. 5E includes two scanning electron microscope images of the captured intact viruses on the antibody immobilized biosensing surface.
Figure 5:
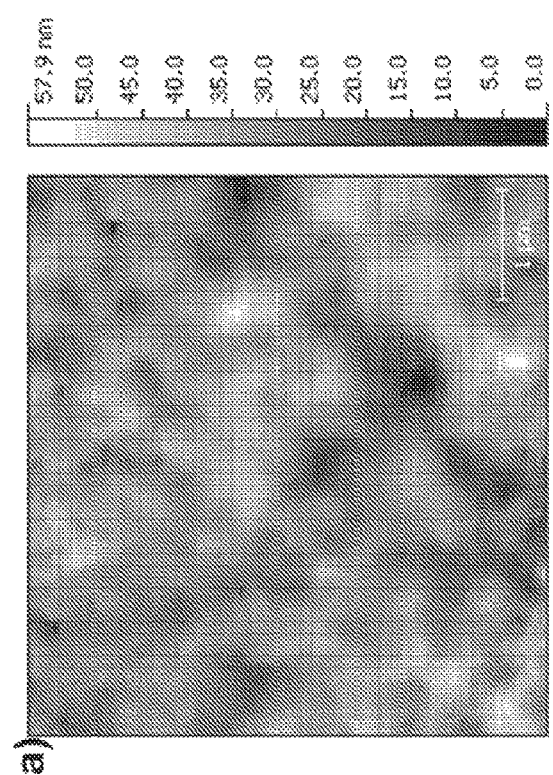
Figure 5:
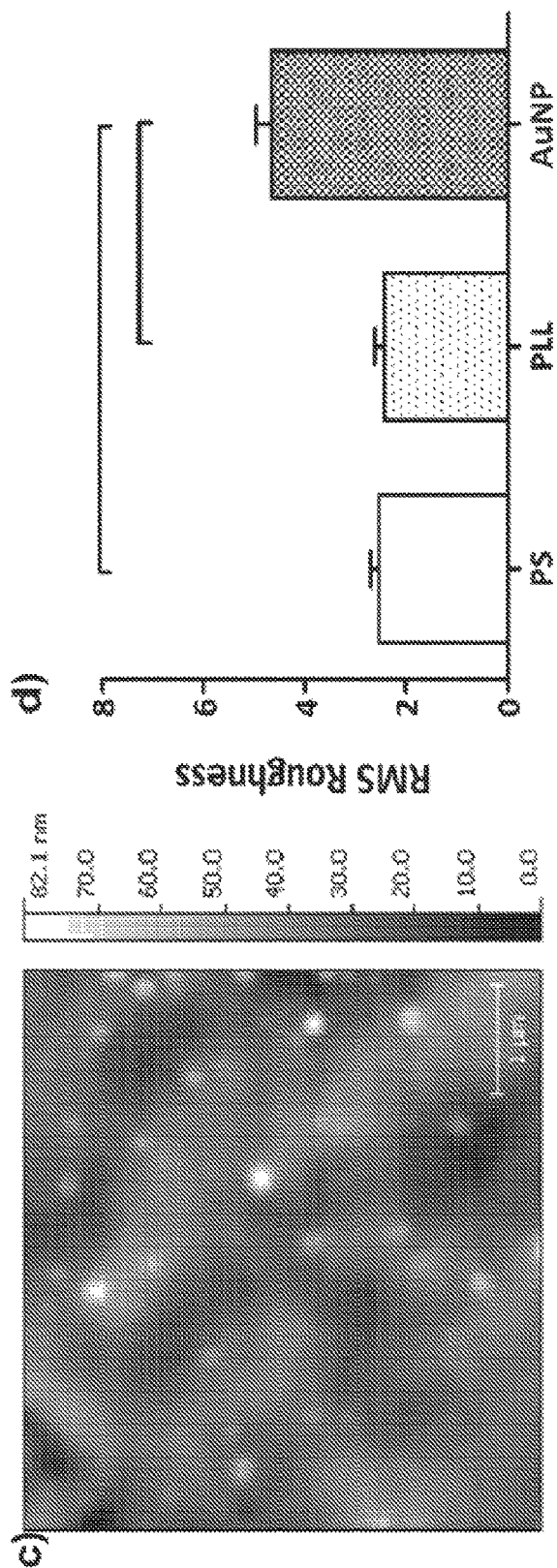
Figure 5:
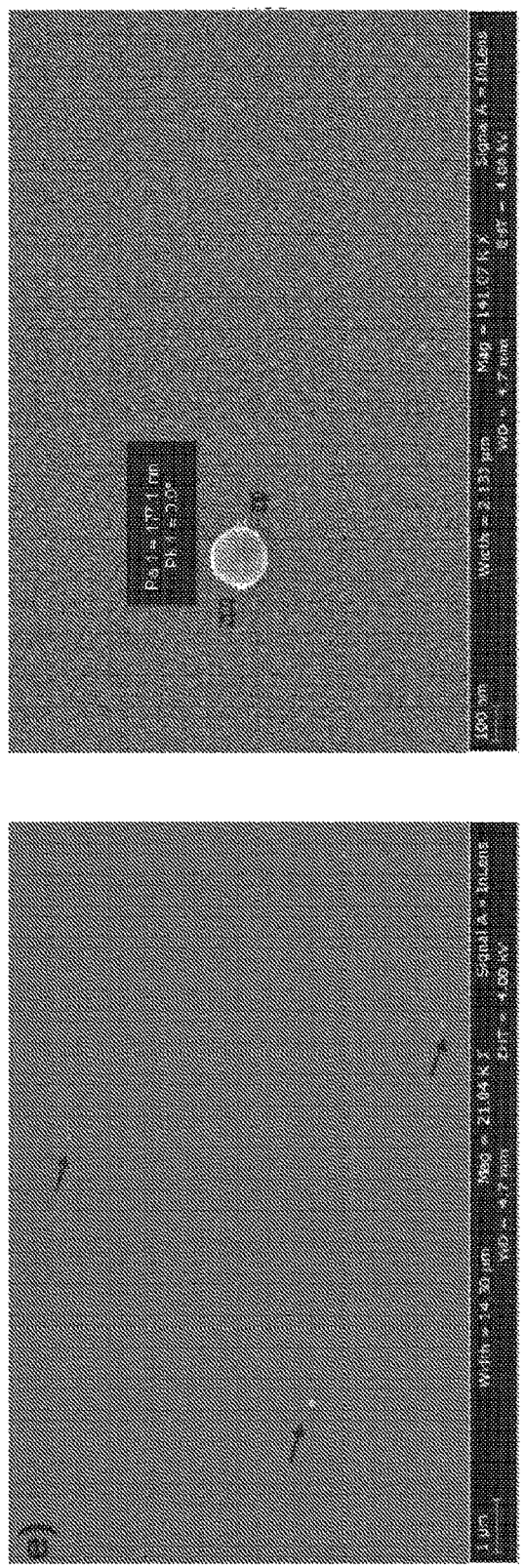

FIGS. 5A through 5C provide surface characterization of polystyrene (PS) substrates before and after surface modification steps using Atomic Force Microscopy (AFM). Five random 5 µm×5 µm surface areas for each sample group were evaluated. FIG. 5A shows a PS substrate without surface modification (that is, before the first coating with PLL). FIG. 5B shows a PS substrate after 0.05 mg/mL of PLL treatment. FIG. 5C shows the surface after gold nanoparticles (AuNPs) was immobilized on poly-l-lysine (PLL) treated surfaces. After AuNP immobilization, nanoparticles were observed on surfaces.

Turning now to FIG. 5D, the root mean square (RMS) roughness of the surfaces was evaluated and significant difference was observed when gold nanoparticles were immobilized onto the surfaces compared to PS substrates with and without PLL (n=8, p<0.05). The surface roughness change was evaluated by Asylum-1 MFP-3D AFM System (Asylum Research Inc., Santa Barbara, Calif.) under tapping mode using a 9±2 nm AFM tip with a scan rate of 0.5 Hz. Five random 5 µm×5 µm areas on the biosensing surfaces were evaluated. On the PS substrate, a roughness of 2.54±0.17 nm expressed as RMS measurements±SEM was measured. After modification of the surface with 0.05 mg/mL of PLL, the RMS roughness value was observed to be 2.43±0.20 nm. Gold nanoparticle immobilization on PLL modified surfaces gave a RMS roughness value of 4.65±0.32 nm.

The results presented in FIG. 5D indicates that there was no statistically significant difference between unmodified and PLL-modified polystyrene surfaces (n=8, p>0.05). However, there was a significant difference between gold nanoparticle immobilization and unmodified polystyrene surfaces (n=8, p<0.05). Hence, gold nanoparticle immobilized surfaces led to significantly greater changes in RMS roughness values compared to PLL modified surfaces (n=8, p<0.05). The statistical analysis results and p-values obtained using non-parametric Kruskal-Wallis one-way analysis of variance followed by Mann-Whitney U test with Bonferroni correction were also presented in Table 3, below.

TABLE 3

| Set compared | p-value |
| --- | --- |
| PS-PLL | 0.83 |
| PS-AuNP | 0.003 |
| PLL-AuNP | 0.003 |

Brackets connecting individual groups in FIG. 5D indicate statistically significant peak shift. Error bars represent standard error of the mean.

To quantitatively evaluate the coating uniformity and density of gold nanoparticles, AFM analysis was performed on the different areas of the modified surfaces. To assess the distribution uniformity of the gold nanoparticles, the following methods were reported using the public domain NIH ImageJ software. The images (5 µm×5 µm) were first converted into 8-bit images using the public domain NIH ImageJ software, and then, the lower and upper thresholds were adjusted to 50 a.u. and 200 a.u., respectively. The uniformity is calculated by utilizing this threshold range, and the immobilization of gold nanoparticles presented ~83% uniform coating on the biosensing surface (n=8). Thus, highly uniform and densely coated nanoplasmonic platform was produced. The modified surfaces were incubated at 4° C., and therefore, the evaporation was prevented. Thus, any coffee ring effects during gold nanoparticle incubation and surface chemistry were not observed.

Gold nanoparticle immobilization and binding on PLL modified surface was also evaluated and it was measured that gold nanoparticles bound sequentially onto the modified surface form active areas of 18.97±1.34 nm in height.

Example V

After antibody immobilization on the biosensing platform, polystyrene surfaces that captured HIV from whole blood was cut by a glass cutter, and then, prepared for Scanning Electron Microscopy (SEM) imaging.

Evidence of the reliable capture of HIV particles was shown using a Scanning Electron Microscopy (SEM) in FIG. 5E. On the left side of FIG. 5E, a scanning electron microscope image of the captured intact viruses were presented on the antibody immobilized biosensing surface is presented denoted by arrows. On the right side of FIG. 5E, higher magnification of a captured HIV was imaged and virus diameter was measured as 177.1 nm. The SEM images were taken at 4.7 mm working distance and 4.00 kV accelerating voltage.

The SEM images of captured viruses at multiple locations on chip did not show any aggregation of captured viruses. During testing of whole blood samples, the aggregation of viral particles was not observed and this is further supported by repeatability of the capture efficiencies with clinical discarded anonymous HIV-infected patient samples.

Coating uniformity and density of gold nanoparticles on PLL modified surfaces were also qualitatively evaluated using SEM. The results obtained by SEM qualitatively supported the AFM results, and SEM experiments demonstrated that gold nanoparticles uniformly distributed on the surface.

Example VI

Biological environment of viruses provide several potential challenging factors including excessive level of albumin, casein, immunoglobin, and other proteins, which might cause blocking of the antigen-antibody interaction and non-specific binding. This could increase nonspecific background signals and interfere with the system performance. Hence, directly detecting viruses from biological samples is a crucial test to evaluate the biosensing performance and robustness of the system.

To evaluate the limit-of-detection and broad applicability of the nanoplasmonic detection platform in biologically relevant systems, various concentrations of multiple subtypes were analyzed spiked in whole blood and phosphate buffered saline (PBS). The results of PBS are presented separately below in a different example. In this Example, the results of multiple HIV subtypes, i.e., A, B, C, D, E, G, and panel, spiked in whole blood are presented. For each sample, the number of HIV copies/mL for each sample was quantified using by reverse transcription-quantitative polymerase chain reaction (RT-qPCR) and sampling and this viral load was compared to the observed change in wavelength and/or extinction intensity when the sample was placed on the nanoplasmonic detection platform. Establishing a clear correlation between the viral load detected by the RT-qPCR, which is known to provide accurate viral counts, and the observed change in wavelength and/or extinction intensity detected when a platform carrying the sample is measured would strongly suggest that measuring the change in wavelength and/or extinction intensity of the sample could be used as a proxy for measurement of the viral load on the sample, assuming sufficient sensitivity.

HIV-1 subtypes A, B, C, D, E, G, and a panel subtype, which consists of 6 major globally prevalent strains of genetically and biologically characterized HIV-1 isolates (A, B, C, D, and circulating recombinant forms (CRF01_AE and CRF02_AG)), were obtained from National Institutes of Health (NIH) under AIDS Research and Reference Reagent Program. The catalog number of panel is 11259 at NIH AIDS Research and Reference Reagent Program. Patient samples were obtained from Massachusetts General Hospital, Boston, Mass. All spiked and patient samples were tested with the detection platform. These subtypes were collected from clinical samples in the United States and Uganda, and cultured in peripheral blood mononuclear cells (PBMCs) using a standard co-culture protocol. Briefly, HIV-1 negative PBMCs were first extracted using Ficoll Hypaque density gradient centrifugation (Histopaque 1077 Sigma H8889). After 3-day phytohemagglutinin (PHA) stimulation (0.25 µg/mL), HIV-1 negative PBMCs were co-cultured with HIV-1 infected PBMCs in R20/IL-2 (100 U/mL), which consists of RPMI-1640 (Cellgro® Mediatech 10-040-CV) implemented with L-Glutamine (300 mg/mL), 20% heat inactivated fetal bovine serum (FBS; Gemini), penicillin (50 U/mL), streptomycin (50 µg/mL), HEPES buffer (10 mM), and recombinant human interleukin-2 (100 U/mL, Roche). The culture was incubated under humidified 5% $CO_2$ atmosphere at 37° C., and culture supernatants were replaced bi-weekly with fresh medium. 3-day PHA stimulated HIV-1 infected PBMCs were added once a week, and supernatants were collected for p24 testing (Perkin Elmer®, NEK050b). Culture termination was determined by p24 levels (at least 20 ng/mL) in cell-free supernatant, and virus supernatants were stored at −80° C. for the quantification and sampling assays.

In order to quantify the HIV subtypes by RT-qPCR and sampling, multiple HIV subtypes (A, B, C, D, E, G, and panel) were performed in biosafety level (BSL)2+ laboratories, and the biosensing platform was evaluated in BSL2+ laboratories after HIV sample was fixed with a paraformaldehyde-containing solution.

To spike HIV in whole blood, HIV subtypes were first quantified by RT-qPCR (Roche COBAS®, Branchburg, N.J.). The samples with a cycle threshold (CT) value greater than that of the lowest standard point (50 copies/mL), which had a CT value of 30-40 (50 PCR cycles were run in total). The low copies of HIV viral load were earlier reported using reverse transcription-quantitative polymerase chain reaction (RT-qPCR) systems. Any sample with a positive signal, but with a cycle threshold (CT) value higher than that of the lowest standard point, was reported with a viral load value of less than 50 copies/mL.

We measured HIV concentrations of $6.55 \times 10^8$, $6.37 \times 10^8$, $2.09 \times 10^9$, $7 \times 10^8$, $8.39 \times 10^8$, $6.53 \times 10^8$ and $1.48 \times 10^9$ copies/mL for subtypes A, B, C, D, E, G and panel (a mixture of different HIV subtypes), respectively. Panel consists of HIV subtype A, B, C, D, and circulating recombinant forms (CRF01_AE and CRF02_AG). For HIV stock sample quantification, viruses were lysed using guanidine isothiocyanate provided in the QIAamp Viral RNA Mini Kit (Qiagen, Valencia, Calif.), and then HIV RNA was extracted according to manufacturer's instructions.

To quantify HIV RNA, RT-qPCR was performed. For reverse transcription of HIV RNA samples, 10 µL of 2× core RT buffer, 2 µL of 10 µM of reverse primer (5'-GTCT-GAGGGATCTCTCTAGTTACCAG-3'), 0.5 µL of Affinity-Script (Applied Biosystems, Carlsbad, Calif.), and 7.5 µL of HIV RNA were used and performed on GeneAmp PCR System 9700 (Applied Biosystems, Carlsbad, Calif.). The reaction was set up to 25° C. for 5 minute, 45° C. for 60 minute and 95° C. for 3 minute incubation. For quantification of RNA, 50 µL of the master mixture was applied. Master mixture includes 1× core PCR buffer, 0.4 µM of forward primer LTR-F (5'-TAAAGCTTGCCTTGAGT-GCT-3'), reverse primer LTR-R2, 0.2 µM of TaqMan probe LTR-P (5'-AGTAGTGTGTGCCCGTCTGTTGTGTG-3'), 2.5 units of SureStart Taq polymerase, and 10 µL of cDNA template. For the amplification step, 7300 Real-Time PCR System (Applied Biosystems, Carlsbad, Calif.) was first set up to 25° C. for 5 minutes and 95° C. for 10 minutes, and then, 50 cycles of 60° C. for a minute, and 95° C. for 30 seconds were performed. The viral load values were obtained by RT-qPCR and repeated at least 3 times each sample for each concentration.

Following the viral load quantification and comparison, HIV stock solutions of A, B, C, D, E, G, and panel subtypes were spiked into unprocessed whole blood for the final concentration varying from 50 copies/mL to $1 \times 10^6$ copies/mL. 100 µL of HIV spiked whole blood was loaded into each antibody immobilized surface of the nanoplasmonic platform and incubated at 4° C. for an hour. Whole blood samples without HIV spiking were used as controls. A second set of RT-qPCR was performed to minimize dilution inaccuracies. The same quantification protocol was utilized for discarded HIV patient samples.

Before HIV detection using LSPR, bound viruses were immobilized by a fixation solution containing paraformaldehyde and incubated at 4° C. for an hour. Following each surface modification step, surfaces were rinsed with 1×PBS three times to remove blood cells. Since the lowest detection limit of RT-qPCR was set to 50 copies/mL, the average of the multiple PCR results that is below 50 copies/mL were reported as ~50 copies/mL; (e.g., 22±20 copies/mL in HIV subtype A, 44±11 copies/mL in HIV subtype C and 57±17 copies/mL in HIV subtype E) and plotted with the original data point in the wavelength and extinction intensity shift figures for curve fitting and/or experimental data maximum methods.

Figure 6:
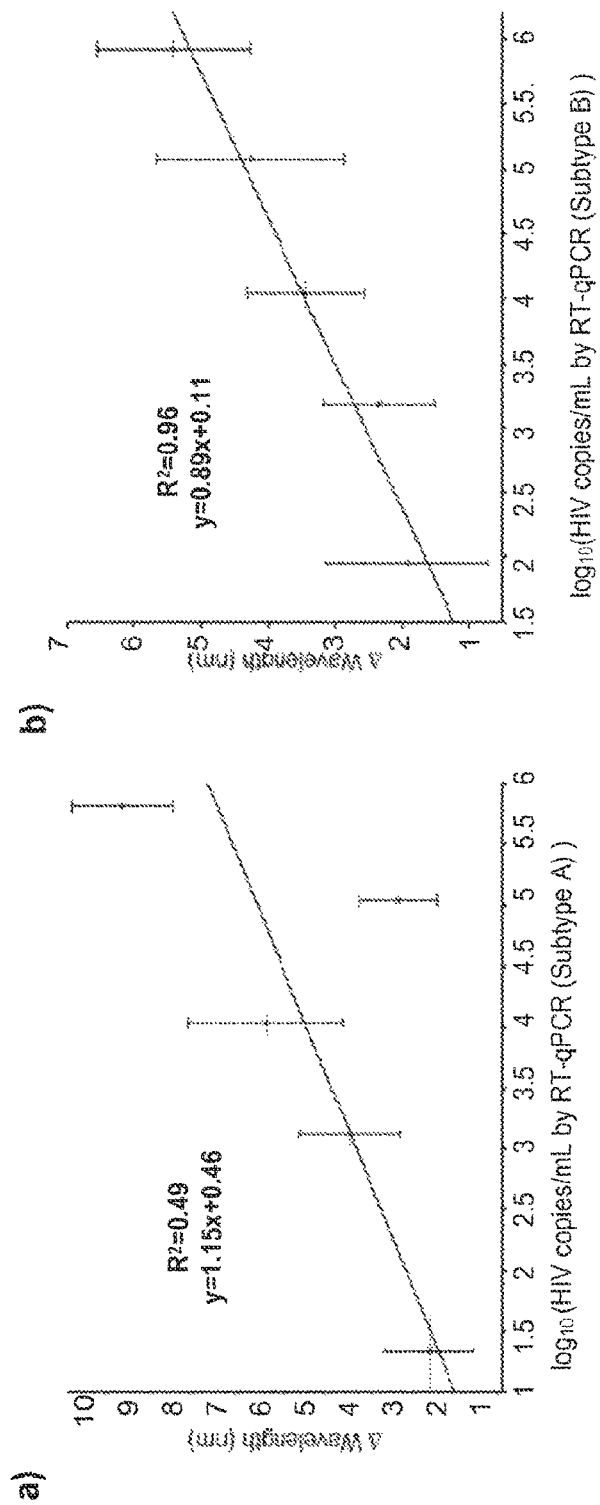
FIGS. 6A through 6H provide validation of the nanoplasmonic platform with spiked in whole blood using curve fitting method and HIV-infected patient samples using RT-qPCR by comparing a detected change in wavelength to the viral load detected by RT-qPCR.
FIG. 6I illustrates the repeatability parameter for HIV spiked in whole blood and HIV-infected patient samples in terms of wavelength change.
Figure 6:
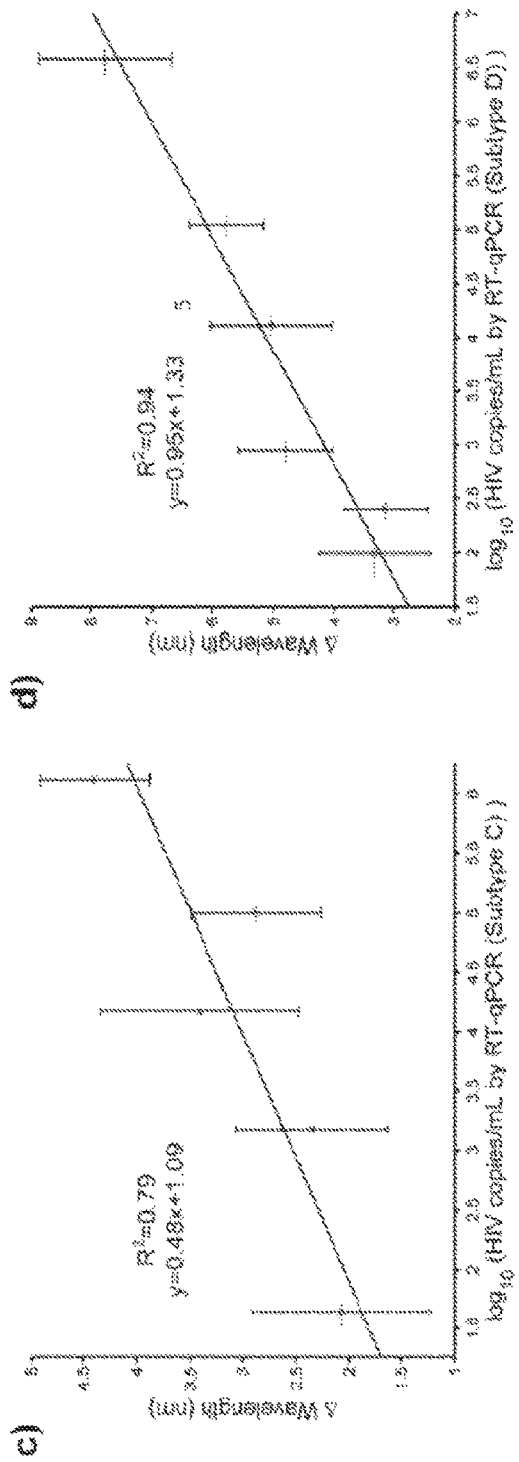
Figure 6:
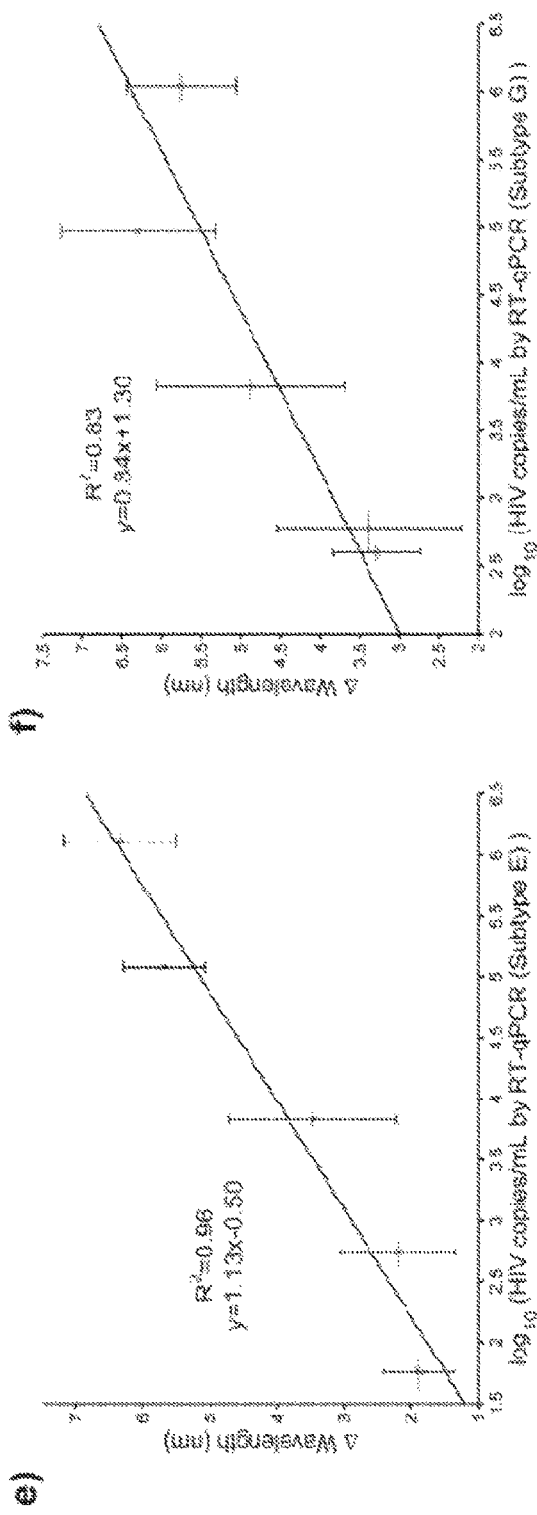
Figure 6:
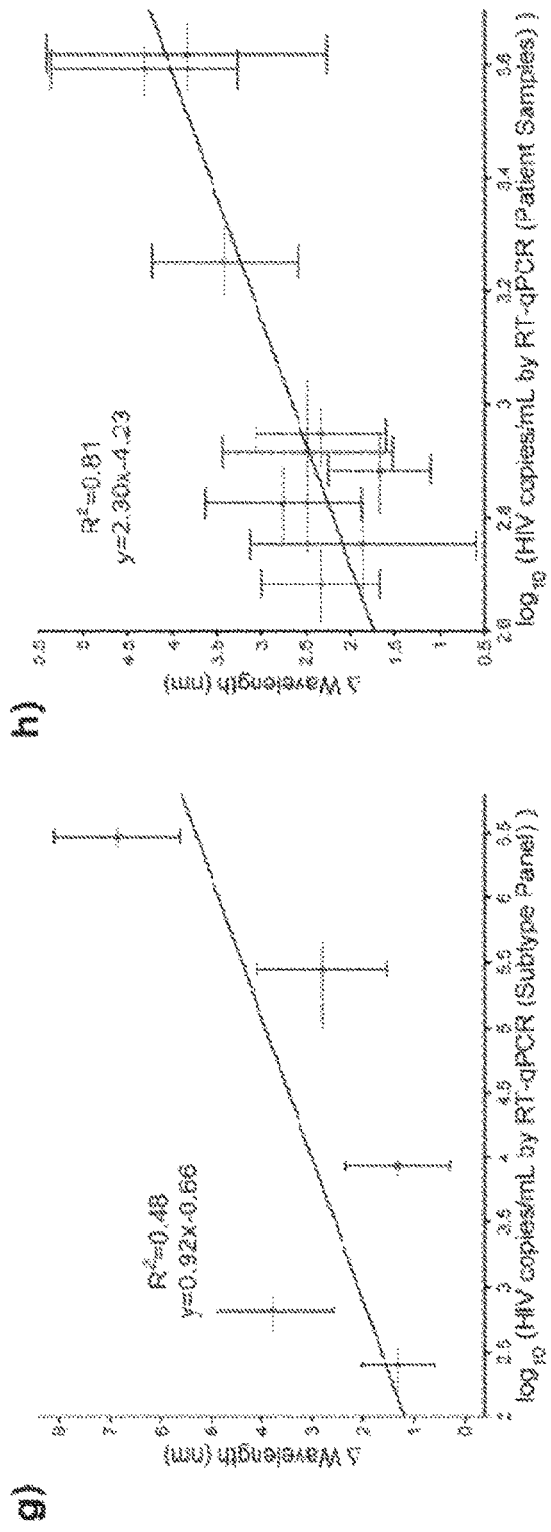
Figure 6:
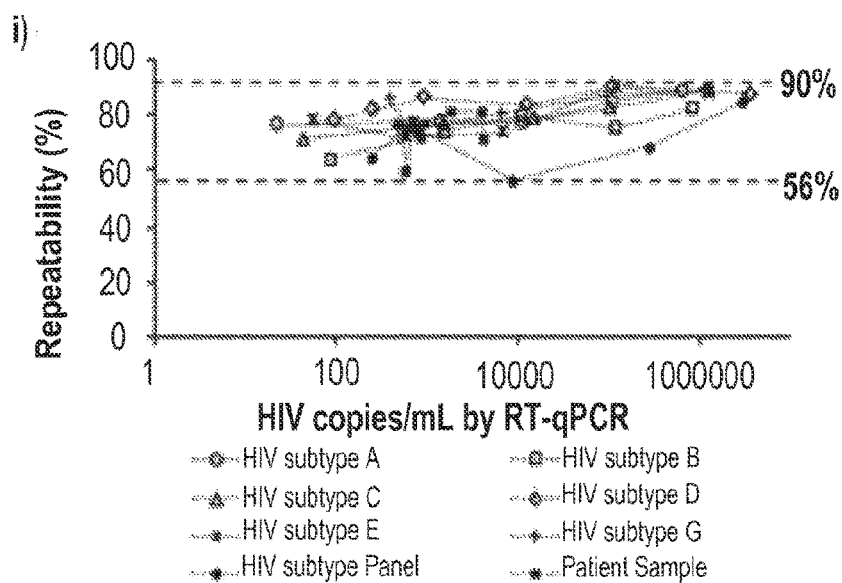

As shown in FIG. 6A, in the presence of HIV subtype A, the highest peak shift was observed at 9.3±1.2 nm at $(6.5\pm0.6)\times10^5$ copies/mL. The detected peak shift decreased with decreasing viral concentration. For instance, down to 50 copies/mL HIV viral load resulted in a change of 2.9 nm±0.9 nm.

As shown in FIG. 6B, in the presence of HIV subtype B, the highest $((8.3\pm1.3)\times10^5$ copies/mL) and lowest (89±6 copies/mL) concentrations of HIV viral load resulted in 5.4±1.1 nm and 1.9±1.2 nm peak shifts, respectively.

In FIG. 6C, HIV subtype C spiked in blood samples displayed a peak shift of 4.4±0.5 nm at $(1.3\pm0.2)\times10^6$ copies/mL concentration, and 2.1±0.8 nm shift at ~50 copies/mL concentration.

As illustrated in FIG. 6D, in the presence of HIV subtype D, the wavelength shifted by 7.8±1.1 nm at $(3.8\pm1.2)\times10^6$ copies/mL concentration, and by 3.3±0.9 nm at 98±39 copies/mL concentration.

FIG. 6E shows that HIV subtype E spiked in blood samples displayed a peak shift of 6.3±0.8 nm at $(1.3\pm0.2)\times10^6$ copies/mL concentration, and 1.9±0.5 nm shift at ~50 copies/mL concentration.

FIG. 6F provides the collected data for HIV subtype G. In the presence of HIV subtype G, the highest peak shift was observed to be 5.8±0.7 nm at (1.1±0.3)×10⁶ copies/mL. The peak shift for 404±54 copies/mL HIV viral load was 3.3 nm±0.6 nm.

FIG. 6G shows that in the presence of HIV subtype panel, the highest peak shift was observed to be 6.9±1.2 nm at (2.9±0.5)×10⁶ copies/mL. The peak shift for 245±101 copies/mL HIV viral load was 1.3±0.7 nm.

Figure 7:
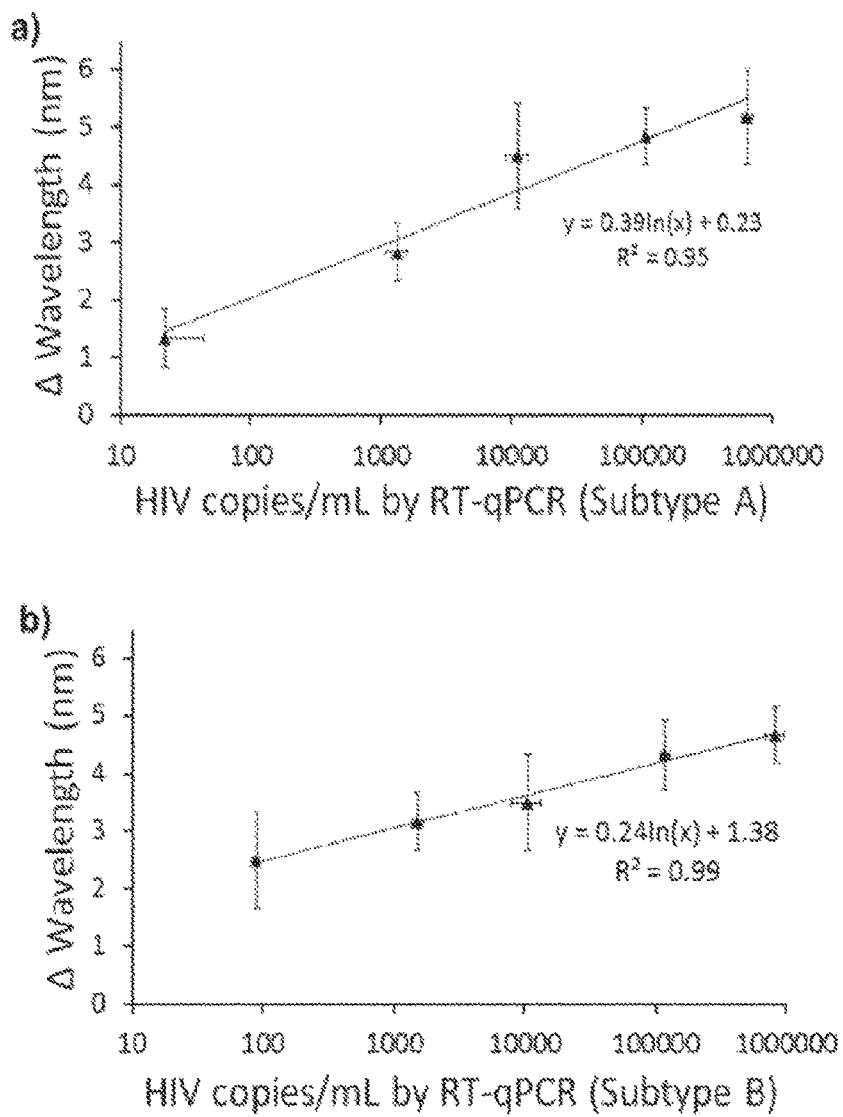
FIGS. 7A through 7H provide validation of the nanoplasmonic platform with spiked in whole blood using experimental data maximum method and HIV-infected patient samples using RT-qPCR by comparing a detected change in wavelength to the viral load detected by RT-qPCR.
FIG. 7I illustrates the repeatability parameter for HIV spiked in whole blood and HIV-infected patient samples in terms of wavelength change.
Figure 7:
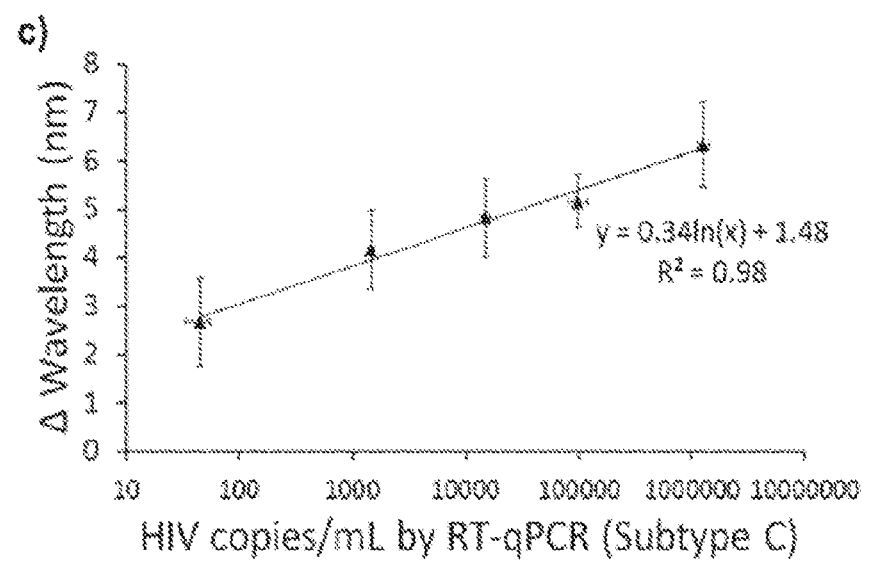
Figure 7:
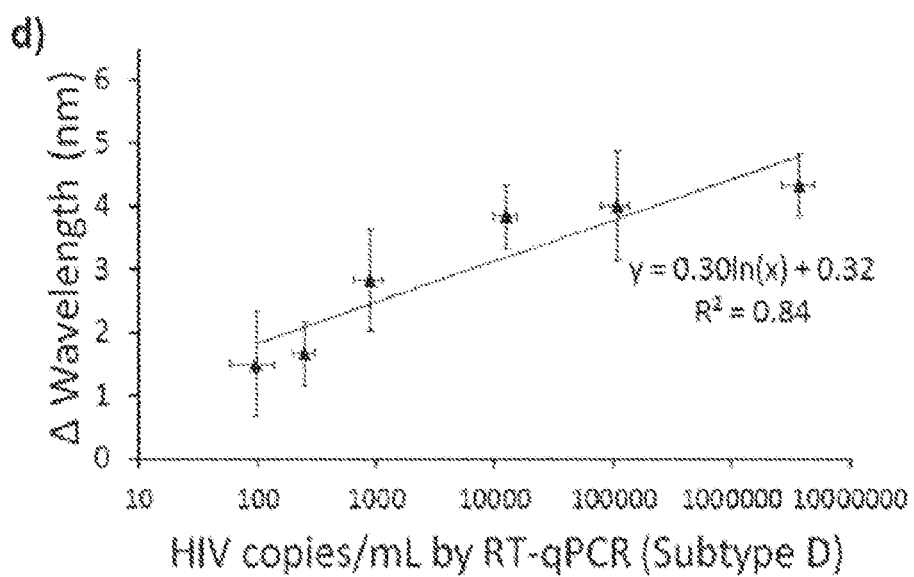
Figure 7:
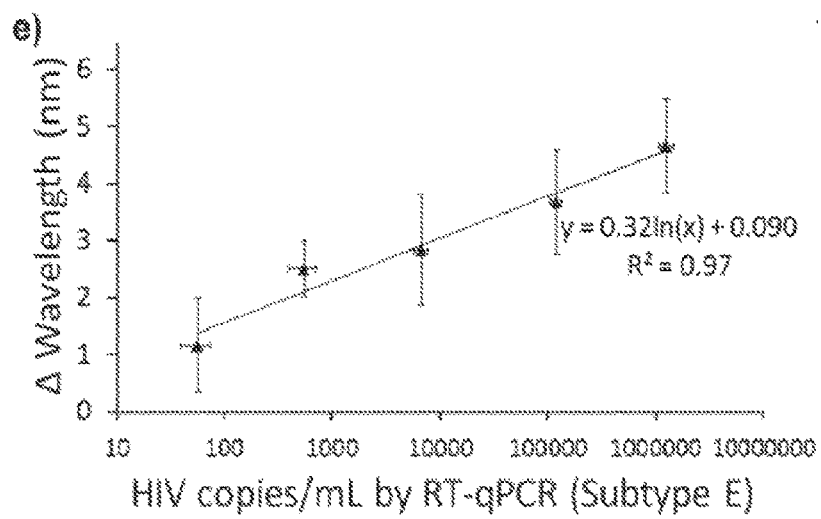
Figure 7:
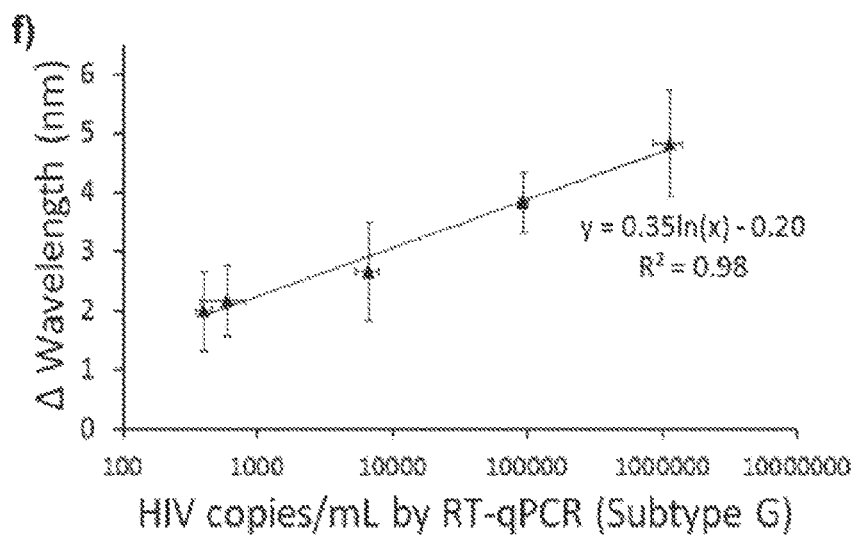
Figure 7:
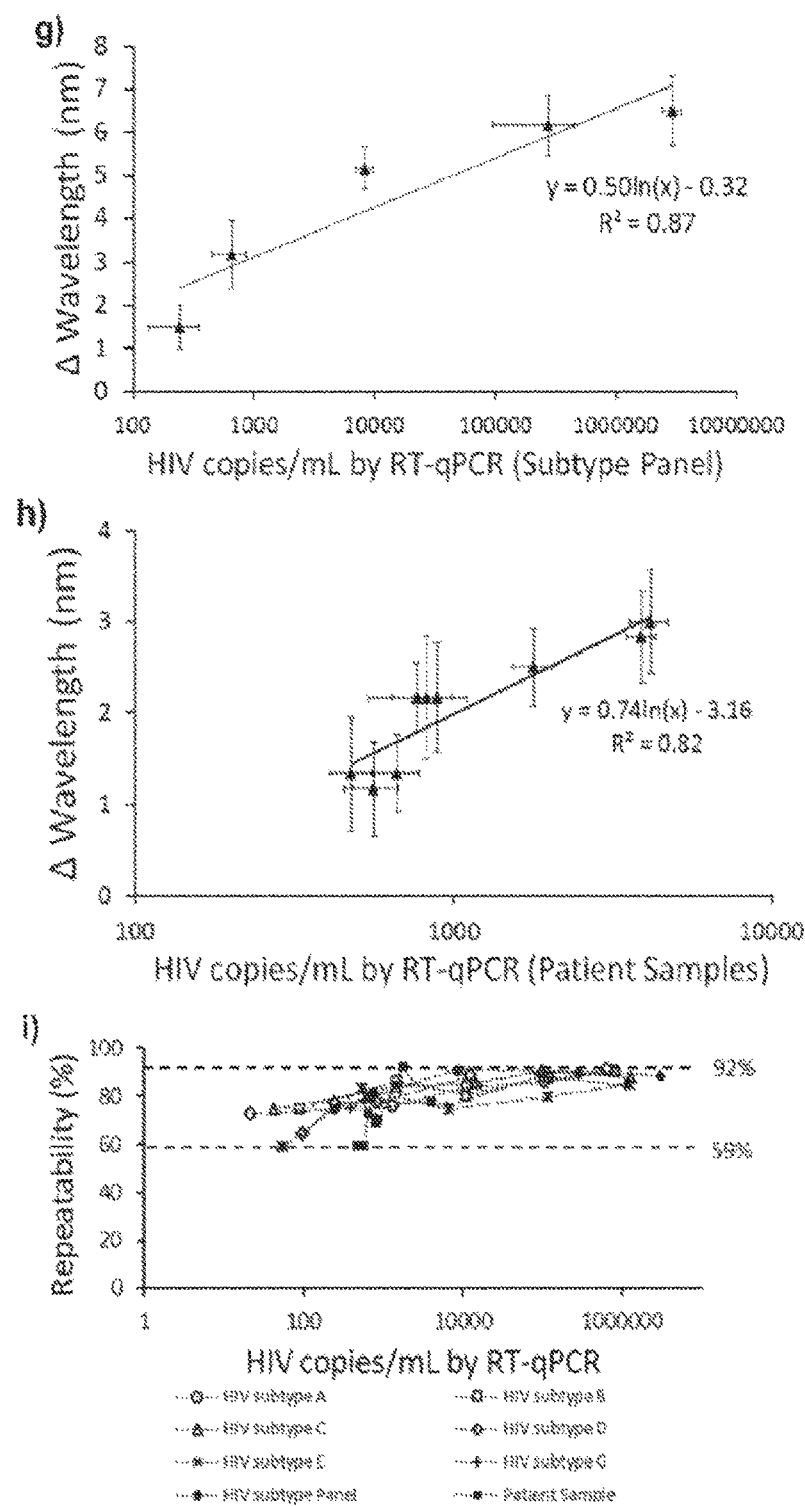

The HIV viral load was validated 8 HIV-infected anonymous discarded patient whole blood samples using the nanoplasmonic platform. The discarded HIV patient samples in whole blood were evaluated and it was observed that there was 4.3±1.0 nm at 3910±400 copies/mL. The peak shift decreased to 2.3±0.7 nm when the lowest concentration (481±73 copies/mL) sample was evaluated. These curve fitting results correlate with the experimental data maximum method shown in FIG. 7. Thus, in this work we used the curve fitting method in the analysis, using the experimental data maximum method to confirm this method.

Here, we analyzed a total of 216 data points for the HIV spiked whole blood and other 216 data points for their corresponding antibody references. Each data point was subtracted from its own reference. 9 wells out of the 216 reference measurements were more than 1 SEM away from the mean. Also, the measurements with these wells gave negative results indicating that these wells had issues with the basic surface chemistry and thus they were eliminated from the analysis. Another 4 wells gave negative results below −1 nm when the HIV-spiked whole blood curves were subtracted from the antibody reference of the same well. These wells were not included in the analysis, since these results are inconclusive and potentially due to the variations in the surface chemistry. Additionally, one well gave a very large shift among the 50 copies/mL and 100 copies/mL wells (larger than the same subtype's highest concentration's shift plus its SEM) so it is not included. The 10 negative shifts observed ranging between 0 and −0.5 nm, which are below the instrumental step size (1 nm) are equivalent to a no-shift. These may be due to the fact that no viruses were captured in the active area hence these data points were included in the analysis to reflect the statistical nature of the capture event.

Additionally, the nanoplasmonic extinction spectra of a nanoparticle can be affected by neighboring nanoparticles. This property has been used in measuring the length of flexible single-strand DNA strains positioned in between nanoparticle pairs. It has been shown that short inter-particle distances can amplify the local electromagnetic fields causing an increased LSPR signal. These enhanced fields (hotspots) have been recently used in nanoplasmonic detection of Adenovirus particles. The exact nature of this enhancement is reported to be a function of the nanoparticle arrangement on the surface and the effective refractive index distribution over nanoparticles.

Example VII

As a second analyzing method, the experimental data maximum was used. In the presence of HIV subtype A, the highest peak shift was observed at 5.2±0.5 nm at (6.5±0.6)×10⁵ copies/mL (FIG. 7A). The detected peak shift decreased with decreasing viral concentration. For instance, down to 50 copies/mL HIV viral load resulted in a change of 1.3±0.5 nm (FIG. 7A). In the presence of HIV subtype B, the highest ((8.3±1.3)×10⁵ copies/mL) and lowest (89±6 copies/mL) concentrations of HIV viral load resulted in 4.7±0.5 nm and 2.5±0.8 nm peak shifts, respectively (FIG. 7B). HIV subtype C spiked in blood samples displayed a peak shift of 6.3±0.9 nm at (1.3±0.2)×10⁶ copies/mL concentration, and 2.7±0.9 nm shift at ~50 copies/mL concentration (FIG. 7C). In the presence of HIV subtype D, the wavelength shifted by 4.3±0.5 nm at (3.8±1.2)×10⁶ copies/mL concentration, and by 1.7±0.5 nm at 98±39 copies/mL concentration (FIG. 7D). HIV subtype E spiked in blood samples displayed a peak shift of 4.7±0.8 nm at (1.3±0.2)×10⁶ copies/mL concentration, and 1.2±0.8 nm shift at ~50 copies/mL concentration (FIG. 7E). In the presence of HIV subtype G, the highest peak shift was observed to be 4.8±0.9 nm at (1.1±0.3)×10⁶ copies/mL (FIG. 7F). The peak shift for 404±54 copies/mL HIV viral load was 2.0±0.7 nm (FIG. 7F). In the presence of HIV subtype panel, the highest peak shift was observed to be 6.5±0.8 nm at (2.9±0.5)×10⁶ copies/mL (FIG. 7G). The peak shift for 245±101 copies/mL HIV viral load was 1.5±0.5 nm (FIG. 7G). We also validated HIV viral load using 9 HIV-infected anonymous discarded patient whole blood samples using the nanoplasmonic platform. In the presence of discarded patient samples, the highest peak shift was observed to be 3.0±0.6 nm at 4169±578 copies/mL (FIG. 7H). The peak shift for 481±73 copies/mL HIV viral load was 1.3±0.6 nm (FIG. 7H).

Figure 8:
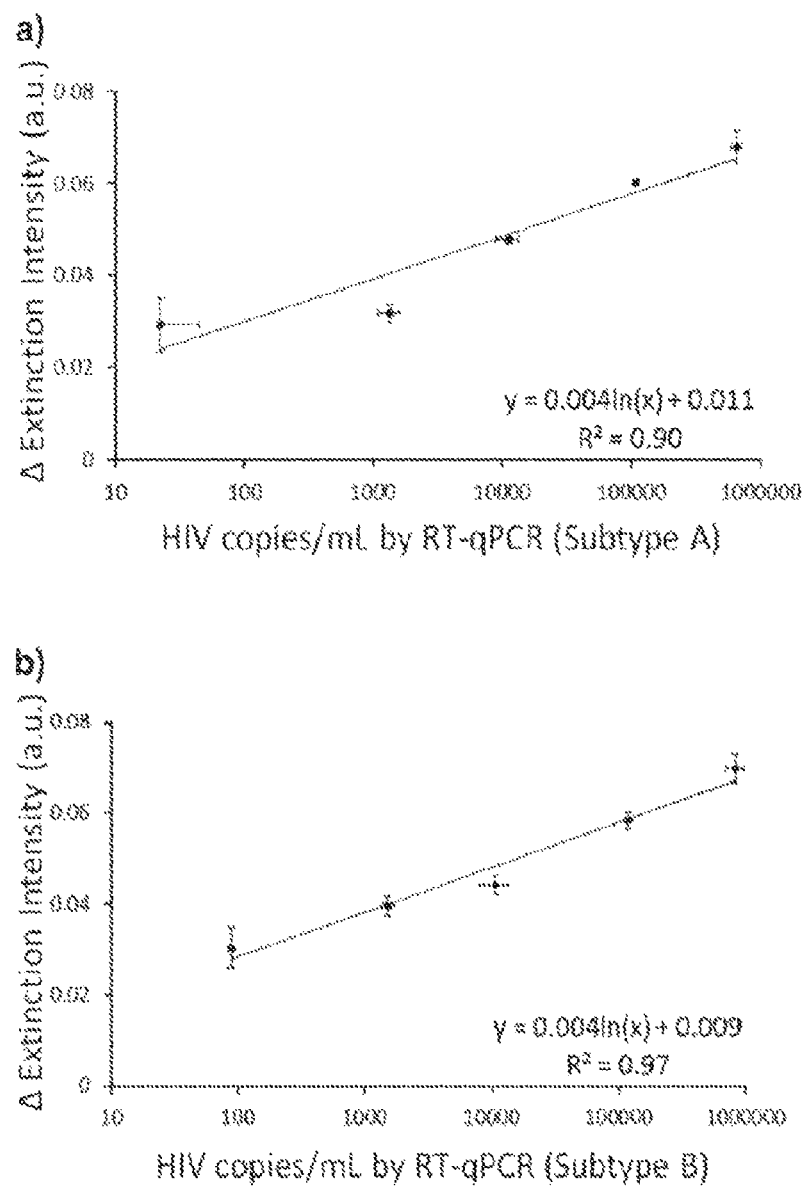
FIGS. 8A through 8H provide validation of the nanoplasmonic platform with spiked in whole blood and HIV-infected patient samples using RT-qPCR by comparing a detected change in extinction intensity to the viral load detected by RT-qPCR.
FIG. 8I illustrates the repeatability parameter for HIV spiked in whole blood and HIV-infected patient samples in terms of extinction intensity change.
Figure 8:
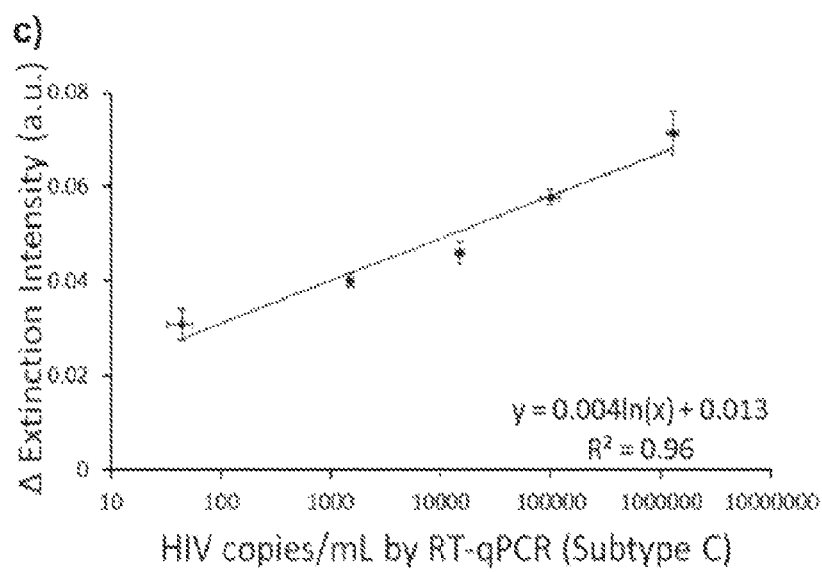
Figure 8:
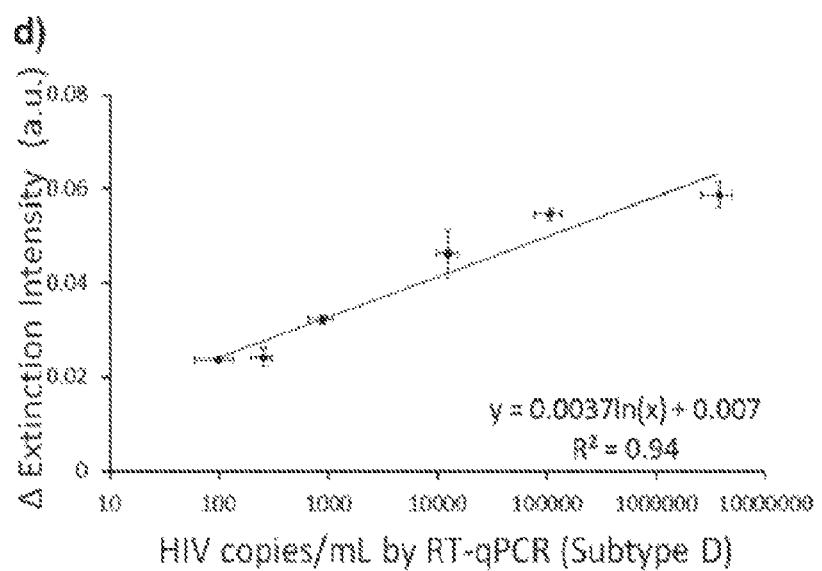
Figure 8:
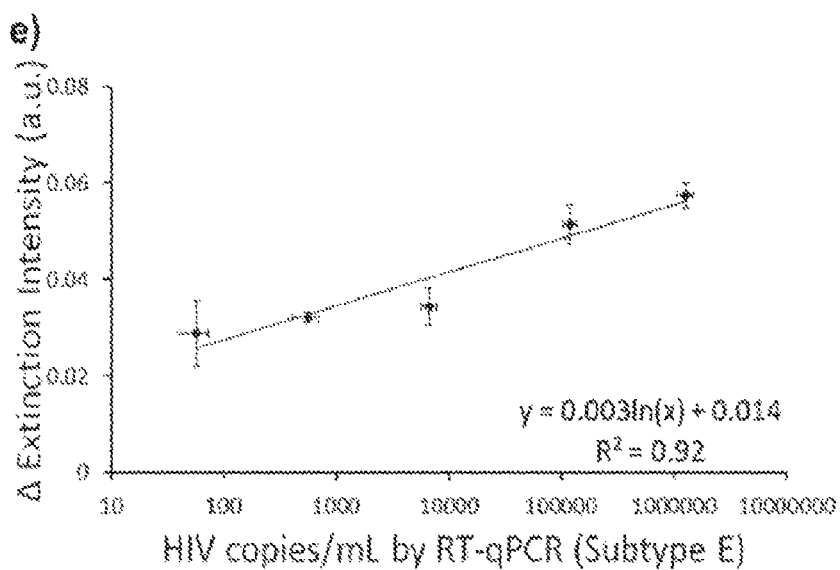
Figure 8:
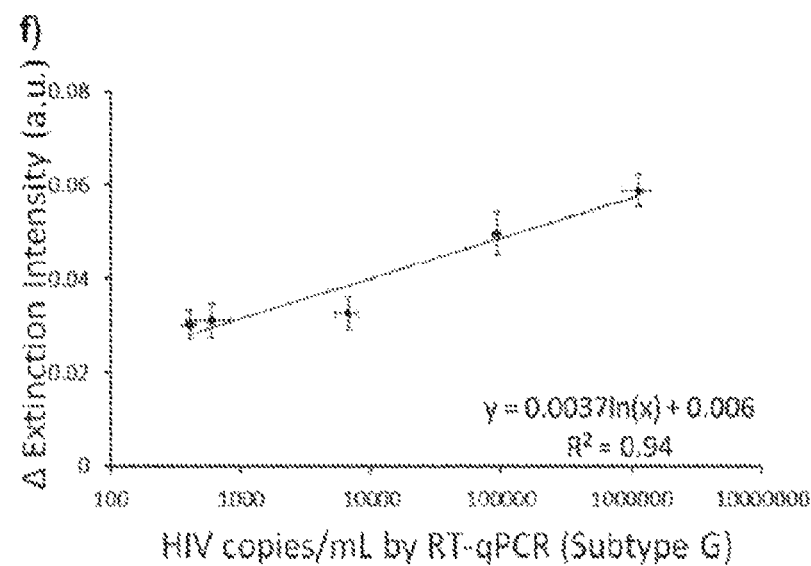
Figure 8:
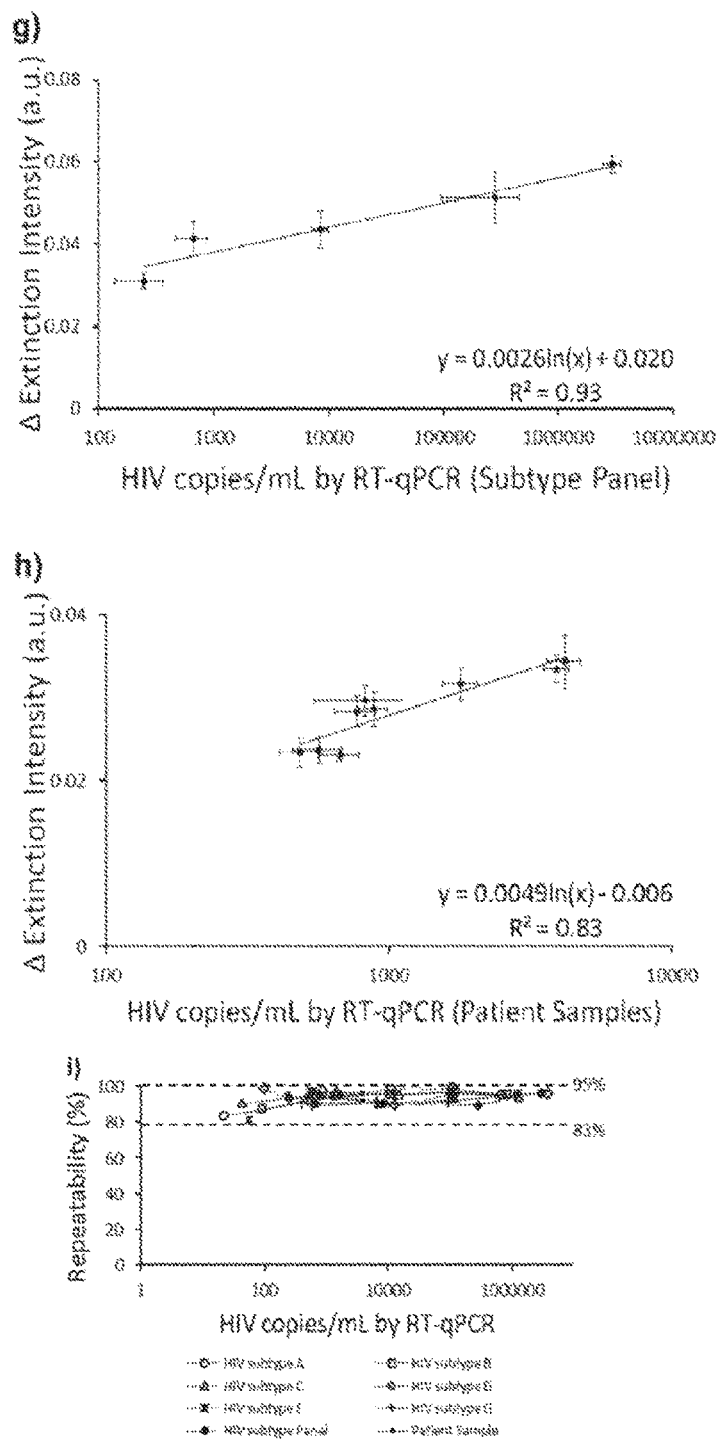

In addition to the wavelength shift, the nanoplasmonic platform can be used to measure extinction intensity variations caused by HIV capture and detection events. The capture events cause both wavelength shift and extinction intensity variation, and the results were acquired both as wavelength shifts and extinction intensity variations. The extinction intensity variations producing the reported detection capability were evaluated for the same set of experiments as in the wavelength shift plots of FIGS. 7A through 7G. In FIGS. 8A though 8H, the extinction intensity variations are compared to the viral load detected by RT-qPCR.

In FIG. 8A, HIV subtype A in whole blood led to a 0.068±0.004 a.u. extinction intensity shift at (6.5±0.6)×10⁵ copies/mL. The extinction intensity shift was observed to be 0.029±0.006 a.u. when the lowest concentration (down to 50 copies/mL) sample was used.

In FIG. 8B, (8.3±1.3)×10⁵ copies/mL of HIV subtype B spiked in whole blood samples led to an extinction intensity shift of 0.070±0.003 a.u. The extinction intensity shift decreased to 0.030±0.004 a.u., when 89±6 copies/mL HIV concentration was evaluated.

In FIG. 8C, for sampling with HIV subtype C in whole blood, (1.3±0.2)×10⁶ copies/mL concentration was evaluated and the extinction intensity shift was observed to be 0.071±0.005 a.u. At ~50 copies/mL concentration, 0.031±0.003 a.u. extinction intensity shift was observed.

In FIG. 8D, (3.8±1.2)×10⁶ copies/mL of HIV subtype D in whole blood sample resulted in an extinction intensity shift of 0.059±0.003 a.u. At a low concentration (98±39 copies/mL), 0.024±0.003 a.u. extinction intensity shift was observed.

In FIG. 8E, HIV subtype E in whole blood was evaluated and it was observed that there was 0.057±0.003 a.u. extinction intensity shift at (1.3±0.2)×10⁶ copies/mL. The extinction intensity shift decreased to 0.029±0.007 a.u. when the lowest concentration (~50 copies/mL) sample was used.

In FIG. 8F, for sampling with HIV subtype G in whole blood, (1.1±0.3)×10⁶ copies/mL concentration was evaluated and the extinction intensity shift was observed to be 0.059±0.003 a.u. At 404±54 copies/mL concentration, 0.030±0.003 a.u. extinction intensity shift was observed.

In FIG. 8G, HIV subtype panel in whole blood was evaluated and it was observed that there was 0.059±0.002 a.u. extinction intensity change at ((2.9±0.5)×10⁶ copies/ mL. The extinction intensity shift decreased to 0.032±0.002 a.u. when the lowest concentration (245±101 copies/mL) sample was used.

In FIG. 8H, discarded HIV patient samples in whole blood were evaluated and it was observed that there was 0.034±0.003 a.u. extinction intensity shift at 4169±578 copies/mL. The extinction intensity shift decreased to 0.023±0.002 a.u. when the lowest concentration (481±73 copies/mL) sample was evaluated.

Example VIII

To evaluate the repeatability of the biosensing platform technology, an equation for a repeatability parameter was defined as follows:

$$\text{Repeatability} = \frac{\text{Sum of } WS \text{ per concentration}}{\text{Sum of } WS \text{ per concentration} + SEM \text{ per concentration}} \times 100$$

where WS is wavelength shift, and SEM is the standard error of the mean. In the literature, repeatability is defined as closeness of the agreement between the results of the measurements in the same experiment carried out under the same conditions. Here, repeatability parameter was described as the percent variation in wavelength shift measurements for the same virus concentration.

The parameter was evaluated for each HIV subtype, and presented at varying spiked sample concentrations. Overall, the repeatability parameter was observed to be 56-90% for a broad range of concentrations for multiple HIV subtypes and discarded HIV patient samples. These results indicated that the nanoplasmonic biosensing platform is reliable, accurate, repeatable and feasible. These results also demonstrated that the system performance was independent of the subtype and concentration, and showed comparable repeatability values for multiple HIV subtypes in whole blood.

The specific repeatability results are as follows for curve fitting analysis. In HIV subtype A spiked samples, the repeatability was observed to be 76-89% at the corresponding concentrations ranging from ~50 copies/mL to $(6.5±0.6)×10^5$ copies/mL. In HIV subtype B spiked samples, the repeatability was observed to be 64-83% at the corresponding concentrations ranging from 89±6 copies/mL to $(8.3±1.3)×10^5$ copies/mL. In HIV subtype C spiked samples, the repeatability was observed to be 71-89% at the corresponding concentrations ranging from ~50 copies/mL to $(1.3±0.2)×10^6$ copies/mL. In HIV subtype D spiked samples, the repeatability was observed to be 78-90% at the corresponding concentrations ranging from 98±39 copies/mL to $(3.8±1.2)×10^6$ copies/mL. In HIV subtype E spiked samples, the repeatability was observed to be 72-90% at the corresponding concentrations ranging from ~50 copies/mL to $(1.3±0.2)×10^6$ copies/mL. In HIV subtype G spiked samples, the repeatability was observed to be 74-89% at the corresponding concentrations ranging from 404±54 copies/mL to $(1.1±0.3)×10^6$ copies/mL. In HIV subtype panel spiked samples, the repeatability was observed to be 56-85% at the corresponding concentrations ranging from 245±101 copies/mL to $(2.9±0.5)×10^6$ copies/mL. In HIV patient samples, the repeatability was observed to be 59-81% at the corresponding concentrations ranging from 481±73 copies/mL to 4169±578 copies/mL.

With reference to FIG. 8I, the repeatability parameter was evaluated for the extinction intensity shifts for multiple HIV subtypes at various concentrations. To do this, the equation above would be modified to replace the sum of wavelength shift per concentration with the sum of the extinction intensity shift per concentration. Overall, the repeatability parameter was observed to be 83-99% for a broad range of concentrations for multiple HIV spiked blood and discarded HIV-infected patient samples. The system performance was independent of the subtype (n=4-6, error bars represent standard error of the mean). The viral load values were obtained by RT-qPCR and repeated at least 3 times each sample for each concentration.

Example IX

Figure 9:
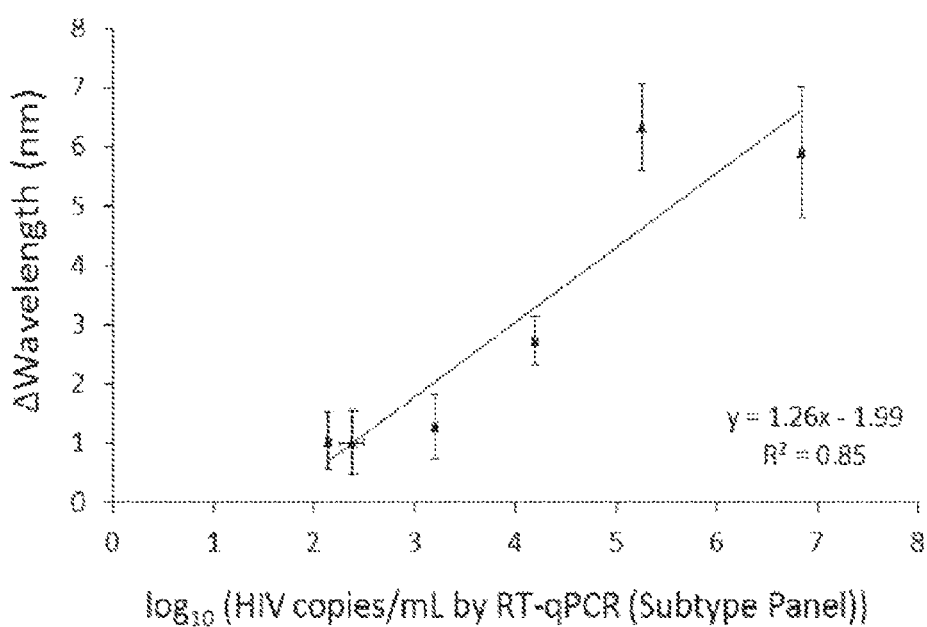
FIG. 9 provides further validation of the nanoplasmonic platform by comparing the detected change in wavelength of a HIV subtype panel suspension in phosphate buffer saline (PBS) with viral loads detected using RT-qPCR.

An HIV subtype panel suspension in phosphate buffered saline (PBS) was also evaluated using SPR and RT-qPCR and the results are reported in FIG. 9. There was 5.9±1.1 nm wavelength shift at $((7±0.4)×10^6$ copies/mL. The peak shift decreased to 1.0±0.5 nm when the lowest concentration (138±10 copies/mL) sample was used (Error bars represent standard error of the mean). We performed 3 replicates for RT-qPCR measurements and 6 replicates for nanoplasmonic measurements for each samples.

Example X

To evaluate quantitative detection, the standard curve with HIV-spiked whole blood samples was obtained, using the wavelength shifts and the HIV viral load obtained by RT-qPCR. After the standard curve was obtained, quantitative detection results using the biosensing platform with HIV-infected patient samples were obtained and are presented in FIGS. 10A and 10B and Table 4.

Figure 10:
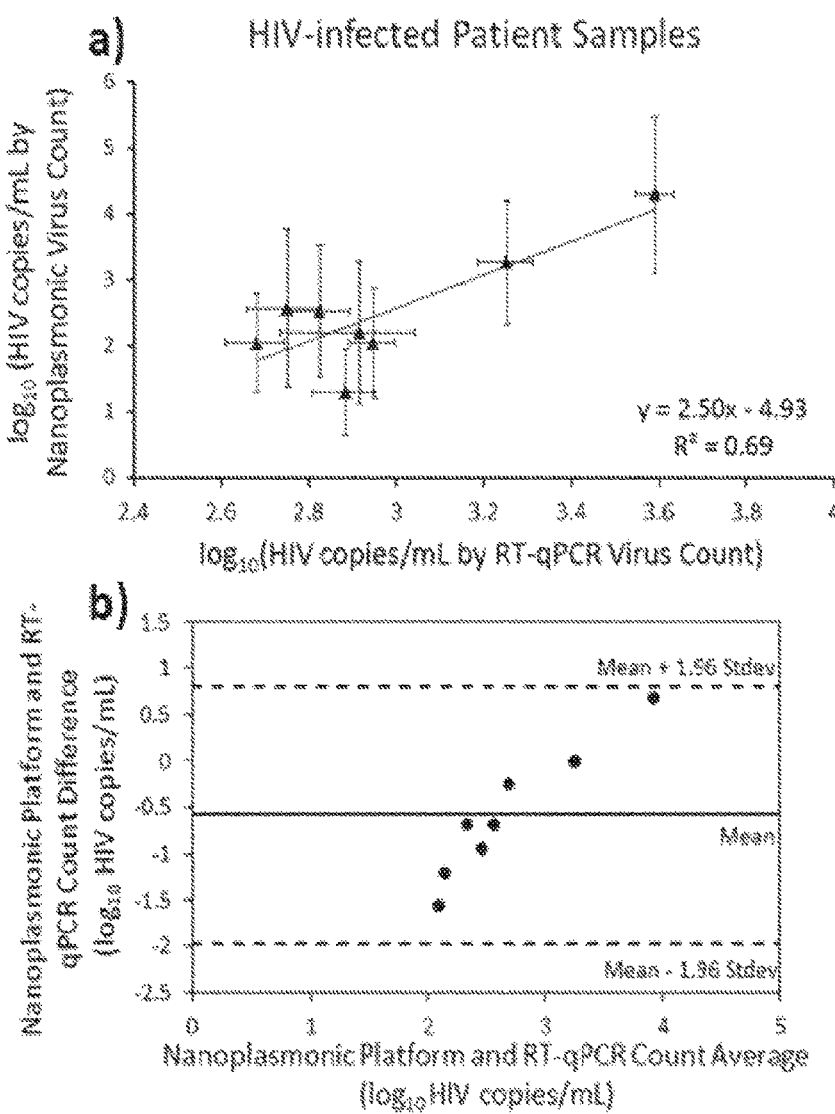
FIGS. 10A and 10B provide quantitative detection with HIV-infected patient samples and provide a comparison between the counts obtained by the nanoplasmonic platform and RT-qPCR.

Turning first to FIG. 10A, quantitative detection results are provided for HIV-infected patient samples. In FIG. 10A, discarded HIV infected patient samples in whole blood were evaluated using the nanoplasmonic platform and correlation was presented between HIV count obtained by RT-qPCR and the nanoplasmonic platform. The nanoplasmonic platform presented a viral load from $(1.3±0.7) \log_{10}$ (copies/mL) to $(4.3±1.2) \log_{10}$ (copies/mL) in patient samples. RT-qPCR count presented a viral load from $(2.7±0.1) \log_{10}$ (copies/mL) to $(3.6±0.1) \log_{10}$ (copies/mL) in patient samples. Quantitative measurements of HIV infected patient samples using both methods are presented in Table 4 below.

TABLE 4

| Patient # | RT-qPCR Count (Mean ± SEM) ($\log_{10}$ copies/mL) | Nanoplasmonic Count (Mean ± SEM) ($\log_{10}$ copies/mL) |
|---|---|---|
| I | 3.6 ± 0.1 | 4.3 ± 1.2 |
| II | 3.3 ± 0.1 | 3.3 ± 0.9 |
| III | 2.9 ± 0.2 | 2.2 ± 1.1 |
| IV | 2.8 ± 0.1 | 2.6 ± 1.2 |
| V | 2.7 ± 0.1 | 2.0 ± 0.8 |
| VI | 3.0 ± 0.1 | 2.0 ± 0.8 |
| VII | 2.8 ± 0.1 | 2.5 ± 1.0 |
| VIII | 2.9 ± 0.1 | 1.3 ± 0.7 |

In FIG. 10B, Bland-Altman Analysis was performed between the nanoplasmonic platform and RT-qPCR counts and did not display an evidence for a systematic bias for HIV viral load for HIV-infected patient blood samples tested.

Example XI

Having established above that HIV viral loads can be captured on a biosensing surface of a nanoplasmonic platform, and then, detected using localized surface plasmon resonance, the next steps for achieving portability for POC detection include implementing this nanoplasmonic platform or an analog structure on a microchip, and then, confirming that this microchip provides similar results. The disposable and portable microchip device makes it possible to perform testing at remote settings where access to instrumentation for such analyses is either unavailable or expensive.

Figure 11:
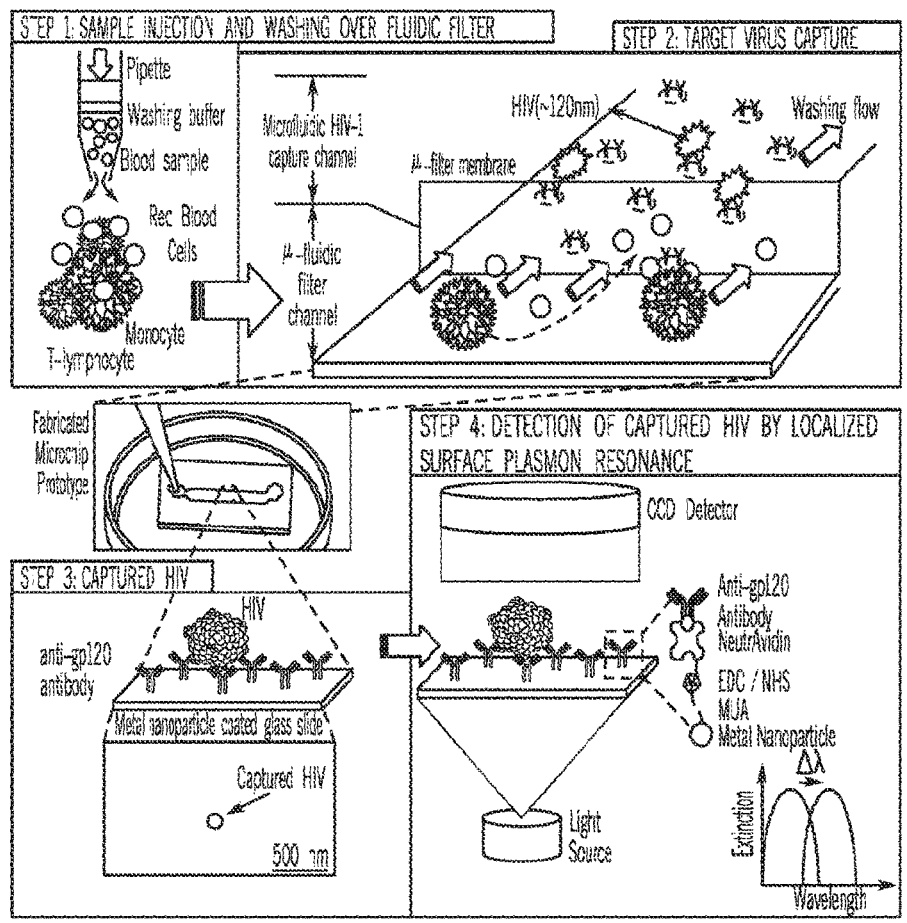
FIG. 11 shows the steps for measuring a viral load on a microchip.

With additional reference to process steps depicted in FIG. 11 and the microchip structure depicted in FIG. 12C, the steps for viral load detection on a microchip are generally described. In steps 1 and 2, a whole blood sample is obtained from a patient and is placed on the microchip. Approximately a 100 μL of fingerprick volume of blood should be sufficient. This blood sample is passed through a microfluidic capture channel in which red blood cells and white blood cells are removed on-chip by filtering. Then in the capture channel depicted in FIG. 12C, HIV-1 in whole blood will be captured using immobilized capture agents on microchannel surface immobilized with metal nanoparticles that are coated by anti-gp120 antibody as is generally depicted in steps 2 and 3 of FIG. 11. In step 4, the captured HIV on the microchip is detected and quantified using a portable CCD-based localized surface plasmon resonance technology.

Example XII

Figure 12:
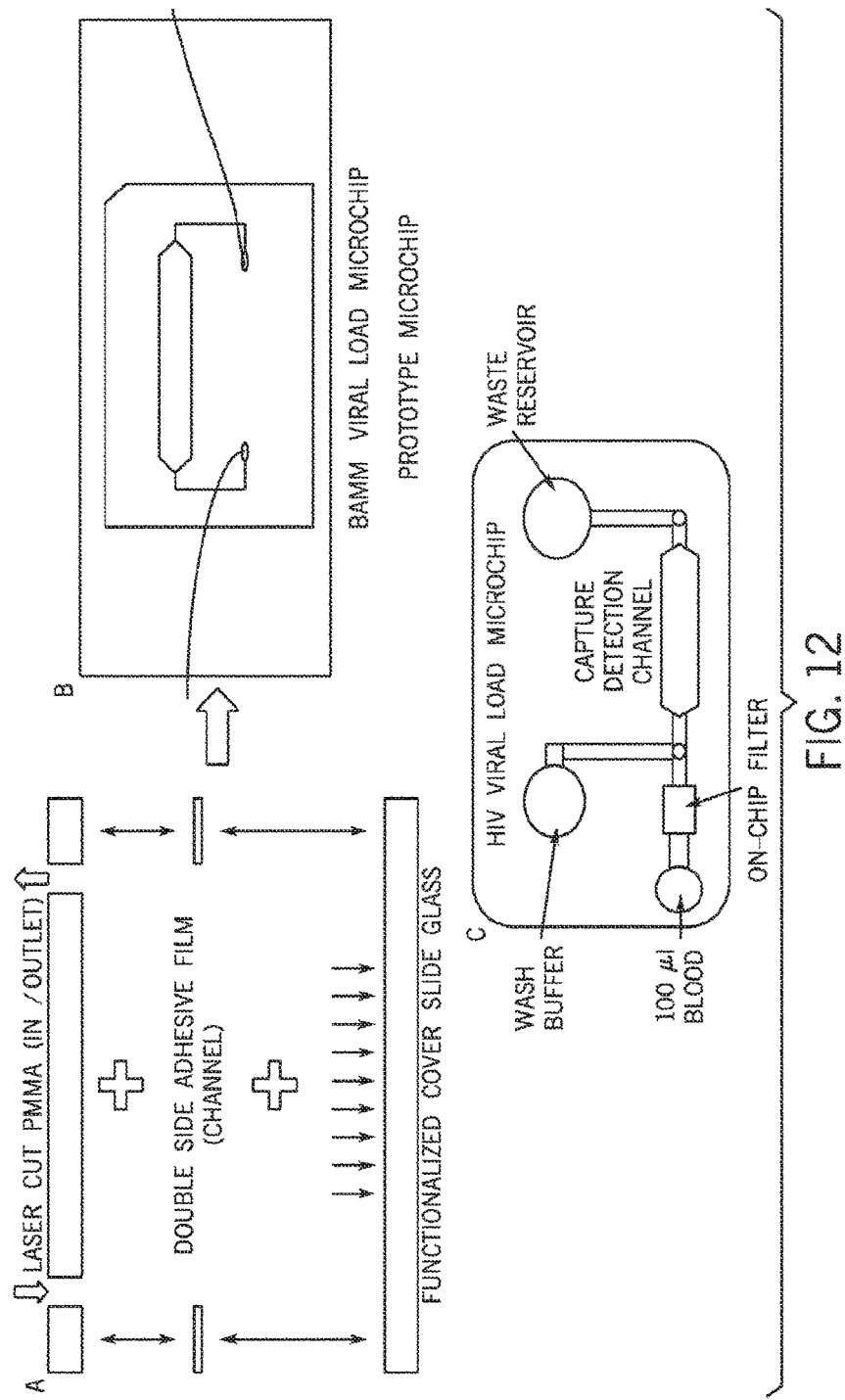
FIGS. 12A through 12C show the fabrication of a viral load microchip.

With particular reference to FIG. 12, a microfluidic device of the type described in the previous example can be constructed in the following way. As best shown in FIG. 12C, the microfluidic device can comprises (i) a passive filtration chamber (e.g., a micromachined polycarbonate filter) that removes red blood cells and white blood cells and (ii) a following chamber that captures HIV from the filtered plasma. The capture chamber of the microchip can be constructed with polystyrene, glass parylene, quartz crystal, graphene and mica layers, polydimethylsiloxane (PDMS), paper, and poly(methyl methacrylate) (PMMA) and double-sided adhesive film as depicted in FIG. 12A.

In the depicted embodiment, a simple channel design is employed with a filter inserted in the middle, which has been characterized with respect to whole blood properties in our other studies. However, in other alternative embodiments, the device or interfaced devices may have tubing that directly connecting chambers or by building the filters into channels.

Virus capture efficiency can be increased by removing the cells from blood using a filter approach. In the chip design, the filter (0.2-3 μm pore size) is placed at the inlet and plasma passing through the filter is directly introduced into the capture chamber. Preferably, red blood cells and white blood cell will not be passing through the filter below 2 μm pore size. This approach will help to capture HIV-1 with higher efficiency in the microchip.

The device fabrication is technically simple involving layered stacking of PMMA, double-sided adhesive film and a glass cover as depicted in FIGS. 12A and 12B, which can be easily scaled up for batch production. The PMMA base has a dimension of 24×40×3.175 $mm^3$ and it is cut using a laser cutter (VersaLaser, VLS2.3). On the PMMA base, an inlet and an outlet are cut out for injecting samples and collecting waste, respectively. The channel is cut into double sided adhesive (DSA) film by the laser cutter. Prior to assembling, surface of the glass coverslip is modified by plasma treatment. The coverslip is then immediately mounted onto the DSA film, which is previously assembled with the PMMA base. After assembling these three components, a microchannel is formed. FIG. 12C shows a schematic of a viral load microchip, which can be fabricated using machining and molding processes. The microchip is made with multiple pieces to ease the integration, assembly, and packaging.

The Hele-Shaw flow theory and design equations can be used to determine the flow rates and shear stress on the surface based on microchannel geometry and dimensions. By targeting optimum shear rates and flow rates for capture, the microfluidic channel dimensions on the microchip can be designed accordingly. The longer and wider the microchip, the more surface is available to capture HIV. The channel height can be made as small as 10 μm, which then would allow viruses to interact more with the functionalized surface. For various channel dimensions, typical flow rates will be in the range of 5-20 μL/min. Preferably, for a rapid test the flow rate should be adjusted to be as high as possible (>5 μL/min) without significantly compromising the capture efficiency.

A further modification to the design illustrated in FIG. 12A can include replacing the glass with non-sharp materials to enhance handling safety. For example, the glass slide may be replaced by parylene or PMMA as these materials are optically transparent and can be functionalized with antibodies.

Example XIII

To capture HIV-1 from fingerprick blood, the microchannels can be functionalized with anti-gp120 antibody as described above with respect to FIG. 1. In addition to anti-gp120 antibody, microchips can be built with various other capture agents including anti-gp41 antibody, anti-gp24 antibody, lectin and/or sCD4.

Although various concentrations of PLL and gold nanoparticles may be used, in order to optimize surface chemistry for maximum detection efficiency, it is believed PLL concentration should generally be in the range of 0.01 mg/ml to 1 mg/ml to immobilized nanoparticles in the range of $1.14 \times 10^{11}$ to $5.7 \times 10^{11}$ particles per mL onto the microchip. It should be appreciated that various nanoparticle concentrations and sizes (10-100 nm) might be used and that optimal PLL concentrations and nanoparticle concentrations may vary based on the nanoparticle size. As described in the examples above, NeutrAvidin is covalently coupled with NHS ester and EDC by incubating the microchannel surface with NeutrAvidin (10 μg/mL in PBS) for 1 h at 4° C. Finally, capture agent solution (e.g., biotinylated anti-gp120, 40 μg/mL in PBS containing 1% (w/v) BSA and 0.09% (w/v) sodium azide) is injected to react at 4° C. for 1 hr. After each step, surfaces can be rinsed with PBS to wash away unreacted molecules. The chips can be stored at 4° C. for up to 3 months without loss of function.

Example XIV

To perform localized surface plasmon resonance, a portable lensless CCD-based optical system is used with the microchips for rapid virus detection and automatic quantification by LSPR. Briefly, HIV-1 from fingerprick blood is captured when flowed in the microchannel functionalized with capture agents. This HIV can be repeatedly and reliably captured with high sensitivity across a range of values that include the current WHO definition of treatment failure (VL>5,000 copies/mL) as well as the DHHS and ACTG definitions of treatment failure (VL>200 copies/mL).

For LSPR detection, wavelength shift or extinction intensity change on the entire channel surface of the chip can be detected by the aid of a CCD sensor (KODAK, KAI-11002, Rochester, N.Y.) carrying 11 million square pixels (9 μm wide) as illustrated in step 4 of FIG. 12. The active CCD sensor area is 37.25×25.70 mm. A portable spectrometer, which scans spectra from 400 nm to 800 nm is used to illuminate active area of the microchip. Once HIV is captured on the active area of the capture detection channel, changes at the close vicinity of the active surface causes a shift in the wavelength or extinction intensity. This shift is detected instantly within 10 seconds by intensity change of the recorded CCD image quantifying the captured viruses. The wavelength shift and/or extinction intensity change is then quantified automatically with the aid of in-house signal processing software such as MATLAB within another 20 seconds.

To summarize, the system detects intensity variations on the CCD resulting from changes of nanoparticle's specific wavelength in close vicinity of active surface quantifying the HIV-1 viral load from whole blood.

HIV can be detected repeatably and reliably with high sensitivity covering the range of values that include the current WHO definition of treatment failure (VL>5,000 copies/mL) as well as the DHHS and ACTG definitions of treatment failure (VL>200 copies/mL).

With further scaling, it is contemplated that the viral load in 100 μL of whole blood can be analyzed in as little as 15 minutes using a system of this type. By controlling parameters such as flow rates, surface chemistry and channel size, capture, detection and assay duration can, within certain limits, be controlled. For instance, it takes 10 minutes (at 10 μL/minute flow rate) to run 100 μL of blood into a microchannel to capture HIV, and an additional 4 minutes to wash the channels (at 20 μL/minute flow rate). It takes an additional 30 seconds to obtain a viral load using the sensor platform by running automated software. A 15-minute viral load is anticipated with a satisfactory throughput performance at the POC, when compared to existing systems (e.g. reverse-transcriptase activity test: 3 days) and RT-qPCR (one day).

Example XV

An example is now provided which describes the construction of a flexible nanoplasmonic platform.

To construct a flexible platform, polyester surfaces were used as a base material for localized surface plasmon resonance (LSPR) experiment. The surfaces were first modified with poly-l-lysine (PLL) (although other layers might be able to immobilize the nanoparticles on the substrate and not interfere with LSPR detection). PLL provided amine groups to immobilize gold nanoparticles on the substrate. The nanoplasmonic immobilization layer was then functionalized with thiol groups, although other attachments between the layer and the substrate or the gold nanoparticles might also be employed as long as it did not impair the ability of the nanoplasmonic platform to be read using LSPR.

To link the one or more surface recognition elements such as antibodies and capture moieties to the gold nanoparticles, a modified surface was formed by preparing a surface of the plurality of gold nanoparticles using a mercaptoundecanoic acid to form carboxyl groups, reacting N-Ethyl-N'-(3-dimethylaminopropyl) carbodiimide hydrochloride with the carboxyl groups to form an amine reactive intermediate, and stabilizing the amine reactive intermediate by N-hydroxysulfosuccinimide to form the modified support surface. Then, NeutrAvidin protein was used to immobilize biotinylated anti-gp120 polyclonal antibody. Additionally, other or additional antibodies may be present based on the pathogens and infectious agents to be detected. It is contemplated that multiple pathogens may be detected on a single flexible nanoplasmonic platform. In some embodiments, the antibody may be a polyclonal antibody. In the context of HIV detection, the antibody and/or capture moieties may be, for example, a gp120 antibody, a gp41 antibody, a gp24 antibody, soluble CD4, or lectin, all of which are able to detect multiple subtypes of HIV. Additionally, in some forms, the modified support surface is linked to at least one of a protein A, a protein G, a protein A/G, a Streptavidin protein, and a NeutrAvidin protein which is used to form chemical bonds to immobilize recognition elements such as the antibody on the modified support surface.

Figure 13:
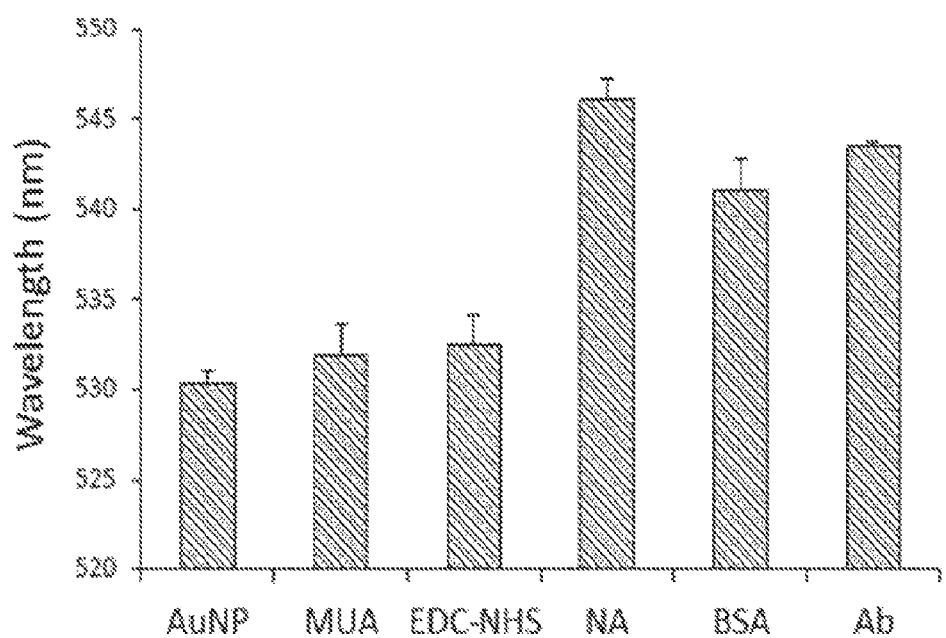
FIG. 13 illustrates the observed wavelengths over a layer-by-layer surface preparation of a flexible nanoplasmonic platform.

As outlined above, after the gold nanoparticle coating onto the PLL modified surface, MUA was self-assembled as a monolayer onto the gold nanoparticle layer. Antibodies immobilized with a favorable orientation using NeutrAvidin have a higher capture efficiency towards bioagents than those immobilized by physical absorption and chemical binding of antibodies onto a surface. To immobilize biotinylated antibodies for HIV capture, surfaces were modified with NeutrAvidin. To prevent non-specific binding, 10% BSA solution was used as a blocking agent. Then, biotinylated anti-gp120 polyclonal antibody (Ab) was incubated on the NeutrAvidin-coated surface. After each surface modification step, the surfaces were rinsed with 1×PBS three times to remove unbound chemical moieties. With the assembly of these further layers, it was observed that MUA, NeutrAvidin, BSA and Ab collectively shifted the maximum wavelength to 543.5±0.3 nm as is illustrated in FIG. 13. Here, a flexible nanoplasmonic surface was constructed, and this platform presented comparable results with the previously described polystyrene-based nanoplasmonic technology.

Example XVI

This example describes the use of disposable chips to detect antiepileptic drug (AED) serum concentrations at the point of care using the nanoplasmonic platform.

Epilepsy is a neurological disorder characterized by brief episodes of involuntary shaking sometimes accompanied by loss of consciousness and control of bowel or bladder function. About 88% of patients have reported drug related side-effects including restlessness, feeling of aggression, and suicide associated with depression. Most of these side effects are dose dependant.

AEDs are the mainstay of treatment for persons with epilepsy (PWE). However, as many as two out of three PWE suffer from recurrent seizures or AED-related side effects. In either case, the optimization of AED dosages is clinically important and often guided by measuring AED serum concentrations. These side-effects can be minimized by adjusting the antiepileptic drug (AED) dosage and timing of the dosage. Monitoring of the AED serum concentrations can guide the AED optimization goal. Currently, the blood tests used for AED serum concentrations are lab based and cannot be performed at home or at the time of seizures, and thus, obtaining blood tests is presently impractical due to the associated inconvenience (lab based detection) and costs, as well as the often long latency between side-effects and/or seizures and when blood tests are obtained.

Figure 14:
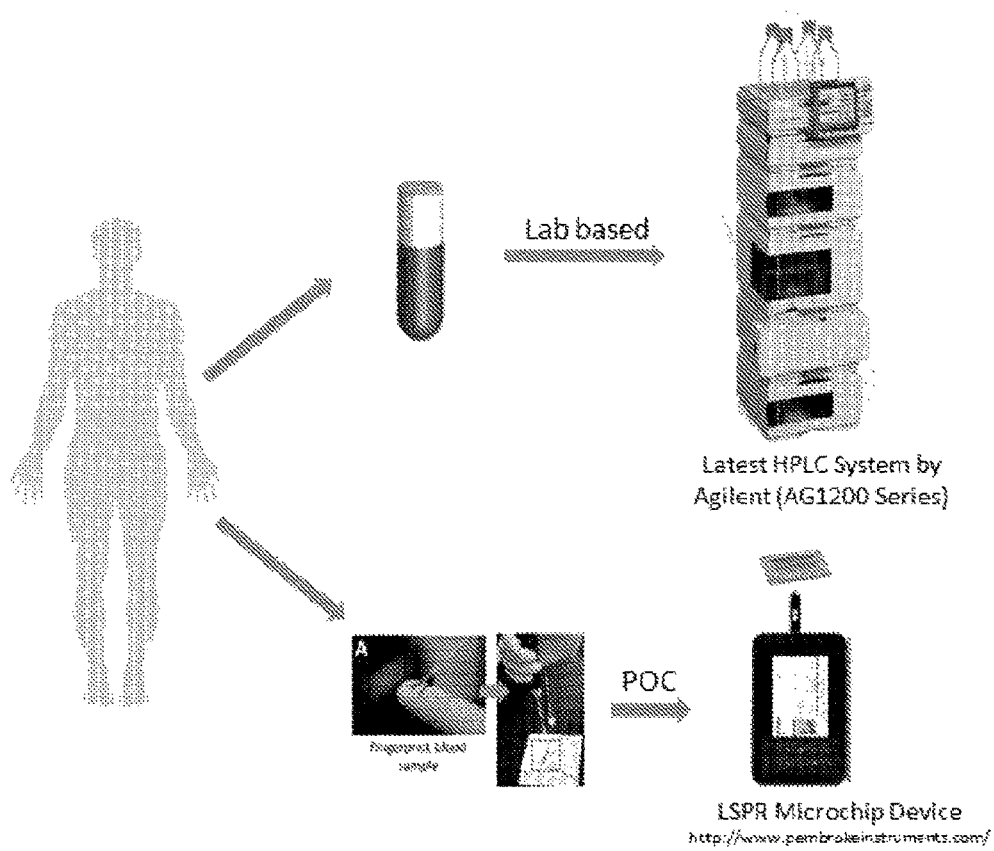
FIG. 14 illustrates the different methods used for antiepileptic drug quantification. The gold standard method required expensive HPLC equipment and skilled technician and is shown as the upper path that is lab based. In contrast, localized surface plasmon resonance based detection can be applied in point-of-care settings as is illustrated in the lower path.

AED serum concentrations are conventionally quantified by High Performance Liquid Chromatography (HPLC) in conjunction with UV and photodiode arrays as illustrated by the top path in FIG. 14. However, these methods are lab-based and not point-of-care nor obtained at the moment of need (for example after a seizure or when side effects are occurring, because they rely on expensive equipment and skilled technicians.

Now, a microfluidic-based disposable AED detection system is described that can be performed anywhere and automated to handle 10-100 µL of blood obtained with a fingerprick, such as used for blood glucose monitoring. Rather than blood, it is contemplated that other bodily fluids such as urine, sweat and saliva could also be collected and analyzed. The glass surface coated with gold nanoparticles is functionalized with anti-AED antibody for specific capture of AED molecules. Upon drug-Ab binding, a shift in the extinction intensity and wavelength spectrum can be monitored due to localized surface plasmon resonance effect of gold nanoparticles. The system consists of a portable spectrophotometer for detection and presents the results in approximately 10 minutes. A version of this device may be made with read-outs that the patient or family member can monitor, to report to the physician or to implement actions that the physician provided them in advance. This new microfluidic-based disposable AED detection system is illustrated on the bottom path of FIG. 14 and satisfies the need for a simple, rapid, reliable and disposable test for AED measurements that can be performed at the doctor's office or by the patient or a family member at home.

In the development of this microfluidic-based disposable AED detection system, two interdependent, distinct specific aims are met. First, enzyme-linked immunosorbent assay (ELISA) is translated to 10 minutes localized surface plasmon resonance (LSPR) microchip device for the detection of AED serum concentrations, starting with AEDs that have narrow therapeutic windows. A laptop/tablet application may be used to send results to doctor's office. A microchip device is provided contains multiple microchannels whereby serum concentrations of various AEDs are simultaneously detected for patients on polytherapy, as well as other components of whole blood, such as WBC counts. Second, the device is validated with sufficient numbers of discarded anonymous clinical samples to demonstrate acceptable sensitivity and specificity. Bland-Altman analysis is performed to statistically compare the LSPR results with HPLC (i.e., gold standard method).

The disposable LSPR microchip employs a gold nanoparticle coated surface functionalized with anti-AED antibody to quantify the drug amount. A portable spectrophotometer is used for spectrum analysis for the read-out, which can then be sent automatically to the doctor's office if the test is done elsewhere. The disposable microchip may be inexpensive (for example, less than $2), may provide results within 10 minutes, may be stable at room temperature, and may be used by patients and health-care providers.

Figure 15:
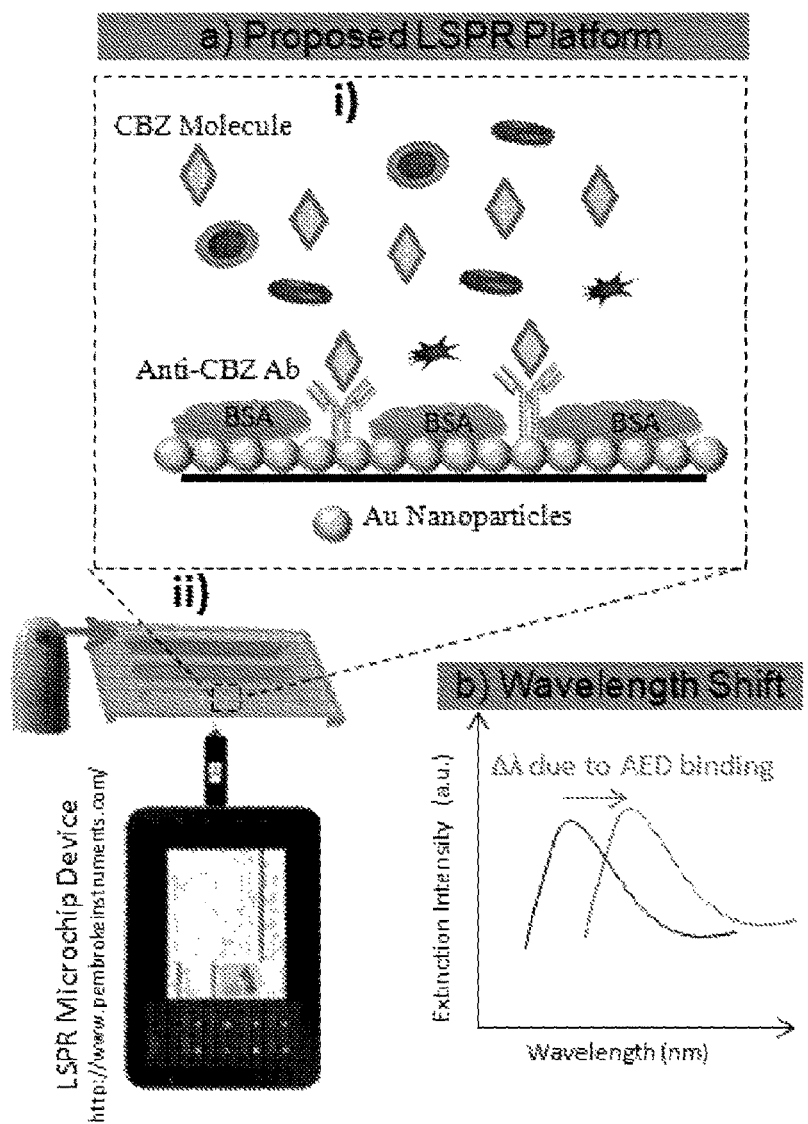
FIG. 15 illustrates the design of a microfluidic LSPR microchip for AED quantification.

The design of the proposed LSPR microfluidic assay for the quantification of AED in a blood serum is illustrated in FIG. 15. The anti-Carbamazepine (CBZ) antibody is attached to the gold nanoparticles. Anti-CBZ antibody specifically captures the CBZ present in the blood serum. When the chip surface is analyzed using a spectrophotometer, the gold nanoparticles produce the extinction intensity spectrum due to their enhanced nanoplasmonic properties with peak intensity at specific wavelength. This Anti-CBZ antibody capture events quantitatively shift the peak wavelength (that is, the higher the concentration of AED in blood serum, the higher is the shift in the peak wavelength).

Figure 16:
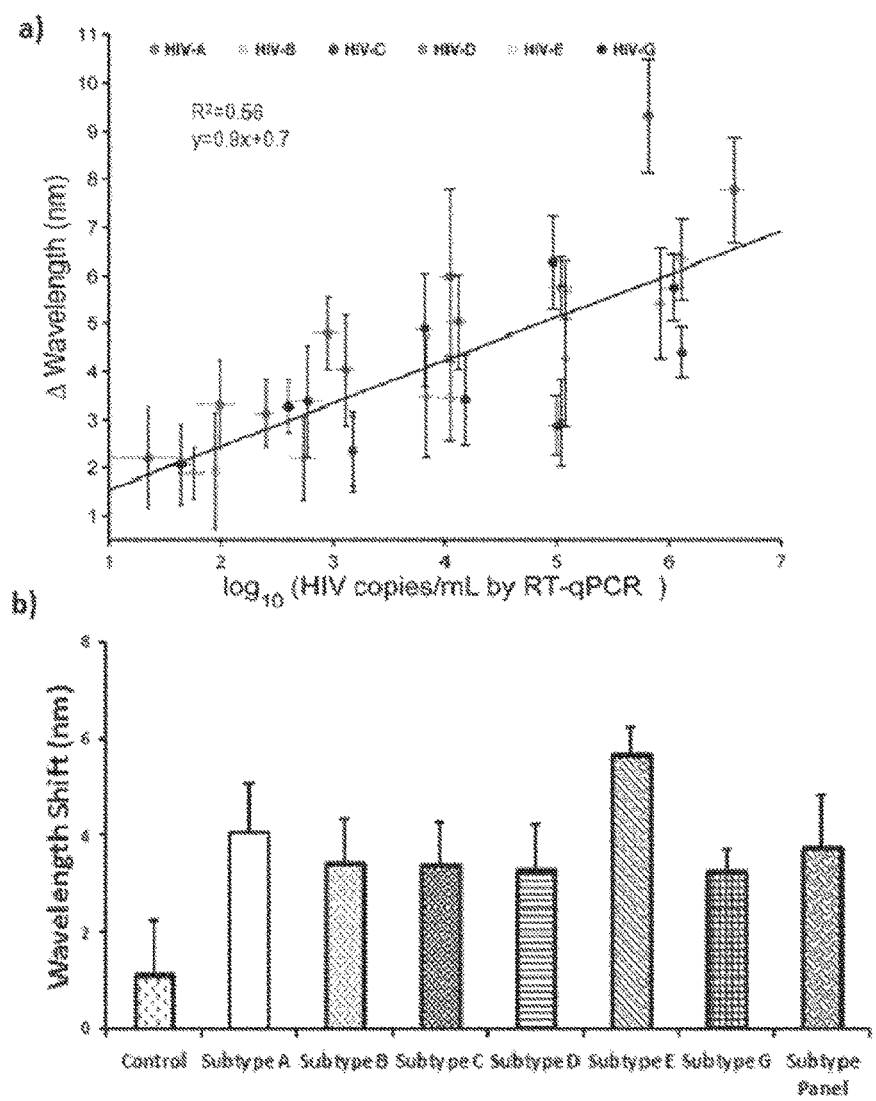
FIG. 16 illustrates another evaluation of the nanoplasmonic platform technology with HIV samples.

The nanoplasmonic platform technology described above for the intact HIV detection from unprocessed whole blood can be adapted for quantification of AED in a blood serum. This platform allows efficient capture of intact HIV from whole blood by immobilized gold nanoparticles, resulting in a shift in the peak of the maximum extinction wavelength. This detection technology utilizes from LSPR signals of metal nanoparticles based on the changes in collective oscillations of free electrons surrounding the nanoparticles. For producing the nanoplasmonic platform, gold nanoparticles were first immobilized on polystyrene surfaces using poly-L-lysine (PLL) as illustrated in FIG. 1. After the activation of gold surfaces with several chemicals and activators (11-Mercaptoundecanoic acid (MUA), N-Ethyl-N'-(3-dimethylaminopropyl) carbodiimide hydrochloride (EDC), and N-hydroxysulfosuccinimide (NHS)), anti-gp120 polyclonal antibodies were immobilized for the capture of intact HIV from whole blood samples. To analyze the wavelength and extinction intensity data, a curve fitting method was developed, which was written using MATLAB software to find the nanoplasmonic wavelength peak of each recorded experimental spectra. Then, multiple HIV subtypes (i.e., A, B, C, D, E, G, and panel (a mixture HIV subtype A, B, C, D, and circulating recombinant forms (CRF01_AE and CRF02_AG)) spiked in whole blood were evaluated as a model detection platform. Various concentrations of multiple HIV subtypes, i.e., A, B, C, D, E, G, and panel, spiked in whole blood ranging from 50 to $(3.8\pm1.2)\times10^6$ copies/mL were assessed as illustrated in FIG. 16A, which shows the aggregated data from FIGS. 6A-6H. Limit-of-detection (LOD) for each subtype was determined as a statistically significant peak shift compared to the control (i.e., whole blood without HIV) samples. LOD was observed as 1,346±257 copies/mL for HIV subtype A, 10,609±2,744 copies/mL for HIV subtype B, 14,942±1,366 copies/mL for HIV subtype C, 98±39 copies/mL for HIV subtype D, 120,159±15,368 copies/mL for HIV subtype E, 404±54 copies/mL for HIV subtype G, and 661±207 copies/mL for HIV subtype panel as illustrated in FIG. 16B. These results demonstrated that the presented nanoplasmonic platform can detect and capture intact HIV from unprocessed whole blood samples with a sensitivity of down to 98±39 copies/mL. The platform was further validated with 8 HIV-infected anonymous discarded patient whole blood samples. The patient samples presented wavelength shifts from 2.3±0.7 nm to 4.3±1.0 nm for (1.3±0.7) $\log_{10}$ copies/mL to (4.3±1.2) $\log_{10}$ copies/mL, respectively as illustrated in FIG. 10A. To evaluate quantitative detection, a standard curve was obtained from HIV spiked whole blood samples using the wavelength shifts from the nanoplasmonic response and the HIV viral load obtained by RT-qPCR (gold standard method). Bland-Altman comparison analysis was used to evaluate the repeatability of the nanoplasmonic platform count using residual analysis in comparison to RT-qPCR counts. The results agreed with the RT-qPCR results in the clinically acceptable range, and there was no evidence observed for a systematic bias for HIV viral load for tested HIV-infected patient blood samples as illustrated in FIG. 10B. These results indicated that the nanoplasmonic biosensing platform is reliable, accurate, repeatable and feasible for small structures such as virus detection without any sample preprocessing. This presented platform technology can be potentially used as a broadly applicable tool to diagnose other clinical diseases or to monitor treatment efficacy in resource-constrained settings. Additionally, this platform technology can be used to detect oncoviruses as well.

For AED measurement, a similar microfluidic based LSPR setup may be used to that described above for HIV viral load quantification.

In some embodiments, the microfluidic channel is designed by sandwiching double-sided adhesive film (DSA) (50 μm thick; obtained from iTapestore of Scotch Plains, N.J.) between glass slide and poly(methyl methacrylate) (PMMA) (3 mm thick; obtained from McMaster Carr of Atlanta, Ga.). Both of the DSA and PMMA were cut using a laser cutter (Versa Laser™, AZ).

In some embodiments, the surface chemistry starts with the surface immobilization of gold nanoparticles inside the microfluidic channels using PLL. After the activation of gold surfaces with several chemicals and activators (MUA, EDC, and NHS), NeutrAvidin is immobilized followed by conjugation with biotinylated anti-CBZ monoclonal antibodies. Serum samples spiked with CBZ at various concentrations are tested by using these chips. The chips are analyzed using portable spectrophotometer and CCD sensor.

Figure 17:
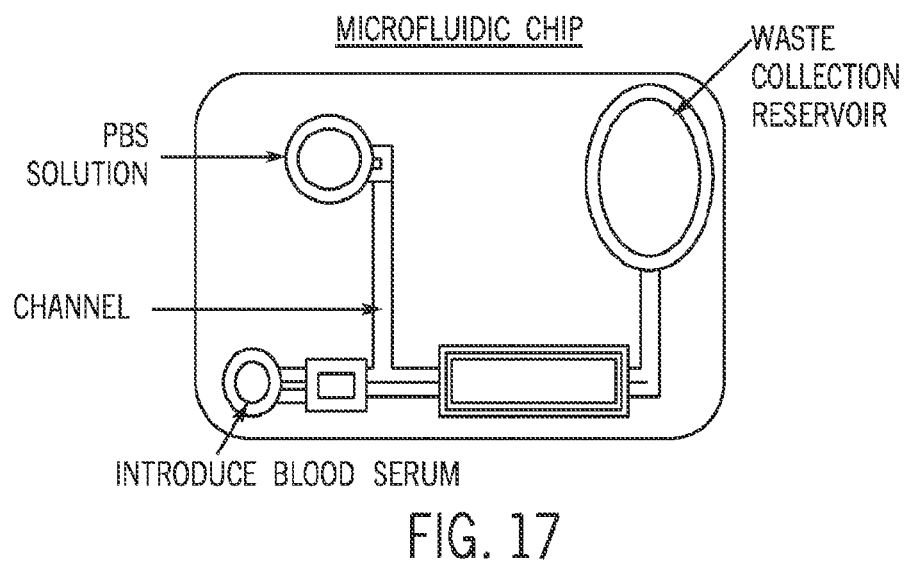
FIG. 17 is a top view schematic of a disposable cartridge of a fluidic microchip and fluid reservoirs. The chip has fluidic interface between the microfluidic channels.

It is contemplated that the microfluidic devices may be integrated with disposable cartridges. FIG. 17 schematically demonstrates a schematic of such cartridge, which can be fabricated using machining and molding processes. The cartridge can be made with multiple pieces to ease the integration, assembly, and packaging of the microchip. The chip may be functionalized before being placed into the cartridge. The microfluidic chips can be disposable for ease of use and to avoid contamination. They might be made of glass bonded to glass or plastic with an adhesive to make the chip easy to fabricate. The material cost to build such a channel could be less than $2 for batch, although the material cost should in no way be considered limiting.

Example XVII

In this example, the capture and detection of *Escherichia coli* (*E. coli*) using the nanoplasmonic platform technology are described. As mentioned above, other bacteria as well as fungi or yeast could also be captured and detected using this platform.

The surface chemistry for *E. coli* capture and detection was started with the modification of the polystyrene substrates with poly-l-lysine (PLL) (although other layers might also be able to immobilize the nanoparticles on the substrate and not interfere with LSPR detection). PLL provided amine groups to immobilize gold nanoparticles on the substrate. The nanoplasmonic immobilization layer was then functionalized with thiol groups, although other attachments between the layer and the substrate or the gold nanoparticles might also be employed as long as it did not impair the ability of the nanoplasmonic platform to be read using LSPR.

To link the one or more surface recognition elements such as antibodies and capture moieties to the gold nanoparticles, a modified support surface was formed by preparing a surface of the plurality of gold nanoparticles using a mercaptoundecanoic acid to form carboxyl groups, reacting N-Ethyl-N'-(3-dimethylaminopropyl) carbodiimide hydrochloride with the carboxyl groups to form an amine reactive intermediate, and stabilizing the amine reactive intermediate by N-hydroxysulfosuccinimide to form the modified support surface. Then, NeutrAvidin protein was used to immobilize anti-Lipopolysaccharide Binding Protein (LBP) antibody. *E. coli* surface has a specific polysaccharide called lipopolysaccharide (LPS), and thus, LBP was linked to the anti-LBP antibody for the efficient capture and detection of *E. coli*. The anti-LBP antibody allows LBP to gain its favorable orientation for the efficient capture and detection. Additionally, other or additional antibodies may be present based on the pathogens and infectious agents to be detected. It is contemplated that multiple pathogens may be detected on a single nanoplasmonic platform. A multiplexed detection platform with parallel channels is also contemplated. In some embodiments, the antibody may be a polyclonal antibody. In the context of *E. coli* detection, the antibody and/or capture moieties may be, for example, an anti-LPS antibody, LBP, cluster of differentiation 14 protein (CD14) of human monocyte and anti-flagellin antibody, all of which are able to detect *E. coli*. Additionally, in some forms, the modified support surface is linked to at least one of a protein A, a protein G, a protein A/G, a Streptavidin protein, and a NeutrAvidin protein which is used to form chemical bonds to immobilize recognition elements such as the antibody on the modified support surface.

In the experiments, *E. coli* strain BL21 Star™ was used, and cultured onto Luria-Bertani (LB) agar plates containing 100 mg/mL of ampicillin. Then, the sample was incubated at 37° C. for 16 hours. An isolated *E. coli* colony was picked from the plate and inoculated in 5 mL of LB medium on another LB agar plate containing 100 mg/mL of ampicillin. The *E. coli* culture was transferred and incubated at 37° C. with shaking at 250 rpm for 16 hours, and then, aliquoted as a standard stock for all experiments. After that, the stock solution was diluted ten-fold in phosphate buffered saline (PBS) and spread on LB-ampicillin plates. After overnight incubation at 37° C., single colonies of *E. coli* were quantified, and the number of the original concentration of the stock was calculated.

Figure 18:
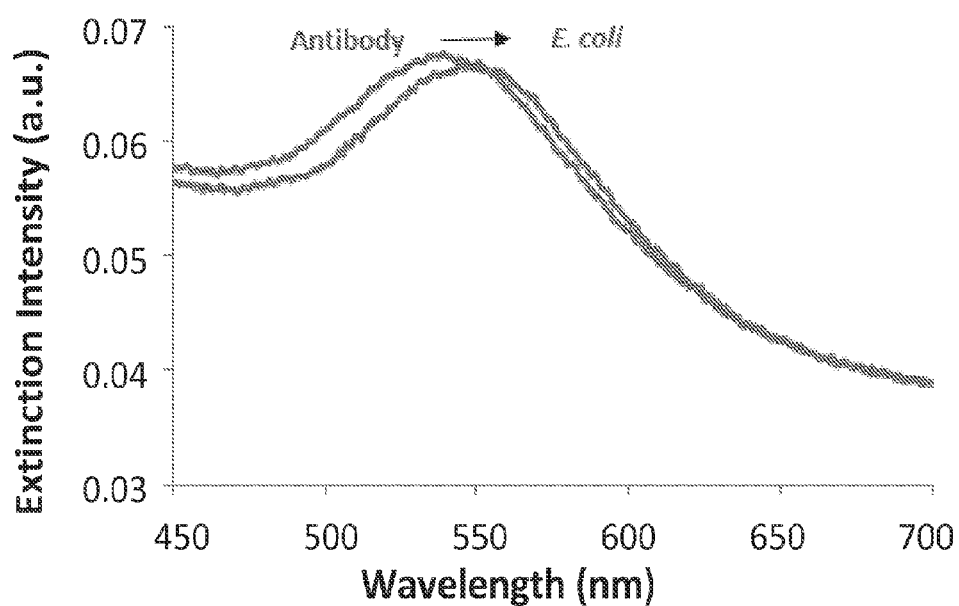
FIG. 18 illustrates the original wavelength spectra and demonstrates the wavelength shift after the application *E. coli*.
Figure 19:
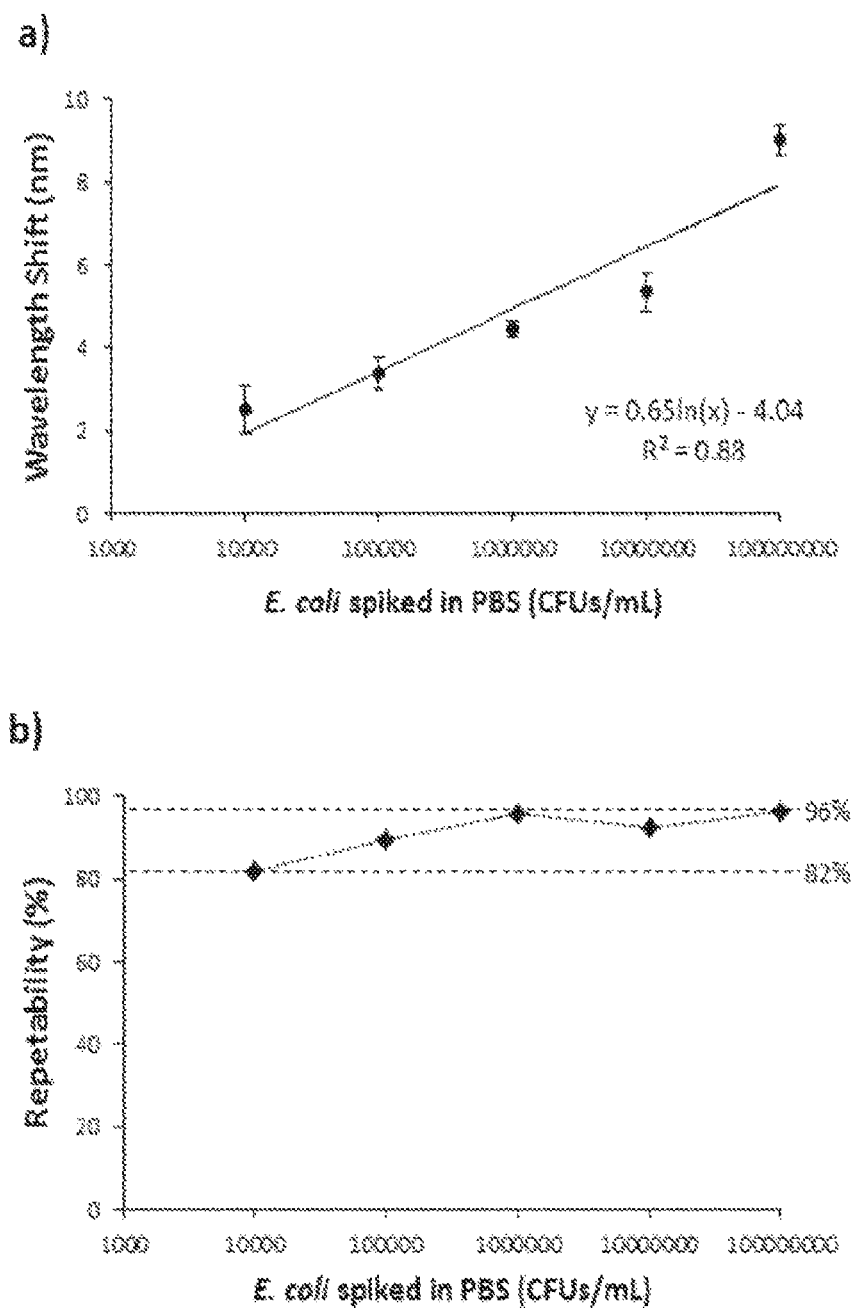
FIG. 19A provides validation of the nanoplasmonic platform with spiked in PBS using curve fitting method in terms of wavelength change.
FIG. 19B illustrates the repeatability parameter for *E. coli* spiked in PBS samples in terms of wavelength change.

Following the quantification of the stock sample, *E. coli* spiked in PBS samples were prepared for the final concentration ranging from $10^4$ to $10^8$ CFUs/mL. 100 μL of the *E. coli* spiked sample was loaded into each antibody immobilized surface of the nanoplasmonic platform and incubated at 4° C. for an hour. PBS samples without *E. coli* spiking were used as controls. Following each surface modification step, the surfaces were rinsed with 1×PBS three times to remove unbound bacteria and chemical moieties. In the presence of *E. coli*, the peak of wavelength at previous step (that is, LBP binding) shifted as shown in FIG. 18. In the selected detection range, the highest detected peak shift was observed as 9.0 nm±0.4 nm at $10^8$ CFUs/mL concentration as shown in FIG. 19A. The peak shift decreased with decreasing *E. coli* concentration, and the lowest shift was observed as 2.5 nm±0.6 nm at $10^4$ CFUs/mL concentration as also shown in FIG. 19A. Additionally, the repeatability parameter was observed to be 82-96% for *E. coli* capture and detection experiments using nanoplasmonic platform as illustrated in FIG. 19B. Here, a reliable, repeatable, feasible, label-free, and fluorescence-free and repeatable technology is presented that captures and detects *E. coli* from biologically relevant solutions such as PBS, blood, urine, and saliva.

Example XVIII

In this example, the capture and detection of interferon-γ using nanoplasmonic platform technology is described.

The quantification of the released interferon-γ (IFN-γ) has been used to evaluate the status of tuberculosis (TB)

patients. T cells release IFN-γ as a host cellular immune response upon the stimulation of whole blood with TB-specific antigens.

To construct a nanoplasmonic platform for the IFN-γ capture and detection, polystyrene surfaces were first modified with poly-l-lysine (PLL). Here, PLL provided amine groups to immobilize gold nanoparticles on the substrate. The nanoplasmonic immobilization layer was then functionalized with thiol groups, although other attachments between the layer and the substrate or the gold nanoparticles might also be employed as long as it did not impair the ability of the nanoplasmonic platform to be read using LSPR.

To bind the one or more surface recognition elements such as antibodies and capture moieties to the gold nanoparticles, a modified support surface was formed by preparing a surface of the plurality of gold nanoparticles using a mercaptoundecanoic acid to form carboxyl groups, reacting N-Ethyl-N'-(3-dimethylaminopropyl) carbodiimide hydrochloride with the carboxyl groups to form an amine reactive intermediate, and stabilizing the amine reactive intermediate by N-hydroxysulfosuccinimide to form the modified support surface. Then, Protein G was used to immobilize anti-IFN-γ antibody. Additionally, other or additional antibodies may be present based on the pathogens and infectious agents to be detected. It is contemplated that multiple pathogens may be detected on a single nanoplasmonic platform. In some embodiments, the antibody may be a polyclonal antibody. Additionally, in some forms, the modified support surface is linked to at least one of a protein A, a protein G, a protein A/G, a Streptavidin protein, and a NeutrAvidin protein which is used to form chemical bonds to immobilize recognition elements such as the antibody on the modified support surface.

Figure 20:
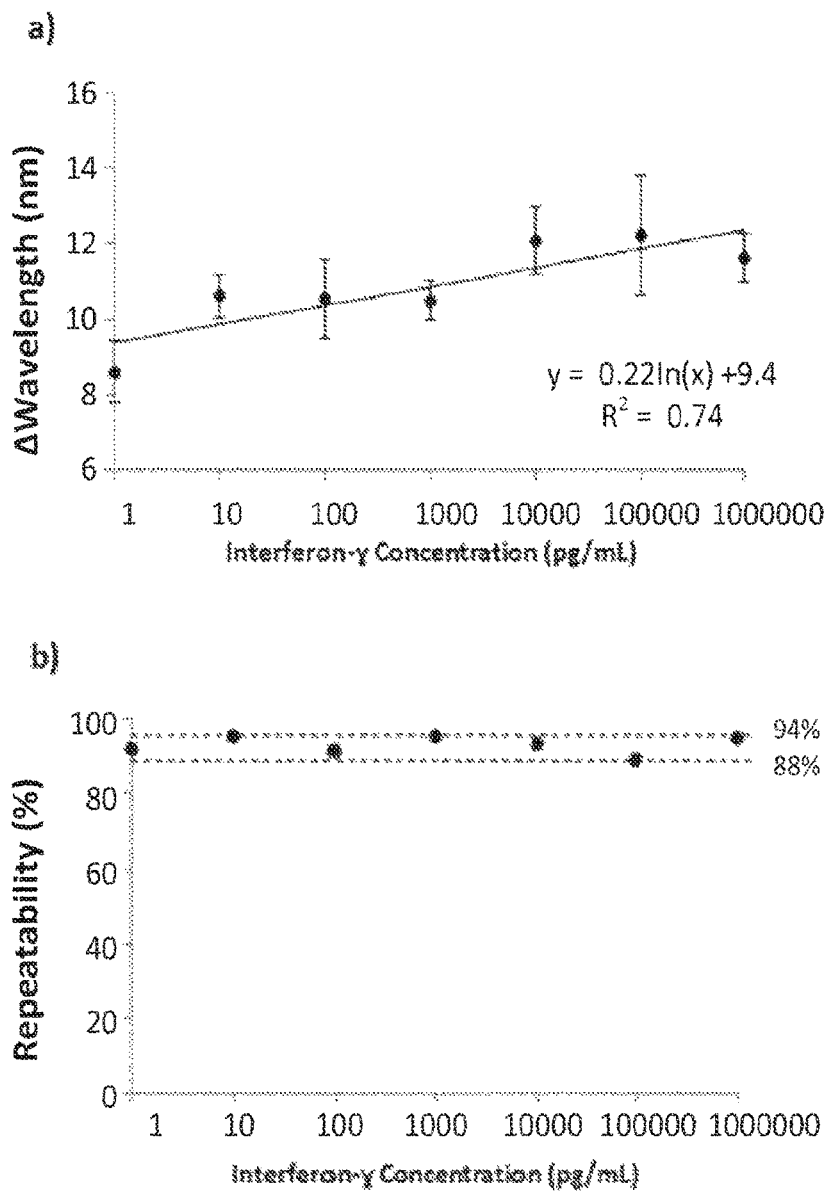
FIG. 20A provides validation of the nanoplasmonic platform with IFN-γ spiked in PBS samples using curve fitting method in terms of wavelength change.
FIG. 20B illustrates the repeatability parameter for IFN-γ spiked in PBS samples in terms of wavelength change.

After the biosensing platform was prepared, a broad range of concentrations (1 pg/mL to 1 μg/mL) for IFN-γ spiked in PBS samples was evaluated, and the results of which are presented in FIG. 20A. In the experiments, 100 μL of IFN-γ spiked sample was loaded into each antibody immobilized surface of the nanoplasmonic platform and incubated at 4° C. for an hour. Following each surface modification step, the surfaces were rinsed with 1×PBS three times to remove unbound IFN-γ and chemical moieties. In the selected detection range, the highest detected peak shift was observed as 11.6 nm±0.7 nm at 1 μg/mL of IFN-γ spiked concentration as illustrated in FIG. 20A. The peak shift decreased with decreasing IFN-γ concentration, and the lowest shift was observed as 8.6 nm±0.8 nm at 1 pg/mL of IFN-γ spiked concentration as illustrated in FIG. 20A. Additionally, the repeatability parameter was observed to be 88-94% for IFN-γ detection experiments using nanoplasmonic platform as illustrated in FIG. 20B. Here, a reliable, repeatable, feasible, label-free, and fluorescence-free and repeatable technology is presented that detects IFN-γ from biologically relevant solutions such as PBS.

Example XIX

This example describes the capture and detection of intact Hepatitis B virus using the nanoplasmonic platform technology.

The surface chemistry for intact Hepatitis B virus (HBV) capture and detection was started with the modification of the polystyrene substrates with poly-l-lysine (PLL) (although other layers might be able to immobilize the nanoparticles on the substrate and not interfere with LSPR detection). PLL provided amine groups to immobilize gold nanoparticles on the substrate. The nanoplasmonic immobilization layer was then functionalized with thiol groups, although other attachments between the layer and the substrate or the gold nanoparticles might also be employed as long as it did not impair the ability of the nanoplasmonic platform to be read using LSPR.

To bind the one or more surface recognition elements such as antibodies and capture moieties to the gold nanoparticles, a modified support surface was formed by preparing a surface of the plurality of gold nanoparticles using a mercaptoundecanoic acid to form carboxyl groups, reacting N-Ethyl-N'-(3-dimethylaminopropyl) carbodiimide hydrochloride with the carboxyl groups to form an amine reactive intermediate, and stabilizing the amine reactive intermediate by N-hydroxysulfosuccinimide to form the modified support surface. Then, protein G was used to immobilize anti-HBV-HBc (core) and anti-HBV-HBs (surface) antibodies. Additionally, other or additional antibodies may be present based on the pathogens and infectious agents to be detected. It is contemplated that multiple pathogens may be detected on a single nanoplasmonic platform. In some embodiments, the antibody may be a polyclonal antibody. Additionally, in some forms, the modified support surface is linked to at least one of a protein A, a protein G, a protein A/G, a Streptavidin protein, and a NeutrAvidin protein which is used to form chemical bonds to immobilize recognition elements such as the antibody on the modified support surface.

Figure 21:
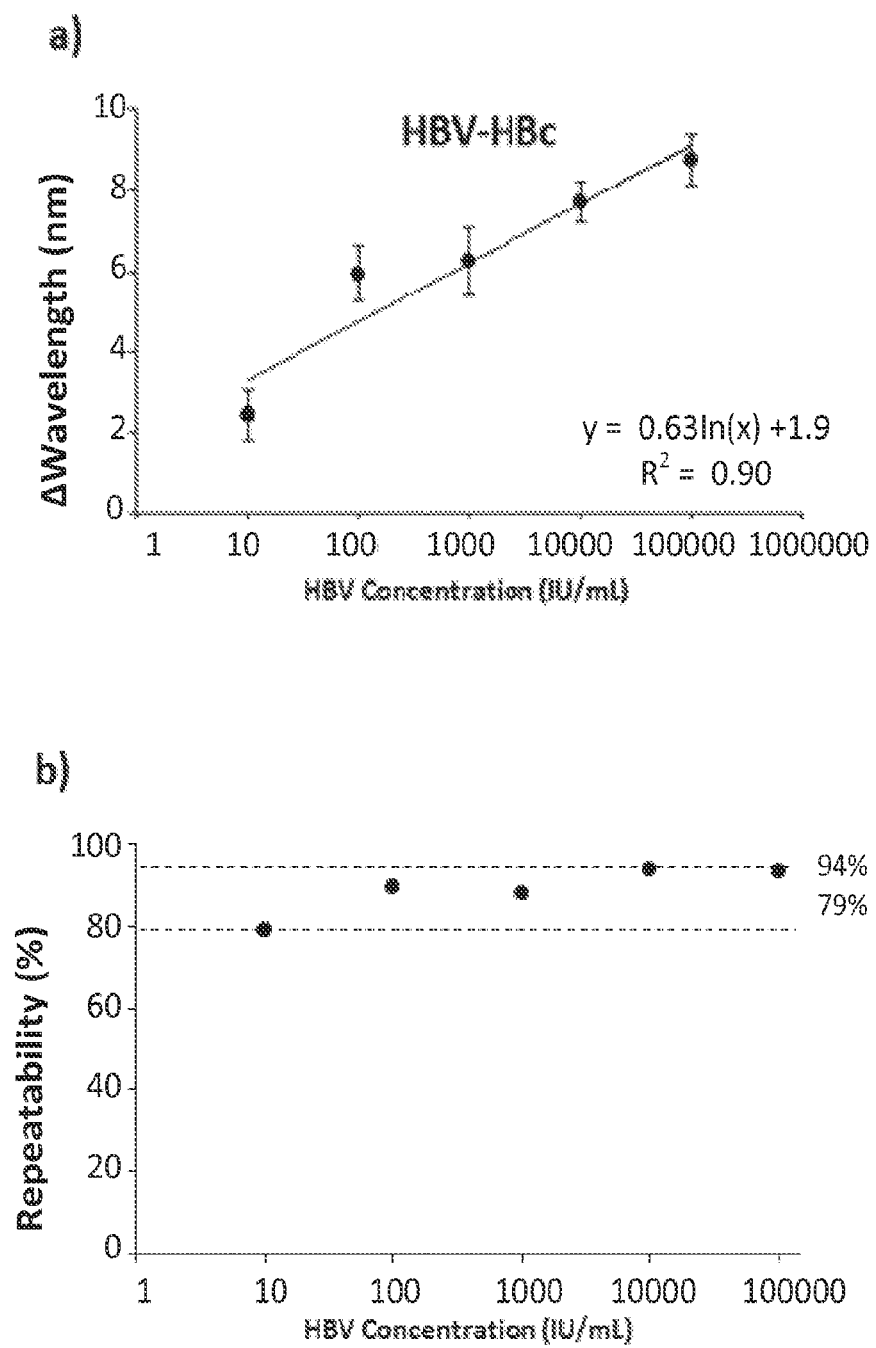
FIG. 21A provides validation of the nanoplasmonic platform for HBV-HBc detection using curve fitting method in terms of wavelength change.
FIG. 21B illustrates the repeatability parameter for HBV-HBc spiked samples in terms of wavelength change.
Figure 22:
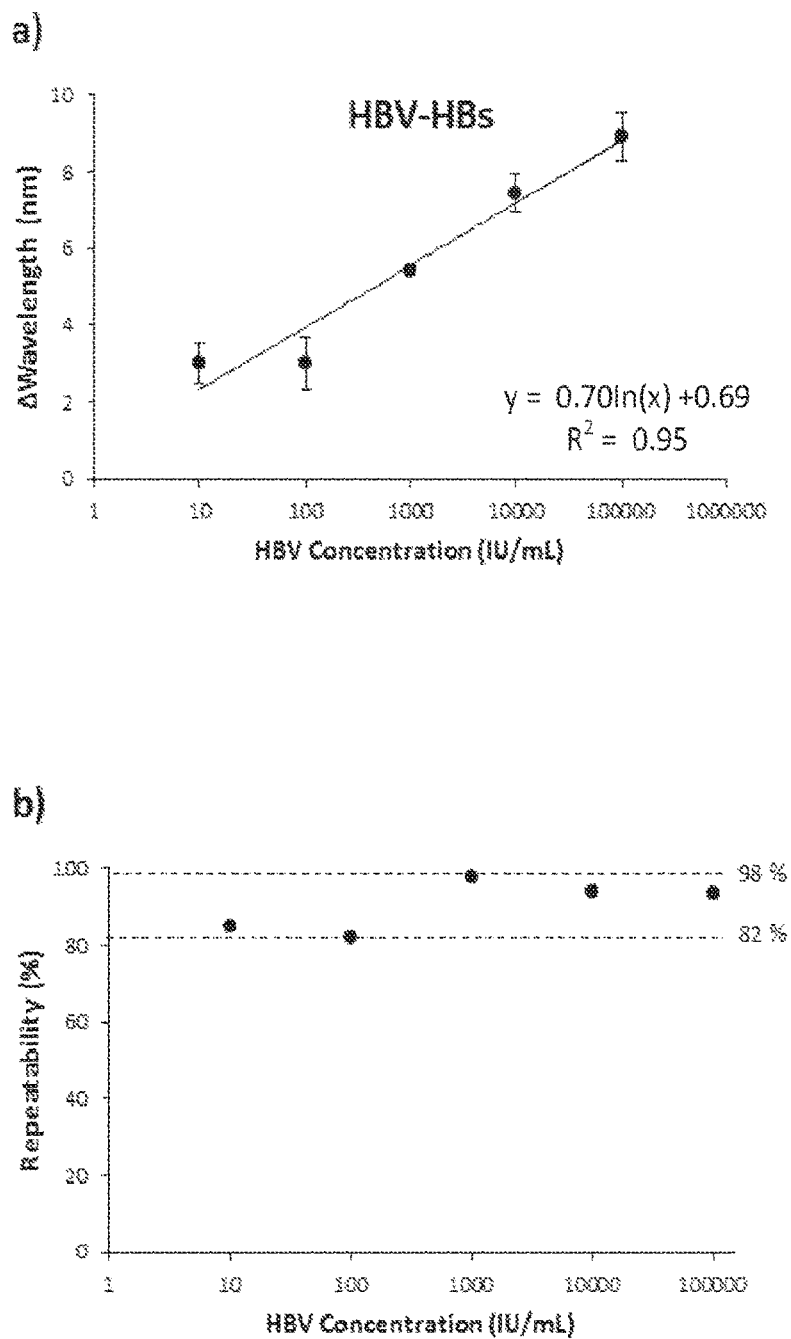
FIG. 22A provides validation of the nanoplasmonic platform for HBV-HBs detection using curve fitting method in terms of wavelength change.
FIG. 22B illustrates the repeatability parameter for HBV-HBs spiked samples in terms of wavelength change.

Following the quantification of the stock sample, HBV spiked in culture media and PBS samples were prepared for the final concentration ranging from 10 to $10^5$ IU/mL. The unit of measurement (i.e., IU/mL) equals to 5-6 genome copies/mL. 100 μL of HBV spiked sample was loaded into each antibody immobilized surface of the nanoplasmonic platform and incubated at 4° C. for an hour. PBS and media samples without HBV spiking were used as controls. Following each surface modification step, the surfaces were rinsed with 1×PBS three times to remove unbound HBV and chemical moieties. In HBV-HBc detection experiments, the highest detected peak shift was observed as 8.8±0.6 nm at $10^5$ IU/mL of HBV concentration as illustrated in FIG. 21A. The peak shift decreased with decreasing HBV concentration, and the lowest shift was observed as 2.5 nm±0.6 nm at 10 IU/mL of HBV concentration as illustrated in FIG. 21A. The repeatability parameter was observed to be 79-94% for HBV-HBc capture and detection experiments using nanoplasmonic platform as illustrated in FIG. 21B. In HBV-HBs detection experiments, the highest detected peak shift was observed as 8.9±0.6 nm at $10^5$ IU/mL of HBV concentration as illustrated in FIG. 22A. The peak shift decreased with decreasing HBV concentration, and the lowest shift was observed as 3.0±0.5 nm at 10 IU/mL of HBV concentration as illustrated in FIG. 22A. The repeatability parameter was observed to be 82-98% for HBV-HBs capture and detection experiments using nanoplasmonic platform as illustrated in FIG. 22B. The limit-of-detection was evaluated for HBV-HBc and HBV-HBs experiments by comparing the control (culture media and PBS samples without HBV) and the lowest concentration of HBV spiked samples. Here, the statistical analysis was performed using one-way analysis of variance (ANOVA) with Tukey's posthoc test followed by Bartlett's test for equal variances for multiple comparisons, and statistical significance threshold was set at 0.05 (n=6, $p<0.05$). The statistical analyses demonstrated that the limit of detection was observed to be 10-100 IU/mL in culture media and PBS samples. Here, we present a reliable, repeatable, feasible, label-free, and fluorescence-free and repeatable technology that captures and detects intact HBV from biologically relevant solutions such as PBS, blood and culture media.

Many modifications and variations to this preferred embodiment will be apparent to those skilled in the art, which will be within the spirit and scope of the invention. Therefore, the invention should not be limited to the described embodiment. To ascertain the full scope of the invention, the following claims should be referenced.

What is claimed is:

1. A nanoplasmonic platform for the detection and quantification of at least one biological moiety in a sample, the nanoplasmonic platform comprising:
    a substrate having an immobilization layer;
    a plurality of nanoparticles immobilized on the immobilization layer; and
    at least one recognition element linked to the nanoparticles, the at least one recognition element configured to selectively bind to the at least one biological moiety;
    wherein the nanoplasmonic platform is adapted for the detection and quantification of the at least one biological moiety using localized surface plasmon resonance by correlating a wavelength shift and an extinction intensity corresponding to the sample received on the nanoplasmonic platform to determine whether the biological moiety has bound to the at least one recognition element on the nanoplasmonic platform and to determine a quantity of the biological moiety present in the sample.

2. The nanoplasmonic platform of claim 1, wherein the plurality of nanoparticles comprise gold, wherein the at least one biological moiety comprises a pathogen, and wherein the at least one recognition element comprises an antibody.

3. The nanoplasmonic platform of claim 1, wherein the substrate is optically transparent.

4. The nanoplasmonic platform of claim 3, wherein the substrate comprises at least one of polystyrene, glass parylene, quartz crystal, graphene and mica layers, and poly(methyl methacrylate).

5. The nanoplasmonic platform of claim 1, wherein the immobilization layer is poly-l-lysine and has amine-terminated groups that are used to immobilize the plurality of nanoparticles.

6. The nanoplasmonic platform of claim 1, wherein the immobilization layer is functionalized with at least one of amine group or thiol groups.

7. The nanoplasmonic platform of claim 1, wherein the at least one recognition element is a polyclonal antibody.

8. The nanoplasmonic platform of claim 1, wherein the at least one recognition element includes at least one of an anti-gp120 antibody, an anti-gp41 antibody, an anti-gp24 antibody, and lectin and the at least one biological moiety includes HIV.

9. The nanoplasmonic platform of claim 8, wherein the anti-gp120 antibody is adapted to bind to multiple subtypes of HIV.

10. The nanoplasmonic platform of claim 8, wherein, to link the at least one recognition element to the nanoparticles, a modified support surface is formed by preparing a surface of the plurality of nanoparticles using a mercaptoundecanoic acid to form carboxyl groups, N-Ethyl-N'-(3-dimethylaminopropyl) carbodiimide hydrochloride is reacted with the carboxyl groups to form an amine reactive intermediate, and the amine reactive intermediate is stabilized by N-hydroxysulfosuccinimide to form the modified support surface.

11. The nanoplasmonic platform of claim 10, wherein the modified support surface is linked to at least one of a protein A, a protein G, a protein AG, a Streptavidin protein, and a NeutrAvidin protein which is used to immobilize the anti-HIV gp120 antibody.

12. The nanoplasmonic platform of claim 1, wherein, after binding of the biological moiety to the recognition element, the nanoplasmonic platform exhibits an observable change in at least one of wavelength shift and extinction intensity.

13. The nanoplasmonic platform of claim 1, wherein the at least one biological moiety includes multiple pathogens.

14. The nanoplasmonic platform of claim 1, wherein the nanoplasmonic platform is a component of a microfluidic device having an inlet for reception of the sample in which the inlet is in fluid communication with a capture detection channel that includes at least one recognition element linked to the plurality of nanoparticles.

15. The nanoplasmonic platform of claim 14, wherein the microfluidic device further comprises a filter disposed between the inlet and the capture detection channel, the filter having a porosity that filters the sample to produce a filtered sample for selectively binding to the at least one recognition element.

16. A method of detecting a biological moiety in a sample using the nanoplasmonic platform of claim 1, the method comprising:
    receiving the sample on the nanoplasmonic platform to capture the biological moiety;
    performing localized surface plasmon resonance on the nanoplasmonic platform to obtain at least one of a wavelength shift and an extinction intensity corresponding to the sample received on the nanoplasmonic platform.

17. The method of claim 16, further comprising the step of correlating the at least one of the wavelength shift and the extension intensity corresponding to the sample received on the nanoplasmonic platform to determine whether the biological moiety has bound to the at least one recognition element on the nanoplasmonic platform.

18. The method of claim 16, further comprising the step of correlating the at least one of the wavelength shift and the extinction intensity corresponding to the sample received on the nanoplasmonic platform to determine a quantity of the biological moiety present in the sample.

19. The method of claim 16, wherein a biological moiety is a subtype of HIV and the nanoplasmonic platform is adapted to detect multiple subtypes of HIV.

20. The method of claim 16, wherein the nanoplasmonic platform is based on a microfluidic device having an inlet for reception of the sample in which the inlet is in fluid communication with a capture detection channel that includes at least one recognition element linked to the plurality of nanoparticles and the step of receiving the sample on the nanoplasmonic platform includes flowing the sample through the capture detection channel to selectively bind the biological moiety to the at least one recognition element.

21. The method of claim 20, wherein the microfluidic device further comprises a filter disposed between the inlet and the capture detection channel and the method further comprises the step of filtering the sample to produce a filtered sample prior to the step of selectively binding the biological moiety to the at least one recognition element in the capture detection channel.

* * * * *